(12) United States Patent
Prasad

(10) Patent No.: US 8,187,473 B2
(45) Date of Patent: May 29, 2012

(54) FUNCTIONAL TRANSITION METAL SILICATES

(75) Inventor: Yandapalli Durga Prasad, Andhra Pradesh (IN)

(73) Assignee: Kanumuru Rahul Raju, Hyderabad (IN)

(*) Notice: Subject to any disclaimer, the term of this patent is extended or adjusted under 35 U.S.C. 154(b) by 84 days.

(21) Appl. No.: 10/574,267

(22) PCT Filed: May 15, 2003

(86) PCT No.: PCT/IB03/02011
§ 371 (c)(1),
(2), (4) Date: Mar. 31, 2006

(87) PCT Pub. No.: WO2004/101435
PCT Pub. Date: Nov. 25, 2004

(65) Prior Publication Data
US 2006/0281961 A1 Dec. 14, 2006

(51) Int. Cl.
*C02F 1/68* (2006.01)

(52) U.S. Cl. ......... 210/764; 210/501; 423/326; 424/630

(58) Field of Classification Search .................. 210/764, 210/749, 501; 423/326; 424/618, 630
See application file for complete search history.

(56) References Cited

U.S. PATENT DOCUMENTS

| | | | |
|---|---|---|---|
| 3,836,633 A * | 9/1974 | Beschke | 423/326 |
| 3,888,683 A * | 6/1975 | Horai et al. | 428/404 |
| 3,912,519 A * | 10/1975 | Takagi et al. | 106/17 |
| 5,053,139 A | 10/1991 | Dodwell et al. | |
| 5,474,972 A * | 12/1995 | Sheen et al. | 423/326 |
| 5,632,904 A * | 5/1997 | Samad et al. | 210/764 |
| 6,284,364 B1 | 9/2001 | Node et al. | |
| 2004/0110738 A1 * | 6/2004 | Gillis et al. | 424/617 |

FOREIGN PATENT DOCUMENTS

| | | | |
|---|---|---|---|
| JP | 04182312 A | * | 6/1992 |
| JP | 8-283013 A | | 10/1996 |
| WO | WO-92/10292 A | | 6/1992 |
| WO | WO-99/27942 A | | 6/1999 |
| WO | WO-03/075664 A | | 9/2003 |
| WO | WO-03/089112 A | | 10/2003 |

OTHER PUBLICATIONS

Definition of "do" Merriam-Webster online dictionary, 2009.*
Machine translation of JP 08-283013 (obtained from JPO 10-09).*
Jean-Paul Latge, "Aspergillus fumigatus and Aspergillosis," Clinical Microbiology Reviews, Apr. 1999, p. 310-350.*

(Continued)

*Primary Examiner* — Joseph Drodge
*Assistant Examiner* — Lucas Stelling
(74) *Attorney, Agent, or Firm* — Birch, Stewart, Kolasch & Birch, LLP

(57) ABSTRACT

The present invention provides a functional transition metal silicate (FTMS) effective as a decontaminant, a disinfectant, a detoxificant, a protectant, a microbicide or combination thereof, comprising a ratio of transition metal to silica in the transition metal silicate in a predetermined range and a structural composition for said effectiveness, said FTMS being capable of being immobilized on a suitable materials or incorporating into resins and/or coating along with resins on suitable materials.

10 Claims, 56 Drawing Sheets

Figure 1B:
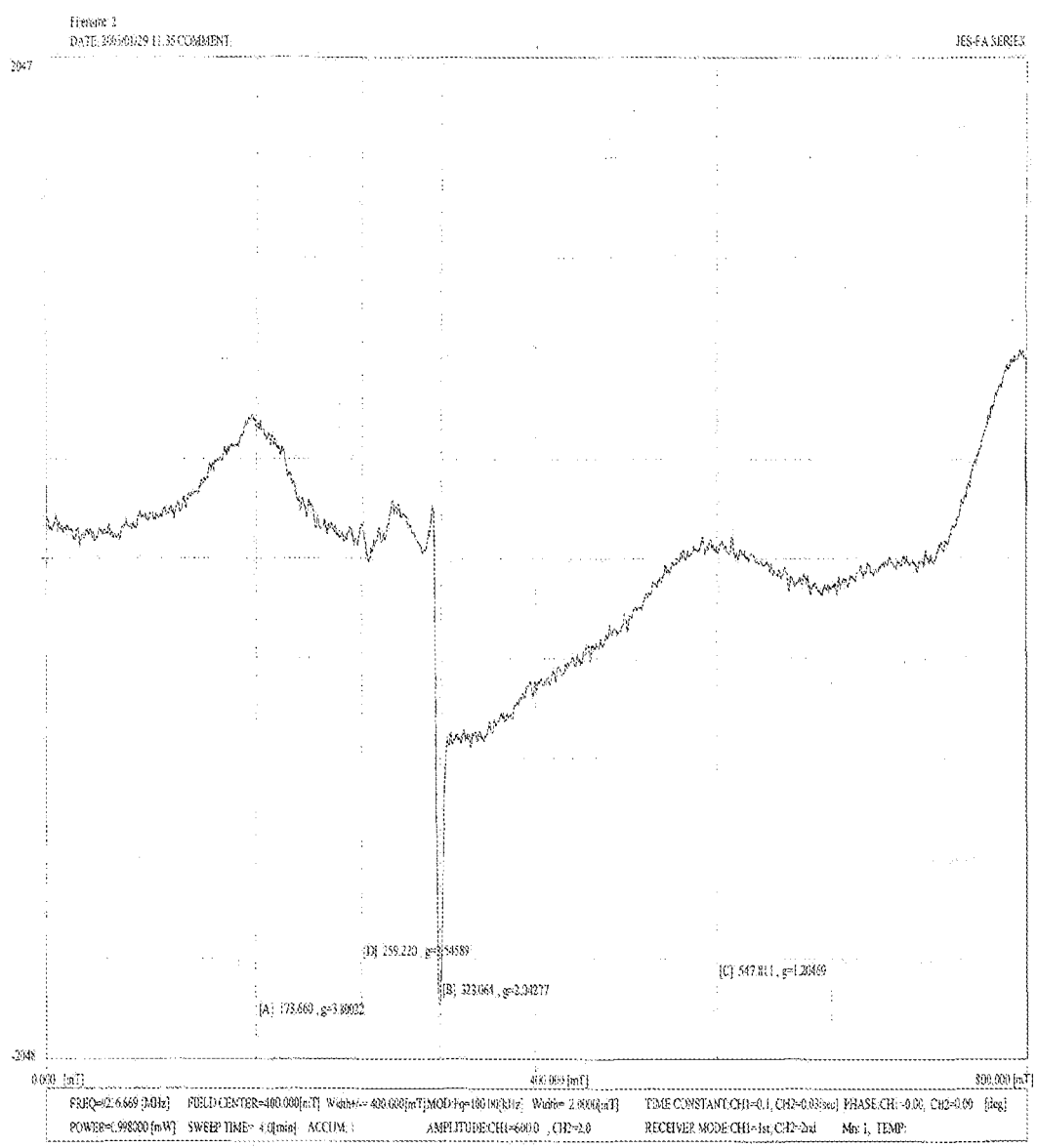

ESR (Electron spin resonance) spectrometer analysis of cupric silicate (synthesized at acidic reaction conditions).

OTHER PUBLICATIONS

McKeown, "X-ray absorption spectroscopic study of copper in an amorphous copper silicate: chrysocolla" (1994), Journal of Non-Crystalline Solids, 180 (1), pp. 1-10. (abstract only).*

English Language translation of JPO 04-182312.*

Database CA 'Online! Chemical Abstracts Service, Columbus, Ohio, US; Komatsu, Yoshinobu et al., "Amorphous copper silicates, their manufacture, and their uses in antibacterial agents and antifouling coatings" retrieved from STN Database accession No. 126:33988 CA XP0022771162.

Database WPI Section Ch, Week 199423 Derwent Publications Ltd., London, GB; AN 1994-186002 XP002271163 JP 6-121926 A May 6, 1994.

* cited by examiner

FIG. 1A

Composition analysis of cupric silicate (synthesized at acidic reaction conditions) using EDAX attached to SEM (Scanning Electron Microscope).

Weight % Element

| Filename | o k | NaK | Sik | ClK | CuK |
|---|---|---|---|---|---|
| II.spc | 45.39 | 1.74 | 6.33 | 13.92 | 32.63 |

Atomic % Element

| Filename | o k | NaK | Sik | ClK | CuK |
|---|---|---|---|---|---|
| II.spc | 70.15 | 1.87 | 5.57 | 9.71 | 12.70 |

ESR (Electron spin resonance) spectrometer analysis of cupric silicate (synthesized at acidic reaction conditions).

XRD (X-ray diffraction) pattern of cupric silicate (synthesized at acidic reaction conditions).

FIG. 1D

XRD (X-ray diffraction) pattern of cupric silicate (synthesized at acidic reaction conditions).

X'Pert Graphics & Identify  
(searched) peak list: 2-R 2

User-1  
1/25/03 14:38

Original scan: 2-R  
Description of scan:

Date: 1/24/03 14:25

Used wavelength:  K-Alpha1

K-Alpha1 wavelength (Å):  1.54056  
K-Alpha2 wavelength (Å):  1.54439  
K-Alpha2/K-Alpha1 intensity ratio :  0.50000  
K-Alpha wavelength (Å):  1.54056  
K-Beta wavelength (Å):  1.39222

Peak search parameter set:  As Measured Intensities  
Set created:  1/8/03 13:03  
Peak positions defined by:  Minimum of 2nd derivative  
Minimum peak tip width (°2Theta):  0.00  
Minimum peak tip width (°2Theta):  1.00  
Peak base width (°2Theta):  2.00  
Minimum significance:  0.60

| d-spacing (Å) | Relative Intensity (%) | Angle (°2Theta) | Peak Height (counts/s) | Background (counts/s) | Tip Width (°2Theta) | Significance |
|---|---|---|---|---|---|---|
| 5.48673 | 100.00 | 16.14080 | 3156.22 | 923.90 | 0.44000 | 19.72 |
| 5.00327 | 20.71 | 17.71241 | 653.63 | 972.81 | 0.64000 | 4.14 |
| 3.43222 | 3.34 | 25.93831 | 105.37 | 906.45 | 0.48000 | 1.22 |
| 2.84108 | 30.80 | 31.46211 | 972.17 | 1038.45 | 0.20000 | 0.64 |
| 2.77130 | 75.78 | 32.27568 | 2391.87 | 1069.38 | 0.28000 | 2.91 |
| 2.27354 | 54.06 | 39.60778 | 1706.22 | 998.03 | 0.40000 | 7.76 |
| 1.82288 | 14.67 | 49.99281 | 463.03 | 916.51 | 0.20000 | 0.77 |
| 1.71366 | 10.53 | 53.42238 | 332.20 | 906.86 | 0.48000 | 1.89 |
| 1.36697 | 5.89 | 68.59540 | 185.87 | 802.15 | 0.48000 | 0.84 |
| 1.24612 | 1.96 | 76.36139 | 61.84 | 747.02 | 0.96000 | 0.83 |

Philips Analytical

Page: 1

FIG. 2A

Composition analysis of cupric silicate (synthesized at acidic reaction conditions and at high temperature $70^0$ C to $90^0$ C) using EDAX attached to SEM (Scanning Electron Microscope).

Weight % by Element

| Filename  | o k   | NaK  | SiK   | ClK  | CuK   |
|-----------|-------|------|-------|------|-------|
| c-nat.spc | 45.84 | 0.89 | 27.31 | 4.63 | 21.33 |

Atomic % Element

| Filename  | o k   | NaK  | SiK   | ClK  | CuK  |
|-----------|-------|------|-------|------|------|
| c-nat.spc | 65.98 | 0.89 | 22.39 | 3.01 | 7.73 |

ESR (Electron spin resonance) spectrometer analysis of cupric silicate (synthesized at acidic reaction conditions and at higher temperature $70^0$ C to $90^0$ C).

XRD (X-ray diffraction) pattern of cupric silicate (synthesized at acidic reaction conditions and at higher temperature 70° C to 90° C).

FIG. 2D

XRD (X-ray diffraction) pattern of cupric silicate (synthesized at acidic reaction conditions and at higher temperature 70°C to 90°C).

X'Pert Graphics & Identify  
(searched) peak list: CN-R 2

User-1  
2/3/03 11:54

Original scan: CN-R  
Description of scan:

Date: 2/2/03 16:09

Used wavelength: K-Alpha1

K-Alpha1 wavelength (Å): 1.54056  
K-Alpha2 wavelength (Å): 1.54439  
K-Alpha2/K-Alpha1 intensity ratio: 0.50000  
K-Alpha wavelength (Å): 1.54056  
K-Beta wavelength (Å): 1.39222

Peak search parameter set: As Measured Intensities  
Set created: 1/8/03 13:03  
Peak positions defined by: Minimum of 2nd derivative  
Minimum peak tip width (°2Theta): 0.00  
Minimum peak tip width (°2Theta): 1.00  
Peak base width (°2Theta): 2.00  
Minimum significance: 0.60

| d-spacing (Å) | Relative Intensity (%) | Angle (°2Theta) | Peak Height (counts/s) | Background (counts/s) | Tip Width (°2Theta) | Significance |
|---|---|---|---|---|---|---|
| 5.46662 | 100.00 | 16.20057 | 835.63 | 647.06 | 0.40000 | 5.94 |
| 5.01048 | 15.55 | 17.68674 | 129.92 | 702.61 | 0.64000 | 0.71 |
| 2.77436 | 84.58 | 32.23910 | 706.74 | 690.34 | 0.40000 | 3.61 |
| 2.27554 | 60.14 | 39.57159 | 502.52 | 580.44 | 0.56000 | 8.46 |
| 1.82094 | 18.29 | 50.04991 | 152.83 | 524.53 | 0.40000 | 0.90 |
| 1.71674 | 13.71 | 53.31888 | 114.53 | 522.91 | 0.40000 | 0.62 |
| 1.46762 | 5.69 | 63.31614 | 47.53 | 489.95 | 0.28000 | 0.60 |

Philips Analytical

Page: 1

FIG. 3A

Composition analysis of cupric silicate (synthesized at neutral (pH 6-7) reaction conditions) using EDAX attached to SEM (Scanning Electron Microscope).

Weight % by Element

| Filename | o k | NaK | Sik | ClK | CuK |
|---|---|---|---|---|---|
| VI.spc | 49.47 | 1.06 | 22.59 | 4.27 | 22.62 |

Atomic % by Element

| Filename | o k | NaK | Sik | ClK | CuK |
|---|---|---|---|---|---|
| VI.spc | 69.98 | 1.04 | 18.20 | 2.73 | 8.06 |

ESR (Electron spin resonance) spectrometer analysis of cupric silicate (synthesized at neutral (pH 6-7) reaction conditions).

XRD (X-ray diffraction) pattern of cupric silicate (synthesized at neutral (pH 6-7) reaction conditions).

FIG. 3D

XRD (X-ray diffraction) pattern of cupric silicate (synthesized at neutral (pH 6-7) reaction conditions).

X'Pert Graphics & Identify  
(searched) peak list: 6-R 2

User-1  
1/25/03 14:41

Original scan: 6-R  
Description of scan:

Date: 1/25/03 11:54

Used wavelength: K-Alpha1

| | |
|---|---|
| K-Alpha1 wavelength (Å): | 1.54056 |
| K-Alpha2 wavelength (Å): | 1.54439 |
| K-Alpha2/K-Alpha1 intensity ratio : | 0.50000 |
| K-Alpha wavelength (Å): | 1.54056 |
| K-Beta wavelength (Å): | 1.39222 |

| | |
|---|---|
| Peak search parameter set: | As Measured Intensities |
| Set created: | 1/8/03 13:03 |
| Peak positions defined by: | Minimum of 2nd derivative |
| Minimum peak tip width (°2Theta): | 0.00 |
| Minimum peak tip width (°2Theta): | 1.00 |
| Peak base width (°2Theta): | 2.00 |
| Minimum significance: | 0.60 |

| d-spacing (Å) | Relative Intensity (%) | Angle (°2Theta) | Peak Height (counts/s) | Background (counts/s) | Tip Width (°2Theta) | Significance |
|---|---|---|---|---|---|---|
| 5.46823 | 100.00 | 16.19577 | 940.90 | 822.33 | 0.44000 | 5.24 |
| 4.99966 | 19.39 | 17.72532 | 182.41 | 854.59 | 0.64000 | 0.74 |
| 2.76987 | 81.24 | 32.29276 | 764.43 | 1159.63 | 0.36000 | 2.79 |
| 2.26420 | 73.85 | 39.77809 | 694.85 | 945.62 | 0.36000 | 2.83 |
| 1.82157 | 14.47 | 50.03142 | 136.11 | 789.55 | 0.48000 | 0.76 |
| 1.71307 | 10.80 | 53.44225 | 101.61 | 812.60 | 0.80000 | 1.14 |

Philips Analytical

Page: 1

FIG. 4A

Composition analysis of cupric silicate (synthesized at basic (pH 10-11) reaction conditions) using EDAX attached to SEM (Scanning Electron Microscope).

Weight % by Element

| Filenames | o k | NaK | Sik | CuK |
|---|---|---|---|---|
| VII.spc | 54.33 | 0.44 | 24.65 | 20.58 |

Atomic % by Element

| Filenames | o k | NaK | Sik | CuK |
|---|---|---|---|---|
| VII.spc | 73.56 | 0.41 | 19.01 | 7.02 |

ESR (Electron spin resonance) spectrometer analysis of cupric silicate (synthesized at basic (pH 10-11) reaction conditions).

XRD (X-ray diffraction) pattern of cupric silicate (synthesized at basic (pH 10-11) reaction conditions).

FIG. 4D

XRD (X-ray diffraction) pattern of cupric silicate (synthesized at basic (pH 10-11) reaction conditions).

X'Pert Graphics & Identify
(searched) peak list: 7-R 2

User-1
1/25/03 14:42

Original scan: 7-R
Description of scan:

Date: 1/25/03 12:44

Used wavelength:  K-Alpha1

K-Alpha1 wavelength (Å): 1.54056
K-Alpha2 wavelength (Å): 1.54439
K-Alpha2/K-Alpha1 intensity ratio : 0.50000
K-Alpha wavelength (Å): 1.54056
K-Beta wavelength (Å): 1.39222

Peak search parameter set: As Measured Intensities
Set created: 1/8/03 13:03
Peak positions defined by: Minimum of 2nd derivative
Minimum peak tip width (°2Theta): 0.00
Minimum peak tip width (°2Theta): 1.00
Peak base width (°2Theta): 2.00
Minimum significance: 0.60

| d-spacing (Å) | Relative Intensity (%) | Angle (°2Theta) | Peak Height (counts/s) | Background (counts/s) | Tip Width (°2Theta) | Significance |
|---|---|---|---|---|---|---|
| 4.01966 | 16.81 | 22.09561 | 25.68 | 860.24 | 0.96000 | 0.66 |
| 3.34217 | 100.00 | 26.64983 | 152.74 | 982.28 | 0.20000 | 0.78 |
| 3.03278 | 66.38 | 29.42686 | 101.40 | 1024.95 | 0.48000 | 0.63 |

Philips Analytical

Page: 1

FIG. 5A

Composition analysis of cupric silicate (synthesized at extreme acidic reaction conditions (below pH 2) by addition of 10 ml HCl ) using EDAX attached to SEM (Scanning Electron Microscope).

Weight % by Element

| Filenames | o k | NaK | Sik | ClK | CuK |
|---|---|---|---|---|---|
| C10.spc | 45.69 | 1.06 | 32.63 | 3.30 | 17.33 |

Atomic % by Element

| Filenames | o k | NaK | Sik | ClK | CuK |
|---|---|---|---|---|---|
| C10.spc | 64.47 | 1.04 | 26.23 | 2.10 | 6.16 |

ESR (Electron spin resonance) spectrometer analysis of cupric silicate (synthesized at extreme acidic reaction conditions (below pH 2) by addition of 10 ml HCl).

XRD (X-ray diffraction) pattern of cupric silicate ( synthesized at extreme acidic reaction conditions (below pH 2) by addition of 10 ml HCl ).

FIG. 5D

XRD (X-ray diffraction) pattern of cupric silicate (synthesized at extreme acidic reaction conditions (below pH 2) by addition of 10 ml HCl).

| X'Pert Graphics & Identify | | User-1 |
|---|---|---|
| (searched) peak list: C10-R 2 | | 2/3/03 11:56 |

| | |
|---|---|
| Original scan: C10-R | Date: 2/2/03 15:13 |
| Description of scan: | |

| | |
|---|---|
| Used wavelength: | K-Alpha1 |
| K-Alpha1 wavelength (Å): | 1.54056 |
| K-Alpha2 wavelength (Å): | 1.54439 |
| K-Alpha2/K-Alpha1 intensity ratio : | 0.50000 |
| K-Alpha wavelength (Å): | 1.54056 |
| K-Beta wavelength (Å): | 1.39222 |

| | |
|---|---|
| Peak search parameter set: | As Measured Intensities |
| Set created: | 1/8/03 13:03 |
| Peak positions defined by: | Minimum of 2nd derivative |
| Minimum peak tip width (°2Theta): | 0.00 |
| Minimum peak tip width (°2Theta): | 1.00 |
| Peak base width (°2Theta): | 2.00 |
| Minimum significance: | 0.60 |

| d-spacing (Å) | Relative Intensity (%) | Angle (°2Theta) | Peak Height (counts/s) | Background (counts/s) | Tip Width (°2Theta) | Significance |
|---|---|---|---|---|---|---|
| 7.39149 | 15.98 | 11.96350 | 64.02 | 545.13 | 0.80000 | 0.73 |
| 5.46724 | 100.00 | 16.19872 | 400.70 | 610.14 | 0.32000 | 2.15 |
| 2.77097 | 98.52 | 32.27956 | 394.77 | 587.64 | 0.20000 | 0.79 |
| 2.26751 | 82.36 | 39.71761 | 330.02 | 436.05 | 0.28000 | 1.67 |
| 1.82010 | 20.70 | 50.07447 | 82.93 | 377.75 | 0.48000 | 0.98 |
| 1.71117 | 15.69 | 53.50644 | 62.86 | 365.08 | 0.80000 | 0.92 |

Philips Analytical                                                                                                   Page: 1

FIG. 6A

Composition analysis of cupric silicate (synthesized at extreme acidic reaction conditions (below pH 2) by addition of 20 ml HCl ) using EDAX attached to SEM (Scanning Electron Microscope).

Weight % by Element

| Filenames | o k | NaK | Sik | ClK | CuK |
|---|---|---|---|---|---|
| C20.spc | 52.91 | 0.60 | 33.23 | 1.92 | 11.34 |

Atomic % by Element

| Filenames | o k | NaK | Sik | ClK | CuK |
|---|---|---|---|---|---|
| C20.spc | 69.64 | 0.55 | 24.91 | 1.14 | 3.76 |

ESR (Electron spin resonance) spectrometer analysis of cupric silicate (synthesized at extreme acidic reaction conditions (below pH 2) by addition of 20 ml HCl).

XRD (X-ray diffraction) pattern of cupric silicate (synthesized at extreme acidic reaction conditions (below pH 2) by addition of 20 ml HCl).

FIG. 6D

XRD (X-ray diffraction) pattern of cupric silicate (synthesized at extreme acidic reaction conditions (below pH 2) by addition of 20 ml HCl).

X'Pert Graphics & Identify  
(searched) peak list: C20-R 2

User-1  
2/3/03 11:57

Original scan: C20-R  
Description of scan:

Date: 2/2/03 14:43

Used wavelength: K-Alpha1

K-Alpha1 wavelength (Å): 1.54056  
K-Alpha2 wavelength (Å): 1.54439  
K-Alpha2/K-Alpha1 intensity ratio: 0.50000  
K-Alpha wavelength (Å): 1.54056  
K-Beta wavelength (Å): 1.39222

Peak search parameter set: As Measured Intensities  
Set created: 1/8/03 13:03  
Peak positions defined by: Minimum of 2nd derivative  
Minimum peak tip width (°2Theta): 0.00  
Minimum peak tip width (°2Theta): 1.00  
Peak base width (°2Theta): 2.00  
Minimum significance: 0.60

| d-spacing (Å) | Relative Intensity (%) | Angle (°2Theta) | Peak Height (counts/s) | Background (counts/s) | Tip Width (°2Theta) | Significance |
|---|---|---|---|---|---|---|
| 5.44576 | 100.00 | 16.26305 | 541.23 | 653.67 | 0.20000 | 0.71 |
| 5.03216 | 19.73 | 17.60991 | 106.76 | 721.64 | 0.48000 | 0.77 |
| 2.76378 | 76.53 | 32.36589 | 414.21 | 698.97 | 0.56000 | 3.99 |
| 2.26021 | 67.52 | 39.85131 | 365.45 | 515.17 | 0.56000 | 4.06 |
| 2.01957 | 7.07 | 44.84173 | 38.28 | 483.78 | 0.24000 | 0.70 |
| 1.82106 | 15.18 | 50.04628 | 82.15 | 457.19 | 0.64000 | 0.84 |
| 1.71148 | 11.43 | 53.49579 | 61.84 | 451.40 | 0.80000 | 1.24 |

FIG. 7A

Composition analysis of zinc silicate (synthesized at neutral (pH 6-7) reaction conditions) using EDAX attached to SEM (Scanning Electron Microscope).

Weight % by Element

| Filenames | O k | Sik | ClK | ZnK |
|---|---|---|---|---|
| nine.spc | 35.71 | 4.89 | 0.08 | 59.32 |

Atomic % by Element

| Filenames | O k | Sik | ClK | ZnK |
|---|---|---|---|---|
| nine.spc | 67.32 | 5.25 | 0.06 | 27.37 |

ESR (Electron spin resonance) spectrometer analysis of zinc silicate (synthesized at neutral (pH 6-7) reaction conditions).

XRD (X-ray diffraction) pattern of zinc silicate (synthesized at neutral (pH 6-7) reaction conditions).

FIG. 7D

XRD (X-ray diffraction) pattern of zinc silicate (synthesized at neutral (pH 6-7) reaction conditions).

X'Pert Graphics & Identify  
(searched) peak list: 21-R 2

User-1  
1/25/03 14:39

Original scan: 21-R  
Description of scan:

Date: 1/25/03 13:25

Used wavelength:                              K-Alpha1

K-Alpha1 wavelength (Å):                      1.54056  
K-Alpha2 wavelength (Å):                      1.54439  
K-Alpha2/K-Alpha1 intensity ratio :           0.50000  
K-Alpha wavelength (Å):                       1.54056  
K-Beta wavelength (Å):                        1.39222

Peak search parameter set:                    As Measured Intensities  
Set created:                                  1/8/03 13:03  
Peak positions defined by:                    Minimum of 2nd derivative  
Minimum peak tip width (°2Theta):             0.00  
Minimum peak tip width (°2Theta):             1.00  
Peak base width (°2Theta):                    2.00  
Minimum significance:                         0.60

| d-spacing (Å) | Relative Intensity (%) | Angle (°2Theta) | Peak Height (counts/s) | Background (counts/s) | Tip Width (°2Theta) | Significance |
|---|---|---|---|---|---|---|
| 4.24766 | 9.82 | 20.89591 | 43.60 | 386.64 | 0.48000 | 0.85 |
| 3.15351 | 59.30 | 28.27636 | 263.36 | 514.45 | 0.48000 | 1.66 |
| 2.88286 | 40.51 | 30.99464 | 179.93 | 574.24 | 0.40000 | 0.76 |
| 2.73150 | 100.00 | 32.75904 | 444.15 | 691.51 | 0.28000 | 0.83 |
| 2.49483 | 21.20 | 35.96794 | 94.17 | 671.04 | 0.64000 | 0.70 |
| 2.09711 | 13.25 | 43.09916 | 58.83 | 334.47 | 0.64000 | 0.73 |
| 1.67436 | 9.61 | 54.77999 | 42.67 | 370.46 | 0.64000 | 0.92 |
| 1.55031 | 69.13 | 59.58455 | 307.02 | 427.76 | 0.40000 | 0.84 |

Philips Analytical

Page: 1

FIG. 8A

Composition analysis of zinc silicate (synthesized at extreme acidic (below pH2) reaction conditions) using EDAX attached to SEM (Scanning Electron Microscope).

Weight % by Element

| Filenames  | o k   | ZnL   | NaK  | Sik   | ClK  |
|------------|-------|-------|------|-------|------|
| zinc-10.spc | 35.59 | 41.94 | 0.00 | 17.04 | 5.43 |

Atomic % by Element

| Filenames  | o k   | ZnL   | NaK  | Sik   | ClK  |
|------------|-------|-------|------|-------|------|
| zinc-10.spc | 61.35 | 17.69 | 0.00 | 16.73 | 4.22 |

ESR (Electron spin resonance) spectrometer analysis of zinc silicate (synthesized at extreme acidic (below pH2) reaction conditions).

ESR (Electron spin resonance) spectrometer analysis of zinc silicate (synthesized at extreme acidic (below pH2) reaction conditions).

XRD (X-ray diffraction) pattern of zinc silicate (synthesized at extreme acidic (below pH2) reaction conditions).

FIG. 8E

XRD (X-ray diffraction) pattern of zinc silicate (synthesized at extreme acidic (below pH2) reaction conditions).

X'Pert Graphics & Identify  
(searched) peak list: XZ-R 2

User-1  
2/3/03 11:58

Original scan: XZ-R  
Description of scan:

Date: 2/1/03 18:50

| Used wavelength: | K-Alpha1 |
|---|---|
| K-Alpha1 wavelength (Å): | 1.54056 |
| K-Alpha2 wavelength (Å): | 1.54439 |
| K-Alpha2/K-Alpha1 intensity ratio : | 0.50000 |
| K-Alpha wavelength (Å): | 1.54056 |
| K-Beta wavelength (Å): | 1.39222 |

| Peak search parameter set: | As Measured Intensities |
|---|---|
| Set created: | 1/8/03 13:03 |
| Peak positions defined by: | Minimum of 2nd derivative |
| Minimum peak tip width (°2Theta): | 0.00 |
| Minimum peak tip width (°2Theta): | 1.00 |
| Peak base width (°2Theta): | 2.00 |
| Minimum significance: | 0.60 |

| d-spacing (Å) | Relative Intensity (%) | Angle (°2Theta) | Peak Height (counts/s) | Background (counts/s) | Tip Width (°2Theta) | Significance |
|---|---|---|---|---|---|---|
| 7.98264 | 100.00 | 11.07467 | 2079.88 | 453.30 | 0.48000 | 16.11 |
| 5.33677 | 10.63 | 16.59748 | 221.17 | 343.67 | 0.32000 | 1.31 |
| 4.00484 | 19.52 | 22.17845 | 406.04 | 474.57 | 0.28000 | 0.97 |
| 3.56647 | 16.16 | 24.94587 | 336.14 | 510.88 | 0.24000 | 1.03 |
| 3.14366 | 10.46 | 28.36683 | 217.55 | 465.82 | 0.48000 | 4.95 |
| 2.93766 | 15.03 | 30.40232 | 312.67 | 418.68 | 0.24000 | 1.39 |
| 2.86706 | 20.14 | 31.16978 | 418.81 | 403.81 | 0.32000 | 2.08 |
| 2.72163 | 31.97 | 32.88120 | 664.98 | 370.63 | 0.32000 | 4.93 |
| 2.67080 | 40.17 | 33.52527 | 835.44 | 358.14 | 0.36000 | 7.23 |
| 2.60200 | 15.53 | 34.43904 | 322.95 | 340.43 | 0.24000 | 0.93 |
| 2.46786 | 3.83 | 36.37469 | 79.68 | 303.54 | 0.32000 | 1.82 |
| 2.37176 | 23.66 | 37.90343 | 492.02 | 275.31 | 0.36000 | 4.69 |
| 2.16675 | 2.30 | 41.64812 | 47.90 | 237.27 | 0.48000 | 0.80 |
| 2.01636 | 14.86 | 44.91711 | 308.99 | 237.75 | 0.64000 | 5.99 |
| 1.95400 | 4.79 | 46.43299 | 99.53 | 226.89 | 0.72000 | 2.14 |
| 1.89620 | 2.90 | 47.93553 | 60.26 | 216.13 | 0.64000 | 1.07 |
| 1.78961 | 6.59 | 50.98829 | 136.97 | 214.24 | 0.40000 | 0.92 |
| 1.76470 | 6.90 | 51.76088 | 143.48 | 213.02 | 0.32000 | 0.65 |
| 1.68726 | 11.52 | 54.32631 | 239.59 | 208.98 | 0.32000 | 1.25 |
| 1.57830 | 19.87 | 58.42442 | 413.19 | 213.32 | 0.40000 | 6.07 |
| 1.55167 | 7.86 | 59.52677 | 163.47 | 215.82 | 0.24000 | 0.83 |
| 1.51555 | 8.99 | 61.09471 | 186.93 | 219.37 | 0.32000 | 1.26 |
| 1.43353 | 1.90 | 65.00406 | 39.44 | 195.08 | 0.56000 | 0.61 |
| 1.36374 | 2.96 | 68.78101 | 61.53 | 182.93 | 0.64000 | 0.99 |
| 1.29976 | 2.39 | 72.68780 | 49.61 | 155.06 | 0.64000 | 0.68 |
| 1.23245 | 2.46 | 77.36409 | 51.16 | 137.24 | 0.48000 | 0.76 |

Philips Analytical

FIG. 9A

Composition analysis of silver silicate (synthesized at neutral (pH 6-7) reaction conditions) using EDAX attached to SEM (Scanning Electron Microscope).

Weight % by Element

| Filenames | O k | NaK | SiK | ClK | AgL |
|---|---|---|---|---|---|
| Silver5.spc | 29.55 | 0.56 | 2.63 | 15.79 | 51.47 |

Atomic % by Element

| Filenames | O k | NaK | SiK | ClK | AgL |
|---|---|---|---|---|---|
| Silver5.spc | 63.96 | 0.85 | 3.25 | 15.42 | 16.52 |

ESR (Electron spin resonance) spectrometer analysis of silver silicate (synthesized at neutral (pH 6-7) reaction conditions).

XRD (X-ray diffraction) pattern of silver silicate (synthesized at neutral (pH 6-7) reaction conditions).

FIG. 9D

XRD (X-ray diffraction) pattern of silver silicate (synthesized at neutral (pH 6-7) reaction conditions).

X'Pert Graphics & Identify  
(searched) peak list: So-r 2

User-1  
2/3/03 11:52

Original scan: So-r  
Description of scan:

Date: 2/3/03 11:12

| | |
|---|---|
| Used wavelength: | K-Alpha1 |
| K-Alpha1 wavelength (Å): | 1.54056 |
| K-Alpha2 wavelength (Å): | 1.54439 |
| K-Alpha2/K-Alpha1 intensity ratio : | 0.50000 |
| K-Alpha wavelength (Å): | 1.54056 |
| K-Beta wavelength (Å): | 1.39222 |

| | |
|---|---|
| Peak search parameter set: | As Measured Intensities |
| Set created: | 1/8/03 13:03 |
| Peak positions defined by: | Minimum of 2nd derivative |
| Minimum peak tip width (°2Theta): | 0.00 |
| Minimum peak tip width (°2Theta): | 1.00 |
| Peak base width (°2Theta): | 2.00 |
| Minimum significance: | 0.60 |

| d-spacing (Å) | Relative Intensity (%) | Angle (°2Theta) | Peak Height (counts/s) | Background (counts/s) | Tip Width (°2Theta) | Significance |
|---|---|---|---|---|---|---|
| 12.51901 | 0.61 | 7.05514 | 24.25 | 269.08 | 0.32000 | 0.75 |
| 3.84145 | 1.61 | 23.13452 | 63.48 | 84.62 | 0.24000 | 0.85 |
| 3.19616 | 46.53 | 27.89129 | 1835.66 | 84.32 | 0.32000 | 11.62 |
| 3.02038 | 15.33 | 29.55040 | 604.98 | 86.85 | 0.40000 | 10.85 |
| 2.76936 | 100.00 | 32.29885 | 3945.11 | 91.02 | 0.36000 | 24.39 |
| 2.48336 | 2.75 | 36.13978 | 108.38 | 69.78 | 0.20000 | 1.06 |
| 2.27608 | 3.61 | 39.56180 | 142.47 | 63.39 | 0.24000 | 1.46 |
| 2.08218 | 3.16 | 43.42372 | 124.78 | 58.90 | 0.44000 | 4.34 |
| 1.96033 | 61.37 | 46.27446 | 2421.27 | 59.81 | 0.44000 | 31.71 |
| 1.90300 | 4.13 | 47.75348 | 162.86 | 60.29 | 0.20000 | 0.87 |
| 1.86696 | 3.87 | 48.73456 | 152.60 | 60.60 | 0.28000 | 2.05 |
| 1.67244 | 17.12 | 54.84804 | 675.21 | 58.99 | 0.40000 | 11.19 |
| 1.60159 | 18.06 | 57.49439 | 712.55 | 55.15 | 0.20000 | 2.33 |
| 1.52203 | 0.97 | 60.80730 | 38.34 | 49.06 | 0.32000 | 0.61 |
| 1.43528 | 1.08 | 64.91550 | 42.68 | 50.99 | 0.28000 | 1.03 |
| 1.38831 | 5.42 | 67.39817 | 213.70 | 52.15 | 0.24000 | 1.32 |
| 1.27274 | 3.54 | 74.48880 | 139.61 | 66.51 | 0.48000 | 3.96 |
| 1.24157 | 13.09 | 76.69181 | 516.25 | 62.23 | 0.24000 | 2.43 |
| 1.23836 | 11.31 | 76.92707 | 446.10 | 61.78 | 0.16000 | 0.61 |

Philips Analytical

Page: 1

FIG. 10A

Composition analysis of silver silicate (synthesized at acidic (pH 2) reaction conditions) using EDAX attached to SEM (Scanning Electron Microscope).

Weight % by Element

| Filenames | o k | NaK | Sik | ClK | AgL |
|---|---|---|---|---|---|
| Silver-4.spc | 52.01 | 4.83 | 20.85 | 0.46 | 21.86 |

Atomic % by Element

| Filenames | o k | NaK | Sik | ClK | AgL |
|---|---|---|---|---|---|
| Silver-4.spc | 73.57 | 4.75 | 16.80 | 0.29 | 4.59 |

ESR (Electron spin resonance) spectrometer analysis of silver silicate (synthesized at acidic (pH 2) reaction conditions).

XRD (X-ray diffraction) pattern of silver silicate (synthesized at acidic (pH 2) reaction conditions).

FIG. 10D

XRD (X-ray diffraction) pattern of silver silicate (synthesized at acidic (pH 2) reaction conditions).

X'Pert Graphics & Identify
(searched) peak list: Sn—r 2

User-1
2/3/03 12:41

Original scan: Sn—r
Description of scan:

Date: 2/3/03 12:12

| Used wavelength: | K-Alpha1 |
|---|---|
| K-Alpha1 wavelength (Å): | 1.54056 |
| K-Alpha2 wavelength (Å): | 1.54439 |
| K-Alpha2/K-Alpha1 intensity ratio : | 0.50000 |
| K-Alpha wavelength (Å): | 1.54056 |
| K-Beta wavelength (Å): | 1.39222 |

| Peak search parameter set: | As Measured Intensities |
|---|---|
| Set created: | 1/8/03 13:03 |
| Peak positions defined by: | Minimum of 2nd derivative |
| Minimum peak tip width (°2Theta): | 0.00 |
| Minimum peak tip width (°2Theta): | 1.00 |
| Peak base width (°2Theta): | 2.00 |
| Minimum significance: | 0.60 |

| d-spacing (Å) | Relative Intensity (%) | Angle (°2Theta) | Peak Height (counts/s) | Background (counts/s) | Tip Width (°2Theta) | Significance |
|---|---|---|---|---|---|---|
| 3.89288 | 7.31 | 22.82476 | 162.05 | 285.57 | 0.20000 | 0.84 |
| 3.04209 | 100.00 | 29.33483 | 2217.87 | 286.93 | 0.44000 | 27.45 |
| 2.80105 | 2.99 | 31.92363 | 66.30 | 297.07 | 0.64000 | 0.85 |
| 2.54412 | 18.81 | 35.24794 | 417.13 | 264.05 | 0.24000 | 2.56 |
| 2.32266 | 15.21 | 38.73633 | 337.42 | 211.76 | 0.32000 | 3.87 |
| 2.13433 | 30.40 | 42.31091 | 674.27 | 184.90 | 0.24000 | 5.12 |
| 1.95266 | 8.89 | 46.46684 | 197.27 | 168.22 | 0.36000 | 3.23 |
| 1.90573 | 30.86 | 47.68093 | 684.55 | 162.50 | 0.24000 | 2.62 |
| 1.88838 | 24.63 | 48.14670 | 546.21 | 160.31 | 0.32000 | 2.62 |
| 1.65610 | 3.33 | 55.43541 | 73.96 | 136.14 | 0.24000 | 0.81 |
| 1.63624 | 6.25 | 56.16747 | 138.52 | 134.86 | 0.20000 | 0.81 |
| 1.54698 | 7.23 | 59.72562 | 160.38 | 146.27 | 0.28000 | 2.15 |
| 1.47111 | 4.99 | 63.14884 | 110.71 | 134.86 | 0.32000 | 2.37 |
| 1.40804 | 10.18 | 66.33090 | 225.85 | 116.60 | 0.32000 | 3.21 |
| 1.36874 | 1.37 | 68.49464 | 30.40 | 107.27 | 0.48000 | 0.82 |
| 1.34028 | 2.30 | 70.15949 | 50.94 | 101.71 | 0.40000 | 1.02 |
| 1.30705 | 3.20 | 72.21879 | 71.02 | 97.84 | 0.64000 | 1.37 |
| 1.27367 | 2.54 | 74.42506 | 56.25 | 93.68 | 0.24000 | 0.67 |
| 1.23314 | 3.73 | 77.31282 | 82.74 | 91.67 | 0.40000 | 2.27 |

Philips Analytical

Page: 1

FIG. 11A

Composition analysis of manganese silicate (synthesized at neutral (pH 6-7) reaction conditions) using EDAX attached to SEM (Scanning Electron Microscope).

Weight % by Element

| Filenames | o k | NaK | Sik | ClK | MnK |
|---|---|---|---|---|---|
| Manganese-o | 142.30 | 1.03 | 19.11 | 0.43 | 37.14 |

Atomic % by Element

| Filenames | o k | NaK | Sik | ClK | MnK |
|---|---|---|---|---|---|
| Manganese-o | 165.17 | 1.10 | 16.77 | 0.30 | 16.66 |

ESR (Electron spin resonance) spectrometer analysis of manganese silicate (synthesized at neutral (pH 6-7) reaction conditions).

XRD (X-ray diffraction) pattern of manganese silicate (synthesized at neutral (pH 6-7) reaction conditions).

FIG. 11D

XRD (X-ray diffraction) pattern of manganese silicate (synthesized at neutral (pH 6-7) reaction conditions).

X'Pert Graphics & Identify  
(searched) peak list: MO-R 2

User-1  
2/3/03 11:50

Original scan: MO-R  
Description of scan:

Date: 2/2/03 16:35

Used wavelength: K-Alpha1

K-Alpha1 wavelength (Å): 1.54056  
K-Alpha2 wavelength (Å): 1.54439  
K-Alpha2/K-Alpha1 intensity ratio: 0.50000  
K-Alpha wavelength (Å): 1.54056  
K-Beta wavelength (Å): 1.39222

Peak search parameter set: As Measured Intensities  
Set created: 1/8/03 13:03  
Peak positions defined by: Minimum of 2nd derivative  
Minimum peak tip width (°2Theta): 0.00  
Minimum peak tip width (°2Theta): 1.00  
Peak base width (°2Theta): 2.00  
Minimum significance: 0.60

| d-spacing (Å) | Relative Intensity (%) | Angle (°2Theta) | Peak Height (counts/s) | Background (counts/s) | Tip Width (°2Theta) | Significance |
|---|---|---|---|---|---|---|
| 3.70419 | 29.83 | 24.00430 | 44.16 | 278.06 | 0.64000 | 0.71 |
| 2.91440 | 100.00 | 30.65087 | 148.04 | 264.37 | 0.20000 | 0.63 |
| 2.20663 | 25.19 | 40.86153 | 37.29 | 162.18 | 0.48000 | 0.69 |
| 2.02880 | 29.18 | 44.62686 | 43.19 | 140.28 | 0.48000 | 0.68 |
| 1.79758 | 23.71 | 50.74610 | 35.10 | 133.23 | 0.48000 | 0.61 |

Philips Analytical

FIG. 12A

Composition analysis of manganese silicate (synthesized at extreme acidic (below pH 2) reaction conditions) using EDAX attached to SEM (Scanning Electron Microscope).

Weight % by Element

| Filenames | o k | NaK | Sik | ClK | MnK |
|---|---|---|---|---|---|
| manganese-ne | 34.04 | 0.82 | 30.75 | 0.75 | 33.64 |

Atomic % by Element

| Filenames | o k | NaK | Sik | ClK | MnK |
|---|---|---|---|---|---|
| manganese-ne | 54.67 | 0.92 | 28.13 | 0.54 | 15.73 |

ESR (Electron spin resonance) spectrometer analysis of manganese silicate (synthesized at extreme acidic (below pH 2) reaction conditions).

XRD (X-ray diffraction) pattern of manganese silicate (synthesized at extreme acidic (below pH 2) reaction conditions).

FIG. 12D

XRD (X-ray diffraction) pattern of manganese silicate (synthesized at extreme acidic (below pH 2) reaction conditions).

| X'Pert Graphics & Identify (searched) peak list: MN-R 2 | | User-1 2/3/03 11:51 |
|---|---|---|

Original scan: MN-R  
Description of scan:  
Date: 2/2/03 17:01

Used wavelength: K-Alpha1

K-Alpha1 wavelength (Å): 1.54056  
K-Alpha2 wavelength (Å): 1.54439  
K-Alpha2/K-Alpha1 intensity ratio : 0.50000  
K-Alpha wavelength (Å): 1.54056  
K-Beta wavelength (Å): 1.39222

Peak search parameter set: As Measured Intensities  
Set created: 1/8/03 13:03  
Peak positions defined by: Minimum of 2nd derivative  
Minimum peak tip width (°2Theta): 0.00  
Minimum peak tip width (°2Theta): 1.00  
Peak base width (°2Theta): 2.00  
Minimum significance: 0.60

| d-spacing (Å) | Relative Intensity (%) | Angle (°2Theta) | Peak Height (counts/s) | Background (counts/s) | Tip Width (°2Theta) | Significance |
|---|---|---|---|---|---|---|
| 3.60774 | 100.00 | 24.65599 | 32.88 | 359.03 | 0.96000 | 0.77 |

FIG. 13A

Composition analysis of zirconium silicate (synthesized at neutral (pH 6-7) reaction conditions) using EDAX attached to SEM (Scanning Electron Microscope).

Weight % by Element

| Filenames | o k | Sik | ZrL |
|---|---|---|---|
| Zircon99.spc | 39.00 | 14.78 | 46.22 |

Atomic % by Element

| Filenames | o k | Sik | ZrL |
|---|---|---|---|
| Zircon99.spc | 70.23 | 15.17 | 14.60 |

ESR (Electron spin resonance) spectrometer analysis of zirconium silicate (synthesized at neutral (pH 6-7) reaction conditions).

XRD (X-ray diffraction) pattern of zirconium silicate (synthesized at neutral (pH 6-7) reaction conditions).

FIG. 14A

Composition analysis of zirconium silicate (synthesized at extreme acidic (below pH 2) reaction conditions using EDAX attached to SEM (Scanning Electron Microscope).

Weight % by Element

| Filenames | o k | NaK | Sik | ZrL | ClK |
|---|---|---|---|---|---|
| Zircon55.spc | 51.43 | 0.95 | 26.86 | 20.76 | 0.00 |

Atomic % by Element

| Filenames | o k | NaK | Sik | ZrL | ClK |
|---|---|---|---|---|---|
| Zircon55.spc | 72.40 | 0.93 | 21.54 | 5.13 | 0.00 |

ESR (Electron spin resonance) spectrometer analysis of zirconium silicate (synthesized at extreme acidic (below pH 2) reaction conditions).

XRD (X-ray diffraction) pattern of zirconium silicate (synthesized at extreme acidic (below pH 2) reaction conditions).

FIG. 14D

XRD (X-ray diffraction) pattern of zirconium silicate (synthesized at extreme acidic (below pH 2) reaction conditions).

| X'Pert Graphics & Identify | | User-1 |
|---|---|---|
| (searched) peak list: SS 2 | | 2/22/03 13:12 |

| Original scan: 55 | Date: 2/22/03 11:31 |
|---|---|
| Description of scan: | |

| Used wavelength: | K-Alpha1 |
|---|---|
| K-Alpha1 wavelength (Å): | 1.54056 |
| K-Alpha2 wavelength (Å): | 1.54439 |
| K-Alpha2/K-Alpha1 intensity ratio : | 0.50000 |
| K-Alpha wavelength (Å): | 1.54056 |
| K-Beta wavelength (Å): | 1.39222 |

| Peak search parameter set: | As Measured Intensities |
|---|---|
| Set created: | 1/8/03 13:03 |
| Peak positions defined by: | Minimum of 2nd derivative |
| Minimum peak tip width (°2Theta): | 0.00 |
| Minimum peak tip width (°2Theta): | 1.00 |
| Peak base width (°2Theta): | 2.00 |
| Minimum significance: | 0.60 |

| d-spacing (Å) | Relative Intensity (%) | Angle (°2Theta) | Peak Height (counts/s) | Background (counts/s) | Tip Width (°2Theta) | Significance |
|---|---|---|---|---|---|---|
| 8.11438 | 100.00 | 10.89433 | 84.80 | 578.00 | 0.80000 | 0.69 |

FUNCTIONAL TRANSITION METAL SILICATES

This application is the National Stage under 35 USC §371 of International Application Number PCT/IB2003/002011 filed on May 15, 2003.

FIELD OF THE INVENTION

The present invention in general relates to the field of functional transition metal silicates. In particular, the present invention relates to synthesis of functional transition metal silicates (FTMS) with required structural composition for the targeted activities.

This invention more particularly relates to synthesis of functional transition metal silicates such as silver silicate, cupric silicate, zinc silicate, manganese silicate and zirconium silicate, having structural composition for effective decontamination, disinfection and microbicidal properties.

This invention also relates to immobilization of functional transition metal silicates (such as silver silicate, cupric silicate, zinc silicate, manganese silicate and zirconium silicate) on activated alumina, aluminium oxide, agropolymers, cellulose, quartz sand, silica gel, incorporating into resins and functional transition metal silicate containing resin coating on solid matrix like quartz sand for effective decontamination, disinfection, microbicidal and toxic gas detoxification properties.

These functional transition metal silicates are useful as decontaminants (by sequestering metals, chemicals, and pesticides from aqueous medium), as disinfectants (by removing microbes such as bacteria, fungi and viruses from aqueous medium), and as microbicides (to kill fungal, bacterial etc., pests, and as protective seed coat treatments), as anti microbial active ingredients in detergents, cleaning solutions and toxic gas detoxificants.

These functional transition metal silicates have many applications, which are useful in manufacturing of effective catalysts and anti-microbial paints etc.

BACKGROUND OF THE INVENTION

Extensive work is being carried out on zeolites and alkaline earth metal silicates compared to transition metal silicates.

In relation to transition metal silicates use for decontamination, Dodwell et al (U.S. Pat. No. 5,053,139, 1991) prepared transition metal silicates such as titanium and tin silicates, comprising cation exchangers, to remove heavy metals such as lead, cadmium, zinc, chromium and arsenic. When these metal silicates were failed to reduce the metal pollutant concentration, these metal silicates comprising with cation exchangers were prepared to reduce the metal pollutant concentration to required level. Although in patent claims, it was not mentioned about zirconium silicate (U.S. Pat. No. 5,053, 139, 1991) but in the description (example 14) it was mentioned about zirconium silicate preparation along with cation exchanger, and the failure of zirconium silicate ion exchanger to reduce metal pollutant concentration in treated water.

It was observed that tin and titanium silicates failed to decontaminate coliform bacteria in drinking water when they were tested in our laboratory.

In the transition metals, anti-microbial metals such as silver, copper, zinc and manganese were well known and silicates of these metals were not studied in detail for the relation between function (such as decontamination, disinfection and microbicidal properties) and structural composition.

Copper silicates were known from 1936 (GB 442664) for agricultural or horticultural pest control and these copper silicates were synthesized by heating an aqueous suspension of finely divided hydrated silica with substantially insoluble basic copper compounds in alkaline conditions at high temperature.

The synthesis of various types of copper silicates based on the functional property was not studied among these reports or observations.

Many copper salts were formulated for use as agricultural pesticides and copper silicates do not gain much importance among them. Copper alumino silicates were mixed with antibiotics to obtain synergism between copper compounds and antibiotics (GB 788668).

Present invention is aimed to synthesize functional transition metal silicates of the required structural composition for targeted activities such as decontamination, disinfection and microbicidal properties etc. Another objective of the present invention is to invent novel immobilized functional transition metal silicates.

OBJECTS OF THE INVENTION

Accordingly it is the primary object of the invention is to invent functional transition metal silicates by synthesizing of the required structural composition for the targeted activities.

Another objective of invention is to invent functional transition metal silicates suitable for effective disinfection of microbes such as bacteria, fungi and viruses.

It is also the object of the invention is to invent transition metal silicates suitable for effective decontamination of metals, chemical pollutants, and pesticides from aqueous systems.

Another objective of the invention is to invent functional transition metal silicates having microbicidal property for their usage as pesticides.

Another objective of invention is to develop functional transition metal silicates that are useful in mixing with seed coat treatments, paints, detergents, cleaning solutions, and zeolites.

Another object of the invention is to invent immobilized functional transition metal silicates, which are suitable to use in column mode as decontaminants (by sequestering metals, chemicals, and pesticides from aqueous medium), as disinfectants (by removing microbes such as bacteria, fungi and viruses from aqueous medium), and as microbicides (to kill fungal, bacterial etc., pests, and as protective seed coat treatments), as antimicrobial active ingredients in detergents, cleaning solutions and toxic gas detoxificants.

Another objective of the invention is to develop method for producing immobilized functional transition metal silicates by incorporating into resins, which are suitable for column mode decontaminants (by sequestering metals, chemicals, and pesticides from aqueous medium) as disinfectants (by removing microbes such as bacteria, fungi and viruses from aqueous medium), and as microbicides (to kill fungal, bacterial etc., pests, and as protective seed coat treatments), as antimicrobial active ingredients in detergents, cleaning solutions and toxic gas detoxificants.

Yet another objective of the present invention is to develop immobilized functional transition metal silicates by coating transition metal silicate containing resins on quartz sand, which are suitable for column mode as decontaminants (by sequestering metals, chemicals, and pesticides from aqueous medium), as disinfectants (by removing microbes such as bacteria, fungi and viruses from aqueous medium), and as microbicides (to kill fungal, bacterial etc. pests, and as protective seed coat treatments), as antimicrobial active ingredients in detergents, cleaning solutions and toxic gas detoxificants.

SUMMARY OF THE INVENTION

To meet the above objects and others, the present invention provides novel functional transition metal silicates and immobilized functional transition metal silicates comprising required structural composition for targeted activities, and method of producing and utilizing these functional transition metal silicates for various purposes such as decontamination, disinfection, microbicidal, toxic gas detoxification from combustion, nicotine and tar detoxification from cigarette smoke etc. properties as defined in claims.

DETAILED DESCRIPTION OF THE INVENTION

Accordingly, the present invention provides a novel functional transition metal silicates (FTMS) selected from cupric silicate, silver silicate, manganese silicate, zinc silicate and zirconium silicate, said metal silicates being obtained by mixing salt solution of transition metal with a soluble alkaline silicate solution under desired pH, temperature and silicate to metal ratio and or by using immobilized form of functional transition metal silicates immobilized on materials selected from activated alumina, aluminium oxide, agropolymers, cellulose, quartz sand, silica gel, and functional transition metal silicates incorporated resins and functional transition metal silicate containing resin coating on solid matrix such as quartz sand to obtain varied silicate metal ratio along with suitable structural composition for achieving effective functional transition metal silicate materials such as decontaminants of metals, chemicals, pesticides, disinfectants of bacteria, fungus and viruses, microbicides of pathogens such as bacteria and fungus, detoxificants of carbon monoxide, sulphur dioxide, NOX (oxides of nitrogen), hydrocarbons, tobacco tar, and nicotine etc.

More particularly, the present invention provides a novel functional transitional metal silicate selected from cupric silicate, silver silicate, manganese silicate, zinc silicate and zirconium silicate, said metal silicates being obtained by mixing salt solution of chloride, nitrates or sulphates of the corresponding transitional metals, with a soluble alkaline silicate solution under desired pH, temperature and silicate to metal ratio to form a precipitate, followed by washing and drying the precipitate to obtain the transition metal silicates varied silicate to metal ratio along with suitable structural composition, said transitional metal silicates exhibiting functions selected from decontamination, disinfection, microbicidal, detoxificant and anti-microbial.

IN an embodiment of the present invention, there is provided a functional transition metal silicate (FTMS) effective as a decontaminant, a disinfectant, a detoxificant, a protectant, a microbicide or combination thereof, comprising a ratio of transition metal to silica in the transition metal silicate in a predetermined range and a structural composition for said effectiveness, said FTMS being capable of being immobilized on a suitable materials or incorporating into resins and/or coating along with resins on suitable materials.

In another embodiment of the present invention, wherein a transition metal, wherein said ratio of transition metal to silica in the transition metal silicate is in a range of about 0.34 to about 19.57.

In yet another embodiment of the present invention, wherein a transition metal, comprising variable functions even with similar transition metal silicate ratio based on structural composition having specific ESR(g) values and specific XRD pattern obtained by varied reaction conditions.

In still another embodiment of the present invention, wherein the varied reaction conditions as claimed are varied pH conditions during a process for preparing the transitional metal silicates including extreme acidic to 12 PH, reactant concentrations: silicate content in soluble alkaline silicate solution and ratio of transition metal salt solution to soluble alkaline silicate solution, varied temperature maintained between 20 to 95 degrees centigrade, and combinations thereof.

In one more embodiment of the present invention, wherein the transition metal silicate is selected from the group consisting of cupric silicate, silver silicate, manganese silicate, zinc silicate, zirconium silicate and combination thereof.

In one another embodiment of the present invention, wherein the transition metal silicate is effective as a decontiminant of metals, chemicals, pesticides, microbes or combination thereof.

In a further embodiment of the present invention, wherein the transition metal silicate is effective as a disinfectant of a bacteria, a fungus, a virus, a microbicide of a pathogen or combinations thereof.

In a further more embodiment of the present invention, wherein the transition metal silicate is effective as a detoxificant of carbon monoxide, sulphur dioxide, an oxide of nitrogen, a hydrocarbon, tobacco tar, nicotine or toxic gases or chemical conversion of toxic gases and/or toxic chemical containing gases into non-toxic form, or combinations thereof.

In an embodiment of the present invention, wherein the metals are arsenic, mercury, lead, toxic metals or combinations thereof.

In another embodiment of the present invention, wherein the bacteria is a coliform bacteria, a Gram positive, a Gram negative bacteria or combinations thereof.

In yet another embodiment of the present invention, wherein the fungus is pathogenic fungi such as *Sclerotium rolfsii, Rhizoctonia solani, Fusarium oxysporium, Pyricularia oryzae* or combinations thereof.

In still another embodiment of the present invention, wherein the virus is having infective in nature.

In one more embodiment of the present invention, wherein the transition metal silicate is prepared by a method comprising:
(a) adding a solution of the transition metal to a soluble alkali silicate solution to form a mixture;
(b) adjusting pH and/or temperature of the mixture;
(c) forming a precipitate comprising the transition metal silicate;
(d) washing and drying the precipitate to obtain the transitional metal silicate.

In one another embodiment, the present invention provides a composition comprising a transition metal silicate immobilized on a substance, the transition metal silicate comprising a transition metal, wherein a ratio of transition metal to silica in the transition metal silicate is in a range of about 0.34 to about 19.57 and/or with a functional structure and the transition metal silicate is effective as a decontaminant, a disinfectant, a detoxificant or microbicide or combination thereof.

In a further embodiment of the present invention, wherein the substance is selected from a group consisting of an agropolymer, activated alumina, aluminium oxide, cellulose, vinyl ester resin, a bisphenol resin, an isopthalic food grade resin, quartz sand, silica gel and combinations thereof.

In a further more embodiment, the present invention provides a composition comprising a transition metal silicate incorporated in a substance, the transition metal silicate comprising a transition metal, wherein a ratio of transition metal to silica in the transition metal silicate is in a range of about 0.34 to about 19.57 and/or with functional structure and the transition metal silicate is effective as a decontaminant, a disinfectant, a detoxificant or microbicide or combination thereof.

In an embodiment of the present invention, wherein the substance is a resin.

In another embodiment of the present invention, wherein the resin is selected from a group consisting of a vinyl ester resin, a bisphenol resin, a isopthalic food grade resin and combinations thereof.

In yet another embodiment, the present invention provides a composition for a coating comprising a transition metal silicate comprising a transition metal, wherein a ratio of transition metal to silica in the transition metal silicate is in a range of about 0.34 to about 19.57 and/or with a functional structure and the transition metal silicate is effective as a decontaminant, a disinfectant, a detoxificant, a microbicide or combination thereof.

In still another embodiment of the present invention, wherein the coating further comprises a resin and a solid material.

In one more embodiment of the present invention, wherein the transition metal silicate is selected from the group consisting of cupric silicate, silver silicate, manganese silicate, zinc silicate, zirconium silicate and combination thereof.

In one another embodiment of the present invention, wherein the transition metal silicate is effective as a decontiminant of a metal, a chemical, a pesticide or microbe or combination thereof.

In a further embodiment of the present invention, wherein the transition metal silicate is effective as a disinfectant of a bacteria, a fungus, a virus, a microbe of a pathogen or combinations thereof.

In a further more embodiment of the present invention, wherein the transition metal silicate is effective as a detoxificant of toxic gases and/or toxic chemicals in gaseous forms such as carbon monoxide, sulphur dioxide, an oxide of nitrogen, a hydrocarbon, tobacco tar, nicotine or conversion of toxic gases to non-toxic gases or combinations thereof.

In an embodiment of the present invention, wherein when the functional transition metal silicate is a cupric silicate which is synthesized by mixing 100 ml of 0.5 gm/ml transition metal salt solution and 10 ml of sodium silicate solution having sodium and silica in the ratio 1:2 under acidic pH conditions have the following characteristic:

Silica:transition metal ratio as=1:5.15 (compositional analysis for silica/transition metal ratio)

Electron Spin Resonance ESR (g values)=A) 4.32481 B) 2.55205 C) 2.31749 D) 2.08807 E) 2.04673

X-ray diffraction analysis give XRD significant peak height (counts/s) and angle ° 2 theta=1) 2128.25 and 16.28197
  2) 1593.74 and 32.29018
  3) 1470.73 and 39.79307

In another embodiment of the present invention, wherein when the functional transition metal silicate is a cupric silicate which is synthesized by mixing 100 ml of 0.5 gm/ml transition metal salt solution and 50 ml sodium silicate solution having sodium and silica in the ratio 1:1 at temperature in the range of 70° C. to 90° C. under acidic pH conditions have the following characteristic:

Silica:transition metal ratio as=1:0.78 (compositional analysis for silica/transition metal ratio)

Electron Spin Resonance ESR (g values)=A) 2.23480 B) 2.06456

X-ray diffraction analysis give XRD significant peak height (counts/s) and angle ° 2 theta=1) 835.63 and 16.20057
  2) 706.74 and 32.23910
  3) 502.52 and 39.57159

In yet another embodiment of the present invention, wherein when the functional transition metal silicate is a cupric silicate which is synthesized by mixing 100 ml of 0.5 gm/ml transition metal salt solution and desired amount of sodium silicate solution having sodium and silica in the ratio 1:1 under neutral pH conditions have the following characteristic:

Silica:transition metal ratio as=1:1 (compositional analysis for silica/transition metal ratio)

Electron Spin Resonance ESR (g values)=A) 3.10383 B) 2.36522 C) 2.0467 D) 1.21887 E) 0.96688

X-ray diffraction analysis give XRD significant peak height (counts/s) and angle ° 2 theta=1) 940.91 and 16.19577
  2) 764.43 and 32.29276
  3) 694.85 and 39.77809

In one more embodiment of the present invention, wherein when the functional transition metal silicate is a cupric silicate which is synthesized by mixing 100 ml of 0.5 gm/ml transition metal salt solution and desired amount of sodium silicate solution having sodium and silica in the ratio 1:1 under basic pH conditions have the following characteristic:

Silica:transition metal ratio as=1:0.8 (compositional analysis for silica/transition metal ratio)

Electron Spin Resonance ESR (g values)=A) 3.71806 B) 3.23001 C) 2.6168

X-ray diffraction analysis give XRD significant peak height (counts/s) and angle ° 2 theta=1) 152.74 and 26.64983

In one another embodiment of the present invention, wherein when the functional transition metal silicate is a cupric silicate which is synthesized by mixing 100 ml of 0.5 gm/ml transition metal salt solution, 10 ml of 36% HCl and 50 ml of sodium silicate solution having sodium and silica in the ratio 1:1 at temperature in the range of 70° C. to 90° C. and under extreme acidic pH conditions have the following characteristic:

Silica:transition metal ratio as=1:0.53 (compositional analysis for silica/transition metal ratio)

Electron Spin Resonance ESR (g values)=A) 2.18421 B) 2.06874 C) 1.21231

X-ray diffraction analysis give XRD significant peak height (counts/s) and Angle ° 2 theta=1) 400.70 and 16.19872
  2) 394.77 and 32.27956
  3) 330.02 and 39.71761

In a further embodiment of the present invention, wherein when the functional transition metal silicate is a cupric silicate which is synthesized by mixing 100 ml of 0.5 gm/ml transition metal salt solution, 20 ml of 36% HCl and 50 ml of sodium silicate solution having sodium and silica in the ratio 1:1 at temperature in the range of 70° C. to 90° C. and under extreme acidic pH conditions have the following characteristic:

Silica:transition metal ratio as=1:0.34 (compositional analysis for silica/transition metal ratio)

Electron Spin Resonance ESR (g values)=A) 2.15561 B) 2.03614

X-ray diffraction analysis give XRD significant peak height (counts/s) and Angle ° 2 theta=1) 541.23 and 16.26305
  2) 414.21 and 32.36589
  3) 365.45 and 39.85131

In an embodiment of the present invention, wherein when the functional transition metal silicate is a zinc silicate which is synthesized by mixing 100 ml of 0.5 gm/ml transition metal salt solution and desired quantity of sodium silicate solution having sodium and silica in the ratio 1:1 under neutral pH conditions have the following characteristic:

Silica:transition metal ratio as=1:12.13 (compositional analysis for silica/transition metal ratio)

Electron Spin Resonance ESR (g values)=A) 5.49809 B) 4.55342 C) 2.54593 D) 2.10091 E) 2.05499

X-ray diffraction analysis give XRD significant peak height (counts/s) and Angle ° 2 theta=1) 444.15 and 32.75904

2) 307.02 and 59.58455

3) 263.36 and 28.27636

In another embodiment of the present invention, wherein when the functional transition metal silicate is a zinc silicate which is synthesized by mixing 100 ml of 0.5 gm/ml transition metal salt solution, 10 ml of 36% HCl and 50 ml of sodium silicate solution having sodium and silica in the ratio 1:1 at temperature in the range of 70° C. to 90° C. and under extreme acidic pH conditions have the following characteristic:

Silica:transition metal ratio as=1:2.46 (compositional analysis for silica/transition metal ratio)

Electron Spin Resonance ESR (g values)=A) 4.38410 B) 4.01910 C) 2.53191 D) 1.87886 E) 2.01793

X-ray diffraction analysis give XRD significant peak height (counts/s) and Angle ° 2 theta=1) 2079.88 and 11.07467

2) 835.44 and 33.52527

3) 664.98 and 32.88120

In yet another embodiment of the present invention, wherein when the functional transition metal silicate is a silver silicate which is synthesized by mixing 100 ml of 0.5 gm/ml transition metal salt solution and desired amount of sodium silicate solution having sodium and silica in the ratio 1:2 under neutral pH conditions have the following characteristic:

Silica:transition metal ratio as=1:19.57 (compositional analysis for silica/transition metal ratio)

Electron Spin Resonance ESR (g values)=A) 4.36796 B) 2.37847 C) 3.95509 D) 2.04657

X-ray diffraction analysis give XRD significant peak height (counts/s) and Angle ° 2 theta=1) 3945.11 and 32.29885

2) 2421.27 and 46.27446

3) 1835.66 and 27.89129

In still another embodiment of the present invention, wherein when the functional transition metal silicate is a silver silicate which is synthesized by mixing 50 ml of 0.5 gm/ml transition metal salt solution, 8 ml of 69-70% $HNO_3$ and desired amount of sodium silicate solution having sodium and silica in the ratio 1:1 under acidic pH conditions (about 2 pH) have the following characteristic:

Silica:transition metal ratio as=1:1.04 (compositional analysis for silica/transition metal ratio)

Electron Spin Resonance ESR (g values)=A) 4.37171 B) 4.04714 C) 1.98189

X-ray diffraction analysis give XRD significant peak height (counts/s) and Angle ° 2 theta=1) 2217.87 and 29.33483

2) 684.55 and 47.68093

3) 674.27 and 42.31091

In one more embodiment of the present invention, wherein when the functional transition metal silicate is a manganese silicate which is synthesized by mixing 100 ml of 0.5 gm/ml transition metal salt solution and desired amount of sodium silicate solution having sodium and silica in the ratio 1:1 under neutral pH conditions have the following characteristic:

Silica:transition metal ratio as=1:1.94 (compositional analysis for silica/transition metal ratio)

Electron Spin Resonance ESR (g values)=A) 1.93412 B) 2.06655

X-ray diffraction analysis give XRD significant peak height (counts/s) and Angle ° 2 theta=1) 148.04 and 30.65087

In one another embodiment of the present invention, wherein when the functional transition metal silicate is a manganese silicate which is synthesized by mixing 100 ml of 0.5 gm/ml transition metal salt solution, 10 ml of 36% HCl and 50 ml of sodium silicate solution having sodium and silica in the ratio 1:1 at temperature in the range of 70° C. to 90° C. and under extreme acidic pH conditions have the following characteristic:

Silica:transition metal ratio as=1:1.09 (compositional analysis for silica/transition metal ratio)

Electron Spin Resonance ESR (g values)=A) 4.3463 B) 4.17458 C) 2.18228 D) 2.11243 E) 2.05491 F) 1.999661

X-ray diffraction analysis give XRD significant peak height (counts/s) and Angle ° 2 theta=1) 32.88 and 24.65599

In a further embodiment of the present invention, wherein when the functional transition metal silicate is a zirconium silicate which is synthesized by mixing 100 ml of 0.5 gm/ml transition metal salt solution and desired amount of sodium silicate solution having sodium and silica in the ratio 1:1 under neutral pH conditions have the following characteristic:

Silica:transition metal ratio as=1:2.90 (compositional analysis for silica/transition metal ratio)

Electron Spin Resonance ESR (g values)=A) 4.42797 B) 4.18272 C) 2.24547 D) 2.30425 E) 2.18961 F) 1.23086

In an embodiment of the present invention, wherein when the functional transition metal silicate is a zirconium silicate which is synthesized by mixing 100 ml of 0.5 gm/ml transition metal salt solution, 10 ml of 36% HCl and 50 ml of sodium silicate solution having sodium and silica in the ratio 1:1 at temperature in the range of 70° C. to 90° C. and under extreme acidic pH conditions have the following characteristic:

Silica:transition metal ratio as=1:0.77 (compositional analysis for silica/transition metal ratio)

Electron Spin Resonance ESR (g values)=A) 4.37236 B) 2.82039 C) 1.92596 D) 1.21652 E) 1.02930 F) 0.93795

X-ray diffraction analysis give XRD significant peak height (counts/s) and Angle ° 2 theta=1) 84.80 and 10.89433

The present invention also provides a functional transition metal silicates selected from cupric silicate, silver silicate, manganese silicate, zinc silicate and zirconium silicate, said metal silicates being obtained by mixing salt solution of chloride, nitrates or sulphates of the corresponding transitional metals, with a soluble alkaline silicate solution under desired pH, temperature and silicate to metal ratio to form a precipitate, followed by washing and drying the precipitate and having the structure as shown in FIGS. 1 to 14 of the accompanying drawings and said transitional metal silicates exhibiting functions selected from decontamination, disinfection, microbicidal and anti-microbial.

In an embodiment of the present invention, wherein the functional metal silicates are optionally loaded or coated on a substrate selected from activated alumina, aluminium oxide, agropolymers, cellulose, quartz sand, silica gel, and functional transition metal silicates incorporated resins and functional transition metal silicate containing resin coated on solid matrix selected from quartz sand.

The present invention also provides a method of decontaminating an aqueous medium containing sequestering metals, chemicals and pesticides, said method containing the step of contacting the aqueous medium with a novel functional transition metal silicates (FTMS) selected from cupric silicate, silver silicate, manganese silicate, zinc silicate and zirconium silicate optionally loaded or coated on a substrate in a container.

In an embodiment of the present invention, wherein the transitional metal silicates synthesized under acidic pH conditions and extremely acidic pH conditions provide better decontamination as compared to transitional metal silicates synthesized under basic and neutral pH conditions.

The present invention further provides a method of disinfecting an aqueous medium containing microbes, bacteria, fungi and viruses, said method containing the step of contacting the aqueous medium with a novel functional transition metal silicates (FTMS) selected from cupric silicate, silver silicate, manganese silicate, zinc silicate and zirconium silicate optionally loaded or coated on a substrate in a container.

In an embodiment of the present invention, wherein the transitional metal silicates synthesized under acidic pH conditions and extremely acidic pH conditions provide decontamination and disinfection of microbes.

In another embodiment of the present invention, wherein the transitional metal silicates synthesized provide protection and/or control of pathogenic viruses.

In yet another embodiment of the present invention, wherein the transitional metal silicates selected from cupric silicate, silver silicate, manganese silicate, zinc silicate and zirconium silicate optionally loaded or coated on a substrate in a container disinfect gram positive and gram negative bacteria, fungus, and viruses enabling the usage of these novel functional transition metal silicates in detergents, cleaning solutions, seed coat treatments, disinfectants, and shampoos etc., for protection against microbial infections.

The present invention further more provides a process for preparing novel functional transition metal silicates (FTMS), selected from cupric silicate, silver silicate, manganese silicate, zinc silicate and zirconium silicate, said process comprising the steps of:
(a) addition transition metal salt solution to a soluble alkali silicate solution;
(b) selecting pH conditions of reaction i.e., acidic, or neutral, or basic or extreme acidic conditions (by adding acid such as HCl or $HNO_3$ to reaction medium) to form a precipitate, and
(c) drying the resultant precipitate of functional transition metal silicate without any soluble substances after through washing with distilled or deionized water to obtain the functional transition metal silicates.

In an embodiment of the present invention, wherein the functional transition metal silicates having varied silicate metal ratio were synthesized and silicate or transition metal content enhancement or decrease in a functional transition metal silicates was done at suitable reaction conditions selected from acidic or neutral or basic or extreme acidic pH conditions and using varied concentration of reactants selected from soluble silica having different alkali to silica ratio.

In another embodiment of the present invention, wherein cupric silicate having the characteristic as given below is synthesized by mixing 100 ml of 0.5 gm/ml transition metal salt solution and 10 ml of sodium silicate solution having sodium and silica in the ratio 1:2 under acidic pH conditions.
Silica:transition metal ratio as=1:5.15 (compositional analysis for silica/transition metal ratio)
Electron Spin Resonance ESR (g values)=A) 4.32481 B) 2.55205 C) 2.31749 D) 2.08807 E) 2.04673
X-ray diffraction analysis give XRD significant peak height (counts/s) and angle ° 2 theta=1) 2128.25 and 16.28197
2) 1593.74 and 32.29018
3) 1470.73 and 39.79307

In yet another embodiment of the present invention, wherein a cupric silicate having the characteristics as given below is synthesized by mixing 100 ml of 0.5 gm/ml transition metal salt solution and 50 ml sodium silicate solution having sodium and silica in the ratio 1:1 at temperature in the range of 70° C. to 90° C. under acidic pH conditions.
Silica:transition metal ratio as=1:0.78 (compositional analysis for silica/transition metal ratio)
Electron Spin Resonance ESR (g values)=A) 2.23480 B) 2.06456
X-ray diffraction analysis give XRD significant peak height (counts/s) and angle ° 2 theta=1) 835.63 and 16.20057
2) 706.74 and 32.23910
3) 502.52 and 39.57159

In still another embodiment of the present invention, wherein a cupric silicate having the characteristics as given below synthesized by mixing 100 ml of 0.5 gm/ml transition metal salt solution and desired amount of sodium silicate solution having sodium and silica in the ratio 1:1 under neutral pH conditions.
Silica:transition metal ratio as=1:1 (compositional analysis for silica/transition metal ratio)
Electron Spin Resonance ESR (g values)=A) 3.10383 B) 2.36522 C) 2.0467 D) 1.21887 E) 0.96688
X-ray diffraction analysis give XRD significant peak height (counts/s) and angle ° 2 theta=1) 940.91 and 16.19577
2) 764.43 and 32.29276
3) 694.85 and 39.77809

In one more embodiment of the present invention, wherein cupric silicate having the characteristics as given below is synthesized by mixing 100 ml of 0.5 gm/ml transition metal salt solution and desired amount of sodium silicate solution having sodium and silica in the ratio 1:1 under basic pH conditions have the following characteristic:
Silica:transition metal ratio as=1:0.8 (compositional analysis for silica/transition metal ratio)
Electron Spin Resonance ESR (g values)=A) 3.71806 B) 3.23001 C) 2.6168
X-ray diffraction analysis give XRD significant peak height (counts/s) and angle ° 2 theta=1) 152.74 and 26.64983

In one another embodiment of the present invention, wherein cupric silicate having the characteristics as given below is synthesized by mixing 100 ml of 0.5 gm/ml transition metal salt solution, 10 ml of 36% HCl and 50 ml of sodium silicate solution having sodium and silica in the ratio 1:1 at temperature in the range of 70° C. to 90° C. and under extreme acidic pH condition.
Silica:transition metal ratio as=1:0.53 (compositional analysis for silica/transition metal ratio)
Electron Spin Resonance ESR (g values)=A) 2.18421 B) 2.06874 C) 1.21231
X-ray diffraction analysis give XRD significant peak height (counts/s) and Angle ° 2 theta=1) 400.70 and 16.19872
2) 394.77 and 32.27956
3) 330.02 and 39.71761

In a further embodiment of the present invention, wherein cupric silicate having the characteristics as given below is synthesized by mixing 100 ml of 0.5 gm/ml transition metal salt solution, 20 ml of 36% HCl and 50 ml of sodium silicate solution having sodium and silica in the ratio 1:1 at temperature in the range of 70° C. to 90° C. and under extreme acidic pH conditions.

Silica:transition metal ratio as=1:0.34 (compositional analysis for silica/transition metal ratio)

Electron Spin Resonance ESR (g values)=A) 2.15561 B) 2.03614

X-ray diffraction analysis give XRD significant peak height (counts/s) and Angle ° 2 theta=1) 541.23 and 16.26305

2) 414.21 and 32.36589

3) 365.45 and 39.85131

In a further more embodiment of the present invention, wherein zinc silicate having the characteristics as given below is synthesized by mixing 100 ml of 0.5 gm/ml transition metal salt solution and desired quantity of sodium silicate solution having sodium and silica in the ratio 1:1 under neutral pH conditions.

Silica:transition metal ratio as=1:12.13 (compositional analysis for silica/transition metal ratio)

Electron Spin Resonance ESR (g values)=A) 5.49809 B) 4.55342 C) 2.54593 D) 2.10091 E) 2.05499

X-ray diffraction analysis give XRD significant peak height (counts/s) and Angle ° 2 theta=1) 444.15 and 32.75904

2) 307.02 and 59.58455

3) 263.36 and 28.27636

In an embodiment of the present invention, wherein zinc silicate having the characteristics as given below is synthesized by mixing 100 ml of 0.5 gm/ml transition metal salt solution, 10 ml of 36% HCl and 50 ml of sodium silicate solution having sodium and silica in the ratio 1:1 at temperature in the range of 70° C. to 90° C. and under extreme acidic pH conditions have the following characteristic:

Silica:transition metal ratio as=1:2.46 (compositional analysis for silica/transition metal ratio)

Electron Spin Resonance ESR (g values)=A) 4.38410 B) 4.01910 C) 2.53191 D) 1.87886 E) 2.01793

X-ray diffraction analysis give XRD significant peak height (counts/s) and Angle ° 2 theta=1) 2079.88 and 11.07467

2) 835.44 and 33.52527

3) 664.98 and 32.88120

In another embodiment of the present invention, wherein silver silicate having the characteristics as given below is synthesized by mixing 100 ml of 0.5 gm/ml transition metal salt solution and desired amount of sodium silicate solution having sodium and silica in the ratio 1:2 under neutral pH conditions.

Silica:transition metal ratio as=1:19.57 (compositional analysis for silica/transition metal ratio)

Electron Spin Resonance ESR (g values)=A) 4.36796 B) 2.37847 C) 3.95509 D) 2.04657

X-ray diffraction analysis give XRD significant peak height (counts/s) and Angle ° 2 theta=1) 3945.11 and 32.29885

2) 2421.27 and 46.27446

3) 1835.66 and 27.89129

In yet another embodiment of the present invention, wherein silver silicate having the characteristics as given below is synthesized by mixing 50 ml of 0.5 gm/ml transition metal salt solution, 8 ml of 69-70% $HNO_3$ and desired amount of sodium silicate solution having sodium and silica in the ratio 1:1 under acidic pH conditions (about 2 pH).

Silica:transition metal ratio as=1:1.04 (compositional analysis for silica/transition metal ratio).

Electron Spin Resonance ESR (g values)=A) 4.37171 B) 4.04714 C) 1.98189

X-ray diffraction analysis give XRD significant peak height (counts/s) and Angle ° 2 theta=1) 2217.87 and 29.33483

2) 684.55 and 47.68093

3) 674.27 and 42.31091

In still another embodiment of the present invention, wherein magnesium silicate having the characteristics as given below is synthesized by mixing 100 ml of 0.5 gm/ml transition metal salt solution and desired amount of sodium silicate solution having sodium and silica in the ratio 1:1 under neutral pH conditions have the following characteristic:

Silica:transition metal ratio as=1:1.94 (compositional analysis for silica/transition metal ratio)

Electron Spin Resonance ESR (g values)=A) 1.93412 B) 2.06655

X-ray diffraction analysis give XRD significant peak height (counts/s) and Angle ° 2 theta=1) 148.04 and 30.65087

In one more embodiment of the present invention, wherein manganese silicate having the characteristics as given below is synthesized by mixing 100 ml of 0.5 gm/ml transition metal salt solution, 10 ml of 36% HCl and 50 ml of sodium silicate solution having sodium and silica in the ratio 1:1 at temperature in the range of 70° C. to 90° C. and under extreme acidic pH conditions have the following characteristic:

Silica:transition metal ratio as=1:1.09 (compositional analysis for silica/transition metal ratio)

Electron Spin Resonance ESR (g values)=A) 4.3463 B) 4.17458 C) 2.18228 D) 2.11243 E) 2.05491 F) 1.999661

X-ray diffraction analysis give XRD significant peak height (counts/s) and Angle ° 2 theta=1) 32.88 and 24.65599

In one another embodiment of the present invention, wherein zirconium silicate having the characteristics as given below is synthesized by mixing 100 ml of 0.5 gm/ml transition metal salt solution and desired amount of sodium silicate solution having sodium and silica in the ratio 1:1 under neutral pH conditions have the following characteristic:

Silica:transition metal ratio as=1:2.90 (compositional analysis for silica/transition metal ratio)

Electron Spin Resonance ESR (g values)=A) 4.42797 B) 4.18272 C) 2:24547 D) 2.30425 E) 2.18961 F) 1.23086

In a further embodiment of the present invention, wherein zirconium silicate having the characteristics as given below is synthesized by mixing 100 ml of 0.5 gm/ml transition metal salt solution, 10 ml of 36% HCl and 50 ml of sodium silicate solution having sodium and silica in the ratio 1:1 at temperature in the range of 70° C. to 90° C. and under extreme acidic pH conditions have the following characteristic:

Silica:transition metal ratio as=1:0.77 (compositional analysis for silica/transition metal ratio)

Electron Spin Resonance ESR (g values)=A) 4.37236 B) 2.82039 C) 1.92596 D) 1.21652 E) 1.02930 F) 0.93795

X-ray diffraction analysis give XRD significant peak height (counts/s) and Angle ° 2 theta=1) 84.80 and 10.89433

In a further more embodiment of the present invention, wherein functional transition metal silicates selected from cupric silicate, silver silicate, manganese silicate, zinc silicate and zirconium silicate are capable of decontaminate heavy metals such as arsenic, mercury, etc., thereby enabling them to use these novel functional transitional metal silicates to decontaminate aqueous media such as metal polluted drinking water, ground water, industrial pollutants and any other sources of metal pollution.

In an embodiment of the present invention, wherein functional transition metal silicates selected from cupric silicate, silver silicate, manganese silicate, zinc silicate and zirconium silicate decontaminate pollutant chemicals such as trihalomethanes, polychlorinated biphenyls, semi volatile organic compounds, volatile organic compounds, and phenols.

In another embodiment of the present invention, wherein functional transition metal silicates control plant pathogens such as *Sclerotium rolfsii, Rhizoctonia solani, Fusarium oxysporium, Pyricularia oryzae* and this property enables functional transition metal silicates usage as effective pesticides.

The present also provides a process for preparing immobilized functional transition metal silicates selected from cupric silicate, silver silicate, manganese silicate, zinc silicate and zirconium silicate immobilized on a substrate material selected from agropolymers, activated alumina, cellulose, aluminium oxide, quartz sand, silica gel and suitable for use in column or batch mode, said process comprising the steps of:
  (a) adding transition metal salt containing solution selected from chlorides or sulphates or nitrates to the substrate material selected from agropolymers, activated alumina, cellulose, aluminium oxide, quartz sand, silica gel;
  (b) mixing the transition metal salt solution loaded substrate material of step (a) with alkali silicate solution;
  (c) heating the mixture at 70° C. to 90° C. and allowing the same to settle for 10 to 14 hrs at room temperature, and
  (d) removing unbound or non-immobilized substances by extensive washing with distilled or deionized water to obtain the immobilized functional transition metal silicates.

In an embodiment of the present invention, wherein the amount of functional transition metal silicate immobilized on the substrate material varies based on initial concentration of transition metal salt, soluble silica, the reaction time, particle size of substrate material and type of substrate material, and mode of immobilization such as physical or chemical.

In another embodiment of the present invention, wherein the functional transition metal silicates are immobilized by physical or chemical means.

In yet another embodiment of the present invention, wherein the functional transitional metal silicates are immobilized upon a solid matrix like quartz sand which is suitable for column mode and batch mode decontamination by directly incorporating the functional transitional metal silicates into resins and coating the functional transition metal silicate containing resins on the quartz sand.

In still another embodiment of the present invention, wherein functional transition metal silicates selected from cupric silicate, silver silicate, manganese silicate, zinc silicate and zirconium silicate immobilized on materials selected from activated alumina, aluminium oxide, agropolymers, cellulose, quartz sand, silica gel, are capable of decontaminating metals such as arsenic, mercury, etc., and this property enables immobilized functional transition metal silicates utility to purify metal contaminated drinking water, ground water and any other metal polluted aqueous streams.

In one more embodiment of the present invention, wherein functional transition metal silicates selected from cupric silicate, silver silicate, manganese silicate, zinc silicate and zirconium silicate immobilized on materials selected from activated alumina, aluminium oxide, agropolymers, cellulose, quartz sand, silica gel, are capable of capable of disinfecting coliform bacteria, from water and this property enables immobilized functional transition metal silicate utility to purify water free of harmful microbes.

In one another embodiment of the present invention, wherein functional transition metal silicates selected from cupric silicate, silver silicate, manganese silicate, zinc silicate and zirconium silicate immobilized on agropolymers are capable of decontaminating protozoan, *Cryptosporidium parvum*, from water and this property enables the usage of immobilized functional transition metal silicates for protection and or control of protozoan infections.

In a further embodiment of the present invention, wherein functional transition metal silicates selected from cupric silicate, silver silicate, manganese silicate, zinc silicate and zirconium silicate immobilized on materials selected from activated alumina, aluminium oxide, agropolymers, cellulose, quartz sand, silica gel, are capable of decontaminating polio viruses, rota viruses from water and this property enables their usage of immobilized functional transition metal silicates for protection and or control of pathogenic viruses infections.

The present invention further provides a process for preparing functional transition metal silicates selected from cupric silicate, silver silicate, manganese silicate, zinc silicate and zirconium silicate containing resins, for use as decontaminants by sequestering metals, chemicals, and pesticides from aqueous medium, disinfectants by removing microbes such as bacteria, fungi and viruses from aqueous medium, microbicides by killing fungus, bacteria etc., protective seed coat, insect/pest repellent, anti microbe active ingredients in detergents, cleaning solutions and detoxificants of toxic gas, nicotine and tar in column and batch mode, said process comprising the steps of:
  (a) adding 5 to 20% by wt. of the functional transition metal silicates to the resins selected from vinyl ester, bisphenol, isopthalic resins;
  (b) drying the mixture of step (a) by heating at 70° C. to 90° C. without addition of catalysts or accelerators, and
  (c) grinding the resultant material to required size.

In an embodiment of the present invention, wherein functional transition metal silicates selected from cupric silicate, silver silicate, manganese silicate, zinc silicate and zirconium silicate incorporated into resins selected from vinyl ester, bisphenol, isopthalic resins, are capable of decontaminating metals such as arsenic, mercury, etc., and this property enables immobilized functional transition metal silicates utility to purify metal contaminated drinking water, ground water and any other metal polluted aqueous streams functional transition metal silicate containing resin coated sand In another embodiment of the present invention, wherein functional transition metal silicates selected from cupric silicate, silver silicate, manganese silicate, zinc silicate and zirconium silicate incorporated into resins selected from vinyl ester, bisphenol, isopthalic resins, are capable of disinfecting coliform bacteria, from water and this property enables immobilized functional transition metal silicate utility to purify water free of harmful microbes.

The present invention provides a process for preparing solid substances such as quartz sand, suitable for use as decontaminants by sequestering metals, chemicals, and pesticides from aqueous medium, as disinfectants by removing microbes such as bacteria, fungi and viruses from aqueous medium, as microbicides by killing fungus, bacteria, pests etc., as seed protectant, as anti microbial active ingredients in detergents, cleaning solutions and detoxificants of toxic gas, nicotine and tar etc., coated with resins selected from vinyl ester, bisphenol, isopthalic resins containing functional transition metal silicates selected from cupric silicate, silver silicate, manganese silicate, zinc silicate and zirconium silicate said process comprising the steps of:
  (i) adding the functional transition metal silicates to the resins in the w/v ratio ranging from 0.5:1 to 4:1;
  (ii) mixing thoroughly the functional transition metal silicate containing resin of step (i) with solid matrix selected from quartz sand having size from 50-1000 microns at v/v ratio ranging from 1:5 to 1:50, and (iii) drying the resin-coated sand of step (ii) without addition of any catalyst or accelerators at 70° C. to 90° C. or by keeping at room temperature for a week to obtain the functional transition metal silicate coated solid substance.

In an embodiment of the present invention, wherein functional transition metal silicates selected from cupric silicate, silver silicate, manganese silicate, zinc silicate and zirconium silicate coated on sand is capable of decontaminating metals such as arsenic, mercury, etc., and this property enables immobilized functional transition metal silicates utility to purify metal contaminated drinking water, ground water and any other metal polluted aqueous streams.

In another embodiment of the present invention, wherein functional transition metal silicates selected from cupric silicate, silver silicate, manganese silicate, zinc silicate and zirconium silicate coated on sand is capable of disinfecting coliform bacteria, from water and this property enables immobilized functional transition metal silicate utility to purify water free of harmful microbes.

In yet another embodiment of the present invention, wherein the functional transition metal silicates selected from cupric silicate, silver silicate, manganese silicate, zinc silicate and zirconium silicate immobilized on materials selected from activated alumina, aluminium oxide, agropolymers, cellulose, quartz sand, silica gel, or functional transition metal silicates incorporated into resins or sand coated with functional transition metal silicates containing resin are capable of detoxifying toxic gases such as carbon monoxide, sulphur dioxide, nitrous oxide and hydrocarbons from combustion gases and this property enables these immobilized functional transition metal silicate containing filters usage as toxic air purifiers.

In still another embodiment of the present invention, wherein the functional transition metal silicates selected from cupric silicate, silver silicate, manganese silicate, zinc silicate and zirconium silicate immobilized on materials selected from activated alumina, aluminium oxide, agropolymers, cellulose, quartz sand, silica gel, or functional transition metal silicates incorporated into resins or sand coated with functional transition metal silicates containing resin are capable of detoxifying cigarette smoke by significantly reducing carbon monoxide, sulphur dioxide, nitrous oxide hydrocarbons, tar and nicotine and this property enables these immobilized functional transition metal silicate containing filters usage as toxic air and chemical purifiers and/or chemical conversion of toxic gases to non-toxic gases.

In one more embodiment of the present invention, wherein the functional transition metal silicates selected from cupric silicate, silver silicate, manganese silicate, zinc silicate and zirconium silicate immobilized on materials selected from activated alumina, aluminium oxide, agropolymers, cellulose, quartz sand, silica gel, or functional transition metal silicates incorporated into resins or sand coated with functional transition metal silicates containing resin are capable of decontaminating pesticides selected from chlorinated hydrocarbons such as endosulphan, synthetic pyrethroides such as cypermethrin, organophosphates such as chloripyriphos and this property enables these immobilized functional transition metal silicates as decontaminants of pesticides.

In one another embodiment of the present invention, wherein the functional transition metal silicates selected from cupric silicate, silver silicate, manganese silicate, zinc silicate and zirconium silicate immobilized on materials selected from activated alumina, aluminium oxide, agropolymers, cellulose, quartz sand, silica gel, or functional transition metal silicates incorporated into resins or sand coated with functional transition metal silicates containing resin are capable of decontaminating proteins from an aqueous medium enabling their usage to remove or decontaminate proteins from waste waters generating from bioprocess industry, to prevent undesirable protein contamination.

In a further embodiment of the present invention, wherein the functional transition metal silicates selected from cupric silicate, silver silicate, manganese silicate, zinc silicate and zirconium silicate immobilized on materials selected from activated alumina, aluminium oxide, agropolymers, cellulose, quartz sand, silica gel, or functional transition metal silicates incorporated into resins or sand coated with functional transition metal silicates containing resin are capable of decontaminating fungus from water and this property enables the usage of immobilized functional transition metal silicates for protection and or control of fungal infections.

In further more embodiment of the present invention, wherein the functional transition metal silicates selected from cupric silicate, silver silicate, manganese silicate, zinc silicate and zirconium silicate immobilized on materials selected from activated alumina, aluminium oxide, agropolymers, cellulose, quartz sand, silica gel, or functional transition metal silicates incorporated into resins or sand coated with functional transition metal silicates containing resin are capable of decontaminating trihalomethanes selected from chloroform, 1,1,1, trichloroethane, tetrachloroethylene, trichloroethylene, bromodichloroethane, dibromochloroethane, tetrachloroethylene, bromoform and 1,2, dichloro-3-bromopropane.

In an embodiment of the present invention, wherein the functional transition metal silicates selected from cupric silicate, silver silicate, manganese silicate, zinc silicate and zirconium silicate immobilized on materials selected from activated alumina, aluminium oxide, agropolymers, cellulose, quartz sand, silica gel, or functional transition metal silicates incorporated into resins or sand coated with functional transition metal silicates containing resin are capable of decontaminating Polychlorinated biphenyls selected from 2,3-dichlorobiphenyl, trichlorobiphenyl, tetrachlorobiphenyl, pentachlorobiphenyl, hexachlorobiphenyl, heptachlorobiphenyl and octachlorobiphenyl.

In another embodiment of the present invention, wherein the functional transition metal silicates selected from cupric silicate, silver silicate, manganese silicate, zinc silicate and zirconium silicate immobilized on materials selected from activated alumina, aluminium oxide, agropolymers, cellulose, quartz sand, silica gel, or functional transition metal silicates incorporated into resins or sand coated with functional transition metal silicates containing resin are capable of decontaminating volatile organic compounds selected from 1,1,1, trichloroethane; 1,1,2-trichloroethane; 1,3-dichloropropane; dibromochloromethane; ethane 1,2 dibromo; chlorobenzene; benzene 1,2-dimethyl; benzene 1,3-dimethyl; orthoxylene; benzene 1-methylethyl; ethane 1,1,2,2-tetrachloro; bromobenzene; 2-chloro toluene; benzene, propyl; benzene, 1chloro 4-methyl; benzene 1,2,3-trimethyl; 4-iso propyl toluene; benzene 1,2-diethyl; benzene 1,2-dichloro; 1,3-dichlorobenzene; 1,4-dichlorobenzene; toluene; n-butylbenzene; 1,2-dibromo 3-chloropropane; 1,2,4-trichlorobenzene; naphthalene; benzene 1,2,3-trichloro; benzene 1,3,5-trichloro; benzene 1,3,4-trichloro; 1,3-butadiene1,1,2,3,4; benzene 2-bromo 1,3,5; nitrobenzene; styrene; benzylbenzoate; 1,2,3,4-tetramethylbenzene; benzene 1-chloro 2-propyl and 4-bromo 3-chloroanilene.

In yet another embodiment of the present invention, wherein the functional transition metal silicates selected from cupric silicate, silver silicate, manganese silicate, zinc silicate and zirconium silicate immobilized on materials selected from activated alumina, aluminium oxide, agropolymers, cellulose, quartz sand, silica gel, or functional transition metal silicates incorporated into resins or sand coated with functional transition metal silicates containing resin are capable of decontaminating semi volatile organic compounds (such as benzene, 1,4-dichloro; ethane hexachloro; benzene 1,2,3, trichloro; 1,3 butadiene, 1,1,2,3,4; naphthalene, 2-chloro; acenephthylene; acenapthene; phenol, 2,4-bis(1,1-imet); diethyl phthalate; fluorene; benzene1-chloro-3phenol; diphenylamine; 4-bromophenyl-phenylether; benzene, hexachloro; phenantherene; anthracene; dibutyl phthalate; fluoranthene; pyrene; benzyl butyl phthalate; chrysene; bis (2-ethylhexy)phthalate; phenol, 2,3,4,5-tetrabrom; di-n-octyl phthalate; benzo(b)fluoranthene; benzo(k)fluoranthene; benzo(a)pyrene; indeno(1,2,3-cd)pyrene; dibenzo(a,h)anthracene and benzo(g,h,l)perylene.

In still another embodiment of the present invention, wherein the functional transition metal silicates selected from cupric silicate, silver silicate, manganese silicate, zinc silicate and zirconium silicate immobilized on materials selected from activated alumina, aluminium oxide, agropolymers, cellulose, quartz sand, silica gel, or functional transition metal silicates incorporated into resins or sand coated with functional transition metal silicates containing resin are capable of decontaminating phenols (such as benzoic acid; 2,4,5-trichlorophenol; 3-nitroaniline; 3-nitrophenol; 4-nitrophenol; 2,4-dinitrophenol; 4-nitroaniline and pentachlorophenol.

In one more embodiment of the present invention, wherein the functional transition metal silicates selected from cupric silicate, silver silicate, manganese silicate, zinc silicate and zirconium silicate immobilized on materials selected from activated alumina, aluminium oxide, agropolymers, cellulose, quartz sand, silica gel, or functional transition metal silicates incorporated into resins or sand coated with functional transition metal silicates containing resin have utility of decontamination and disinfection in high temperature zones such as boilers etc., due to thermo stability of this material.

In one another embodiment of the present invention, wherein the functional transition metal silicates selected from cupric silicate, silver silicate, manganese silicate, zinc silicate and zirconium silicate immobilized on materials selected from activated alumina, aluminium oxide, agropolymers, cellulose, quartz sand, silica gel, or functional transition metal silicates incorporated into resins or sand coated with functional transition metal silicates containing resin exhibited microbicidal nature against bacteria fungus and viruses enabling functional transition metal silicates usage as microbicides.

In a further embodiment of the present invention, wherein the functional transition metal silicates selected from cupric silicate, silver silicate, manganese silicate, zinc silicate and zirconium silicate optionally immobilized on materials selected from activated alumina, aluminium oxide, agropolymers, cellulose, quartz sand, silica gel, or functional transition metal silicates incorporated into resins or sand coated with functional transition metal silicates containing resin and having varied metal silicate ratio exhibiting varied functions gives a method to obtain selective conjugates of transition metals along with silicates for obtaining functionally effective functional transition metal silicates to use in various other applications such as manufacturing of catalysts, and hybridizing or doping with zeolites.

In further more embodiment of the present invention, wherein achieving of an inclusion of a desired functionality in a selected functional transition metal silicate is attainable by optimization of synthetic conditions selected from inclusion of arsenic sequestation ability into silver silicate, inclusion of bacterial decontamination property into zirconium silicate, inclusion of effective microbicidal (bactericidal and fungicidal) property into cupric silicate.

Now this invention will be described in detail so as to illustrate and explain various salient features of the invention.

One embodiment of the invention is to provide functional transition metal silicates to decontaminate metals, chemicals and disinfect microbes.

Synthesis of Functional Transition Metal Silicates:

The synthesis of various types of functional transition metal silicates were attained by reacting with different concentrations of transition metal salt solution with soluble silica containing alkali (with different silica alkali ratio) and at variable reaction conditions such as pH, and temperature.

Now this invention will describe one of the methods used in synthesis of functional transition metal silicates.

Transition metal salt solution (chlorides or nitrates or sulphates) was reacted to soluble silica. The soluble silica in alkaline medium was prepared by various ways, such as dissolving of sodium silicate or potassium silicate in water (distilled or deionized) or by dissolving amorphous silica in alkali such as sodium hydroxide or potassium hydroxide in water (distilled or deionized). Varied silica to alkali ratios was obtained in a soluble silica solution, by dissolving the amorphous silica with required amount of alkali. Different concentrations of transition metal salt solution were reacted with soluble silica (containing varied amount of alkali) at different pH conditions along with varied temperatures of reaction to obtain various types of functional transition metal silicates. The precipitate obtained after reaction of transition metal salts with soluble silica was washed extensively with distilled or deionized water to remove soluble substances.

The resultant purified materials of functional transition metal silicates were analyzed by SEM/EDAX (ESEM, XL-30), ESR (JEOL, JES-FA-200), AND XRD (PHILIPS, PW-1830) and other analytical estimation procedures (such as AAS, ICP-AES etc.,) to understand the composition, structure etc., details.

These substances (functional transition metal silicates) were evaluated for their comparative functional properties such as decontamination, disinfection, microbicidal, toxic gas detoxification and nicotine and tar detoxification etc. properties.

The metal decontamination ability was assayed by estimating arsenic sequestration capacity of these different functional transition metal silicates. Arsenic containing water was treated with functional transition metal silicate and the sequestered arsenic content by functional transition metal silicate was estimated by AAS or ICP-AES.

The microbial disinfection ability of these functional transition metal silicates was assayed by measuring the amount of bacteria (coliform or enterobacteria) removed from contaminated drinking water. Coliform or enterobacteria containing polluted water was added to normal drinking water and bacterial amount present before and after treatment with functional transition metal silicates was assayed. The bacterial assay was done by counting the individual bacterial colonies, which were obtained by inoculating the bacteria containing water on petriplates containing growth media.

The comparative fungicidal nature of functional transition metal silicates was assayed against *Sclerotium rolfsii, Rhizoctonia solani, Fusarium oxysporium*, and *Pyricularia oryzae*, by poison food technique (by adding test materials in the growth medium of fungus and measuring the growth of the fungus in comparison with control). The radial growth of the fungus in the petriplates was measured and percent inhibition of the growth of the fungus was calculated.

The microbicidal activity of functional transition metal silicate was assayed against gram positive and gram negative bacteria such as *Staphylococcus aureus, Bacillus subtilis, Pseudomonas aeruginosa*, and *Eschericia coli* by mixing functional transition metal silicates in growth media of bacteria. The growth of bacteria in media containing functional transition metal silicate was compared with control (bacterial growth media without functional transition metal silicate) in petriplates.

The comparative bactericidal nature of functional transition metal silicate containing different metal and silicate ratio was assayed against bacteria by adding various concentrations (such as 0.06, 0.125, 0.25%) of functional transition metal silicates in growth media.

The viral decontamination ability of these functional transition metal silicates was assayed using bacteriophages in water by batch method.

The chemical pollutants decontamination ability of these functional transition metal silicates was assayed by addition of functional transition metal silicates to contaminant such as trihalomethanes (chloroform, 1,1,1, trichloroethane, tetrachloroethylene, trichloroethylene, bromodichloroethane, dibromochloroethane, tetrachloroethylene, bromoform, 1,2, dichloro-3-bromopropane) containing water. After thorough shaking of the functional transition metal silicates with chemical pollutants dissolved water for 15 minutes, the resultant water containing functional transition metal silicate was allowed to precipitate for two hours. The chemical pollutants content present in treated solution was assayed by using GC-FID or GC-ECD or GC/MS/MS.

One embodiment of the invention is to provide immobilized functional transition metal silicates to decontaminate (metals, chemicals, and pesticides), disinfect microbes (fungus, protozoa, bacteria, and viruses), and to detoxify toxic gases, nicotine and tar etc.

Transition metal (silver, copper, zinc, manganese, and zirconium) salt solution, (such as chlorides or nitrates or sulphates of these metals) was mixed with materials such as activated alumina, aluminium oxide, agropolymers, cellulose, quartz sand, and silica gel and corresponding immobilized transition metal silicate was obtained by treating with sodium silicate or potassium silicate solution. This process was achieved in another way by adding initially sodium silicate or potassium silicate solution to the materials such as activated alumina, aluminium oxide, agropolymers, cellulose, quartz sand, and silica gel and corresponding immobilized functional transition metal silicates were obtained by treating with salts of silver, cupric, zinc, manganese, and zirconium, (such as chlorides or nitrates or sulphates of these metals).

Transition metal (silver, copper, zinc, manganese, and zirconium) salt solution, (such as chlorides or nitrates or sulphates of these metals) was added to solution containing sodium silicate or potassium silicate to obtain respective functional transition metal silicate and thus obtained transition metal silicate was mixed with resins such as vinyl ester, or bisphenol resins, or isopthalic resins of food grade, without catalysts (such as cobalt octate) and allowed to polymerize after heating at 70° C. to 90° C. Later these materials were powdered to obtain desired particle size.

In a preferred embodiment the present invention provides a method of producing immobilized transition metal substances (silver silicate, cupric silicate, zinc silicate, manganese silicate, and zirconium silicate), said method comprising the following steps.
  a) Addition of soluble transition metal salt solution to the selected matrix for immobilization such as activated alumina, aluminum oxide, bisphenol resins, agropolymers, cellulose, quartz sand and silica gel.
  b) Treating the matrix containing metal salts with solution of sodium silicate or potassium silicate to obtain corresponding metal silicate immobilized on matrix.
  c) Washing extensively with distilled or deionized water to remove unbound, non-immobilized substances from the matrix such as activated alumina, aluminum oxide, agropolymers, cellulose, quartz sand and silica gel.
  d) Drying the resultant material either by centrifugation, filtration and or by heating.

Another embodiment of the present invention relates to a method of production of immobilized functional transition metal silicates (silver silicate, cupric silicate, zinc silicate, manganese silicate, and zirconium silicate) by incorporating functional transition metal silicate into resins such as vinyl ester, or bisphenol resins, or isopthalic resins of food grade.

Another embodiment of the present invention relates to a method of production of immobilized functional transition metal silicates (silver silicate, cupric silicate, zinc silicate, manganese silicate, and zirconium silicate) containing resins (such as vinyl ester, or bisphenol resins, or isopthalic resins of food grade) coating on solid matrix like quartz sand.

Now this invention will describe one of the methods used in production of immobilized functional transition metal silicates. Most of these immobilizations were carried either at neutral reaction conditions (6-7 pH) or at acidic reaction conditions (2 pH).

These illustrations explained below do not limit the scope of invention i.e., production of immobilized functional transition metal silicates using various other matrixes along with varied reaction conditions.

Immobilization of Functional Transition Metal Silicates on Activated Alumina:

Transition metal salt solution (0.5 gm/ml) was added to activated alumina granules followed by alkali silicate solution (such as sodium silicate or potassium silicate-0.5 g/ml, alkali:silica=1:1) addition to obtain functional transition metal silicate immobilized on activated alumina. Various sizes of activated alumina (100-2000 micron size) were chosen to obtain immobilized functional transition metal silicates. Varied reaction times along with initial chemical concentrations were chosen for immobilization along with varied concentration of metal salts to alkali content as described earlier. The unbound, non-immobilized materials were removed by washing extensively with distilled or deionized water. The immobilization of functional transition metal silicate content was achieved to 1-9% (w/w) on activated alumina based on number of coatings, and different reaction conditions.

Immobilization of Functional Transition Metal Silicates on Aluminium Oxide:

The neutral aluminium oxide (column chromatography grade) was mixed with transition metal salt solution (0.5 g/ml) and later functional transition metal silicates formation and immobilization was done by addition of sodium silicate or potassium silicate solution (0.5 g/ml, alkali:silica=1:1). The unbound, non-immobilized materials were washed extensively with distilled or deionized water.

The immobilization of functional transition metal silicate content was achieved up to 2-10% (w/w) on aluminium oxide based on number of coatings.

Immobilization of Functional Transition Metal Silicates on Agropolymers:

Transition metal salts containing solution (0.5 g/ml) was added to various agropolymers derived from seed coats of various crops and functional transition metal silicates were immobilized by adding sodium silicate or potassium silicate solution at pH 3-4 (0.5 g/ml, alkali:silica=1:1). The unbound materials were washed extensively with distilled or deionized water to remove non-immobilized materials, and the resultant agropolymer containing functional transition metal silicate was dried at room temperature or by heating. The immobilized functional transition metal silicate content on agropolymers varied from 2-25 percent (w/w) based on number coatings.

Immobilization of Functional Transition Metal Silicates on Cellulose:

Micro crystalline, cellulose (column chromatography grade), was mixed with transition metal salt containing solution (0.5 g/ml) and immobilization was attained by adding sodium silicate or potassium silicate solution (0.5 g/ml, alkali:silica=1:1). The functional transition metal silicate immobilized materials were dried, after thorough washing with distilled or deionized water to remove unbound or non-immobilized materials. The immobilized functional transition metal silicate content on cellulose was achieved up to 3-10% (w/w) based on number of coatings.

Immobilization of Functional Transition Metal Silicates on Silica Gel:

Transition metal salt containing solution (0.5 g/ml) was added to silica gel (500 microns) and immobilization was attained by adding sodium silicate or potassium silicate (0.5 g/ml, alkali:silica=1:1) solution. The unbound substances were washed extensively with distilled or deionized water and the functional transition metal silicate immobilized silica gel was obtained after drying at 100° C.

Immobilization of Functional Transition Metal Silicates on Quartz Sand:

Quartz sand of various sizes were washed thoroughly with light acid (0.1% HCl, or $H_2SO_4$) later after removing of acidic traces, the transition metal salt containing solution was added and dried at room temperature or in a oven, to obtain, more content of transition metal layer impregnated on sand particle. Later to the dried metal salt impregnated sand, the solution of sodium silicates or potassium (sodium to silica ratio=1:1) was mixed thoroughly to obtain, immobilized functional transition metal silicates at 2-3 pH. The unbound, non-impregnated or non-immobilized metal or other substances were washed extensively with distilled or deionized water, and the resultant material was dried. The immobilized functional transition metal silicate content on quartz sand was achieved up to 0.1-1.5 percent (w/w) based on number of coatings.

Immobilization of Functional Transition Metal Silicates by Incorporating in to Vinyl Ester, or Bisphenol or Isopthalic Resins As previously described silver, copper, zinc, zirconium and manganese salts (such as chlorides, nitrates, sulphates) were added to solution of sodium silicate or potassium silicates to obtain functional transition metal silicates at acidic reaction conditions (pH 2) and these obtained functional transition metal silicates were mixed with resins such as vinyl ester, or bisphenol or isopthalic resins, without metallic catalysts (such as cobalt octate), and were allowed to polymerize after heating at 70° C. to 90° C. Later these materials were powdered to obtain desired particle size. Later these materials were powdered to obtain desired particle size. 5-20% (w/v) of functional transition metal silicates were incorporated in to resins.

The immobilized functional transition metal silicates of desired particle size (in microns) were obtained by grinding and or by passing through required size mesh.

Functional Transition Metal Silicate Containing Resin Coating on Solid Matrix materials such as Quartz Sand:

Functional transition metal silicates (silver silicate, cupric silicate, zinc silicate, zirconium silicate and manganese silicate) produced at acidic pH reaction conditions were mixed either with vinyl ester or bisphenol or isopthalic food grade resins at various doses ranging from 0.5:1 to 4:1 (w/v). This functional transition metal silicate containing resin was coated on solid matrix materials such as quartz sand by vigorously mixing. The resin-coated quartz sand was dried without addition of any catalyst or accelerators at 70° C. to 90° C. or by keeping at room temperature for a week, for polymerization.

Amount of immobilized functional transition metal silicate on a matrix varies based on initial concentration of transition metal salt, soluble silica, the reaction time, particle size and type of matrix, and mode of immobilization such as physical or chemical. These immobilizations in present invention can be classified as physical or chemical or incorporating directly into resins or coating of functional transition metal silicate containing resins on solid matrix like quartz sand.

The chemical immobilization means that transition metal salt solution reacts or transition metal content chemically binds to the material selected, such as activated alumina, agropolymer and silica gel. Activated alumina, as it is amphoteric, passes the electron to charged copper. Agropolymers contain transition metal binding reactive sites and can absorb significant amount of transition metal on to them.

Physical immobilization of functional transition metal silicates was done on cellulose, quartz sand, and incorporating into resins.

The immobilized functional transition metal silicates have extensive industrial applications for decontamination disinfection, and in other various fields. The wide application of the said functional transition metal silicates is an important aspect of the invention.

Accordingly the invention pertains to a method of producing immobilized functional transition metal silicates using activated alumina, aluminum oxide, cellulose, resins, quartz sand, functional transition metal silicate incorporated resins and functional transition metal silicate containing resin coatings on solid matrix like quartz sand.

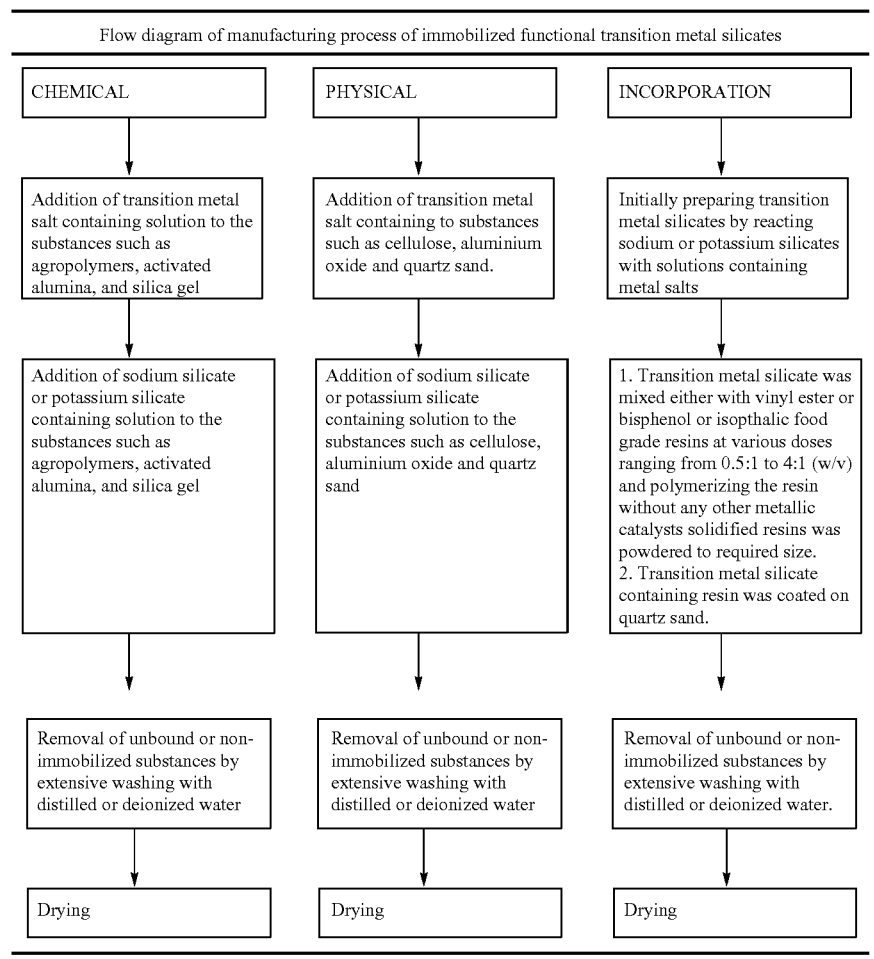

Flow diagram of manufacturing process of immobilized functional transition metal silicates In the embodiment of present invention, a method of decontamination of toxic metals, like arsenic, mercury etc., and disinfection of microbes such as fungi, bacteria, viruses, and protozoa by functional transition metal silicates is described.

This invention describes immobilization of functional transition metal silicates, in three ways such as:

1. Immobilization on substances like activated alumina, aluminium oxide, cellulose, vinyl ester resin, bisphenol resin, isopthalic food grade resins, quartz sand, and silica gel.
2. Incorporation of functional transition metal silicates in to resins such as vinyl ester resin or bisphenol resin or isopthalic food grade resins and later polymerizing with these resins.
3. Coating of functional transition metal silicates containing resins on solid matrix like quartz sand.

This invention relates to effective utilization of immobilized functional transition metal silicates.

Although many methods are known for decontamination and disinfection using metals, but integrated methods, were not developed for both metal, chemical decontamination, and or microbial disinfection. Present method offers and integrated method of decontamination and disinfection of drinking water and other polluted water, at cheaper cost and in an effective way.

BRIEF DESCRIPTION OF THE STRUCTURAL DETAILS OF THE FUNCTIONAL TRANSITION METAL SILICATES ARE ENCLOSED IN THE ACCOMPANYING INFORMATION

FIG. 1A: Composition analysis of cupric silicate (synthesized at acidic reaction conditions) using EDAX attached to SEM (Scanning Electron Microscope).

FIG. 1B: ESR (Electron spin resonance) spectrometer analysis of cupric silicate (synthesized at acidic reaction conditions).

Figure 1C:
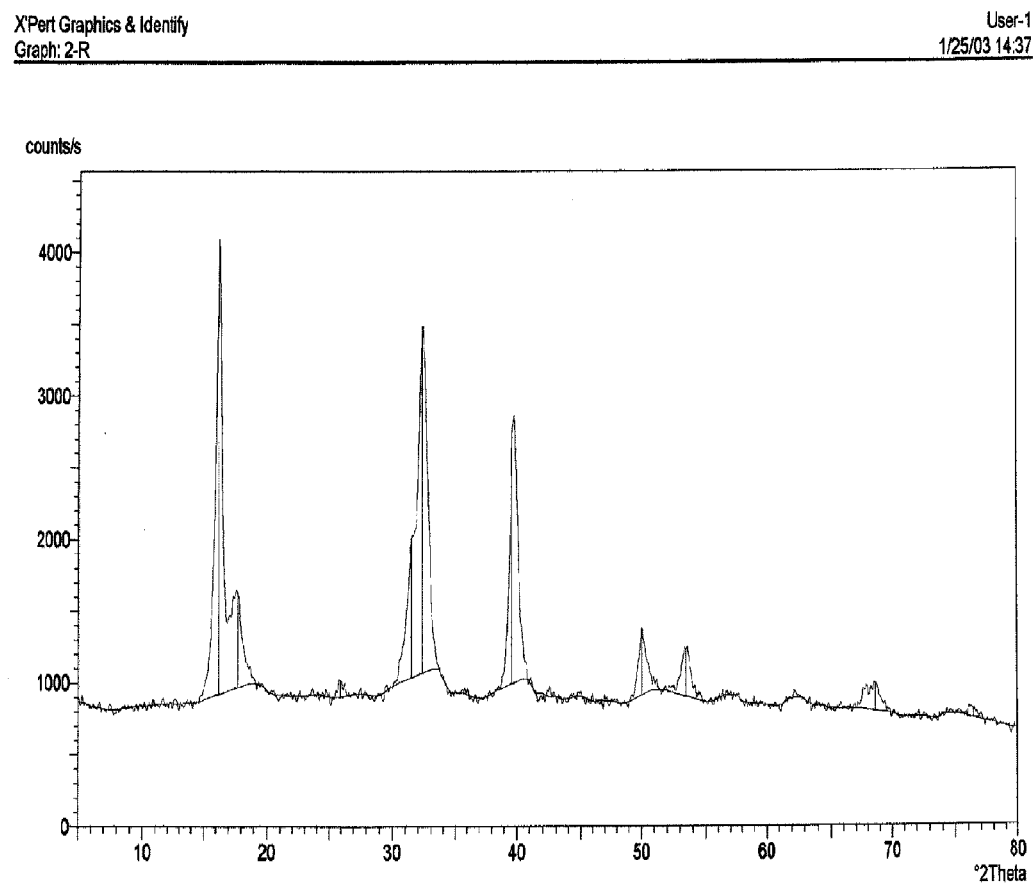

FIG. 1C and FIG. 1D: XRD (X-ray diffraction) pattern of cupric silicate (synthesized at acidic reaction conditions).

FIG. 2A: Composition analysis of cupric silicate (synthesized at acidic reaction conditions and at high temperature: 70° C. to 90° C.) using EDAX attached to SEM (Scanning Electron Microscope).

Figure 2B:
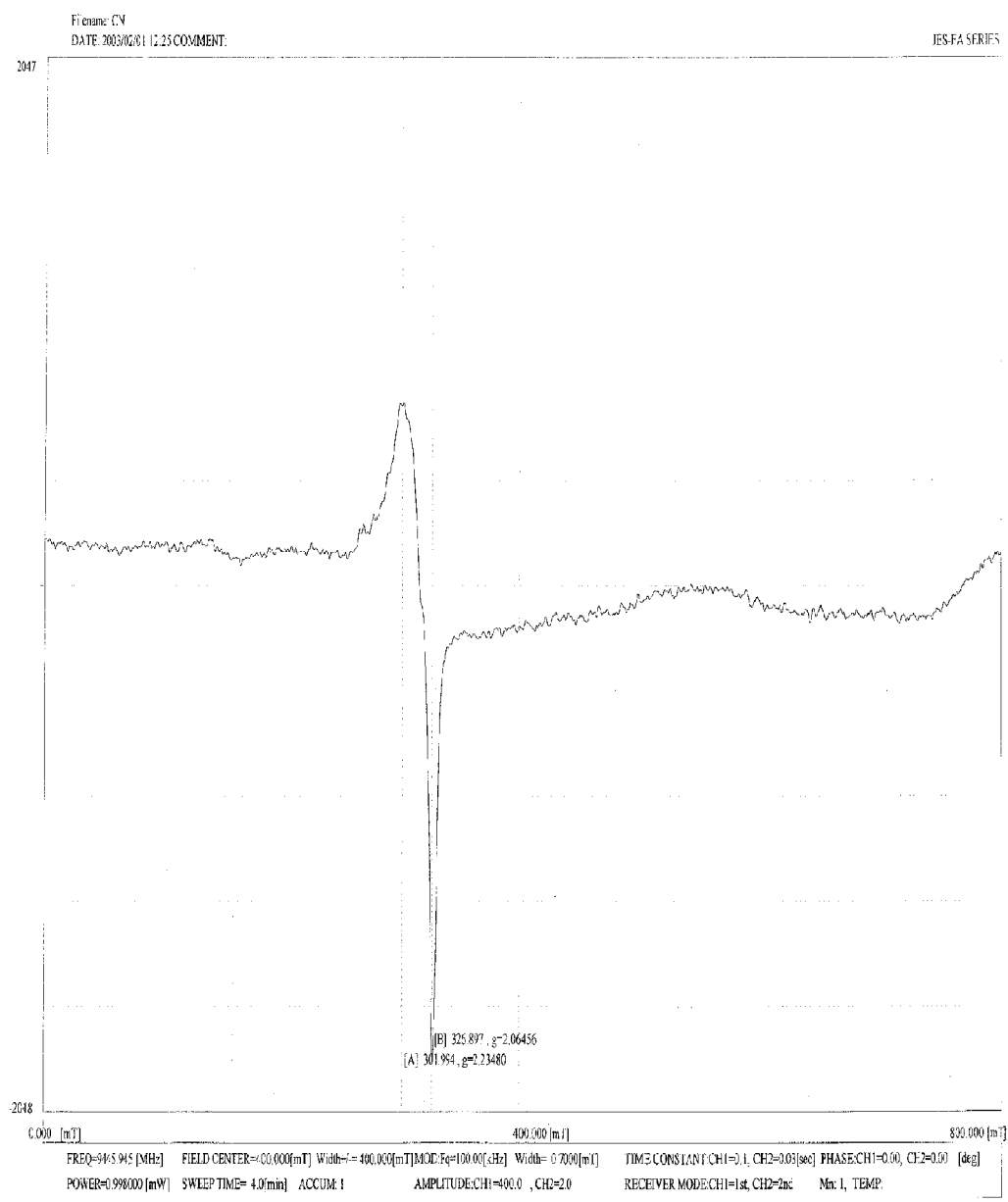

FIG. 2B: ESR (Electron spin resonance) spectrometer analysis of cupric silicate (synthesized at acidic reaction conditions and at higher temperature: 70° C. to 90° C.).

Figure 2C:
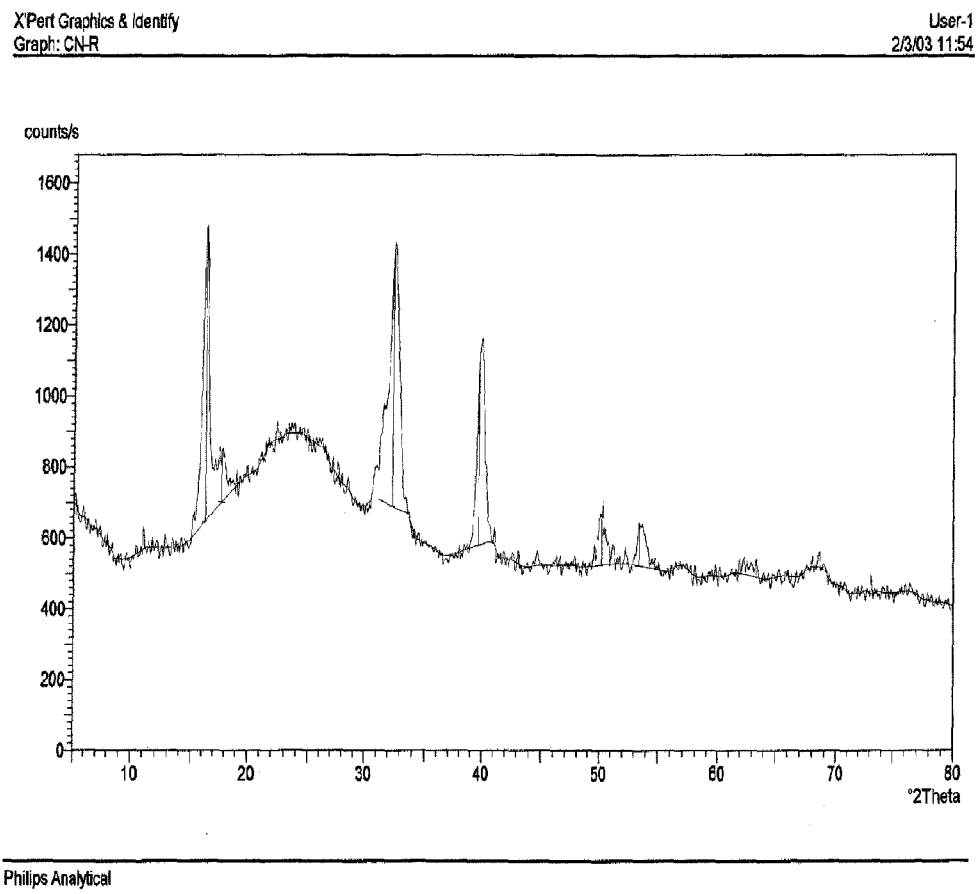

FIG. 2C and FIG. 2D: XRD (X-ray diffraction) pattern of cupric silicate (synthesized at acidic reaction conditions and at higher temperature: 70° C. to 90° C.).

FIG. 3A: Composition analysis of cupric silicate (synthesized at neutral (pH 6-7) reaction conditions) using EDAX attached to SEM (Scanning Electron Microscope).

Figure 3B:
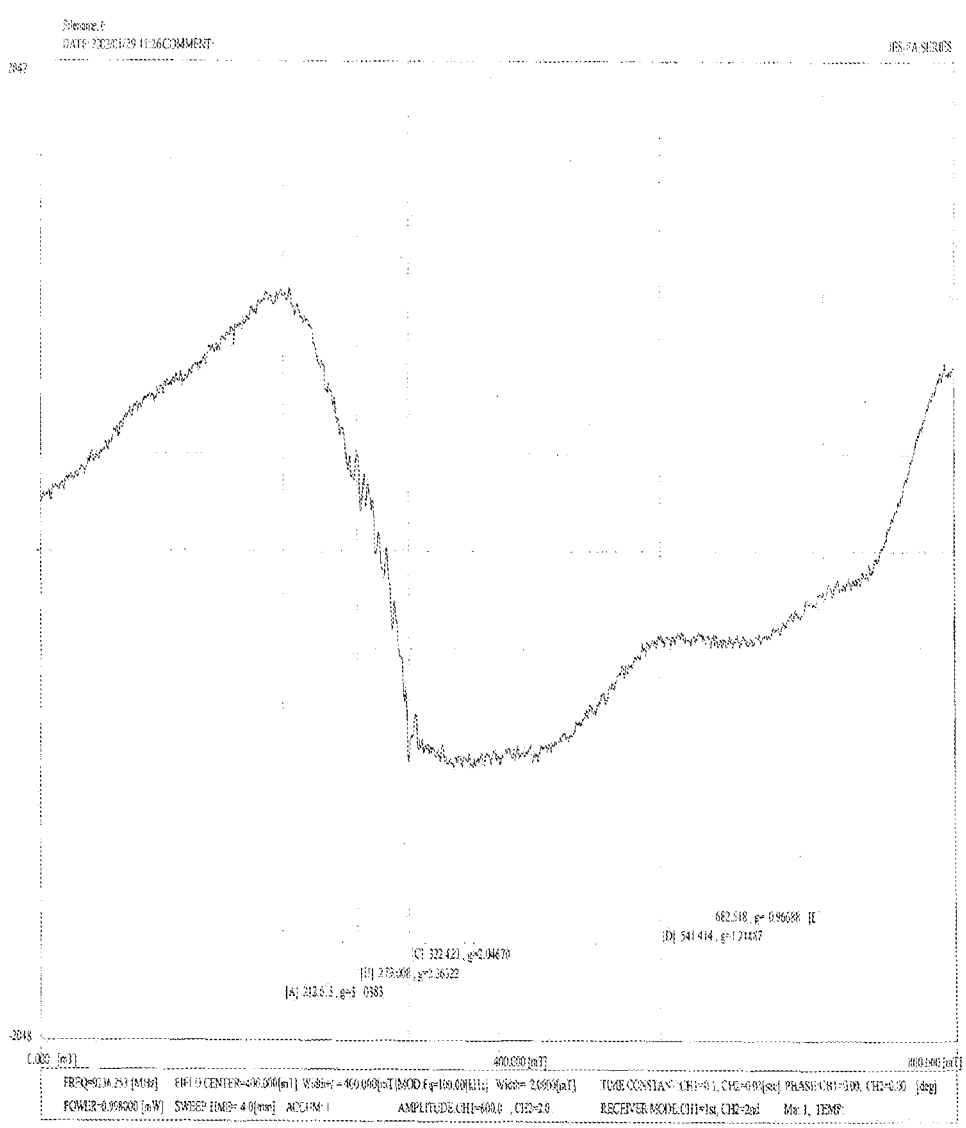

FIG. 3B: ESR (Electron spin resonance) spectrometer analysis of cupric silicate (synthesized at neutral (pH 6-7) reaction conditions).

Figure 3C:
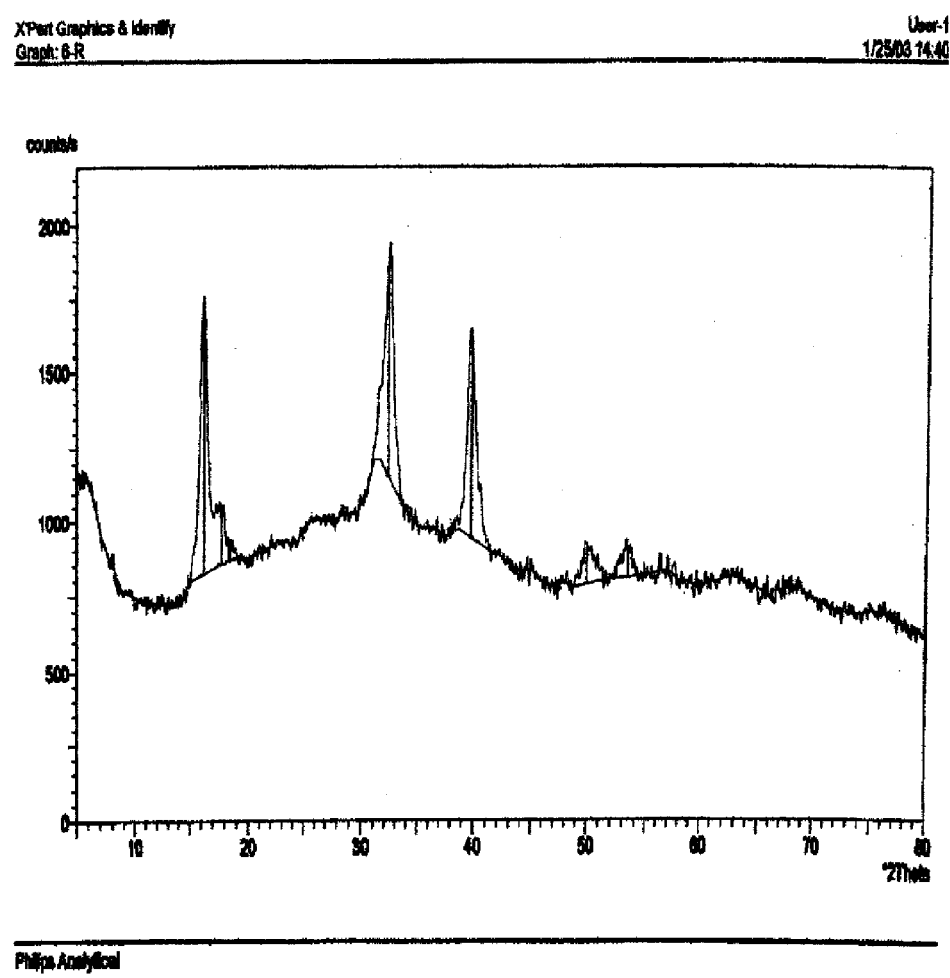

FIGS. 3C and 3D: XRD (X-ray diffraction) pattern of cupric silicate (synthesized at neutral (pH 6-7) reaction conditions).

FIG. 4A: Composition analysis of cupric silicate (synthesized at basic (pH 10-11) reaction conditions) using EDAX attached to SEM (Scanning Electron Microscope).

Figure 4B:
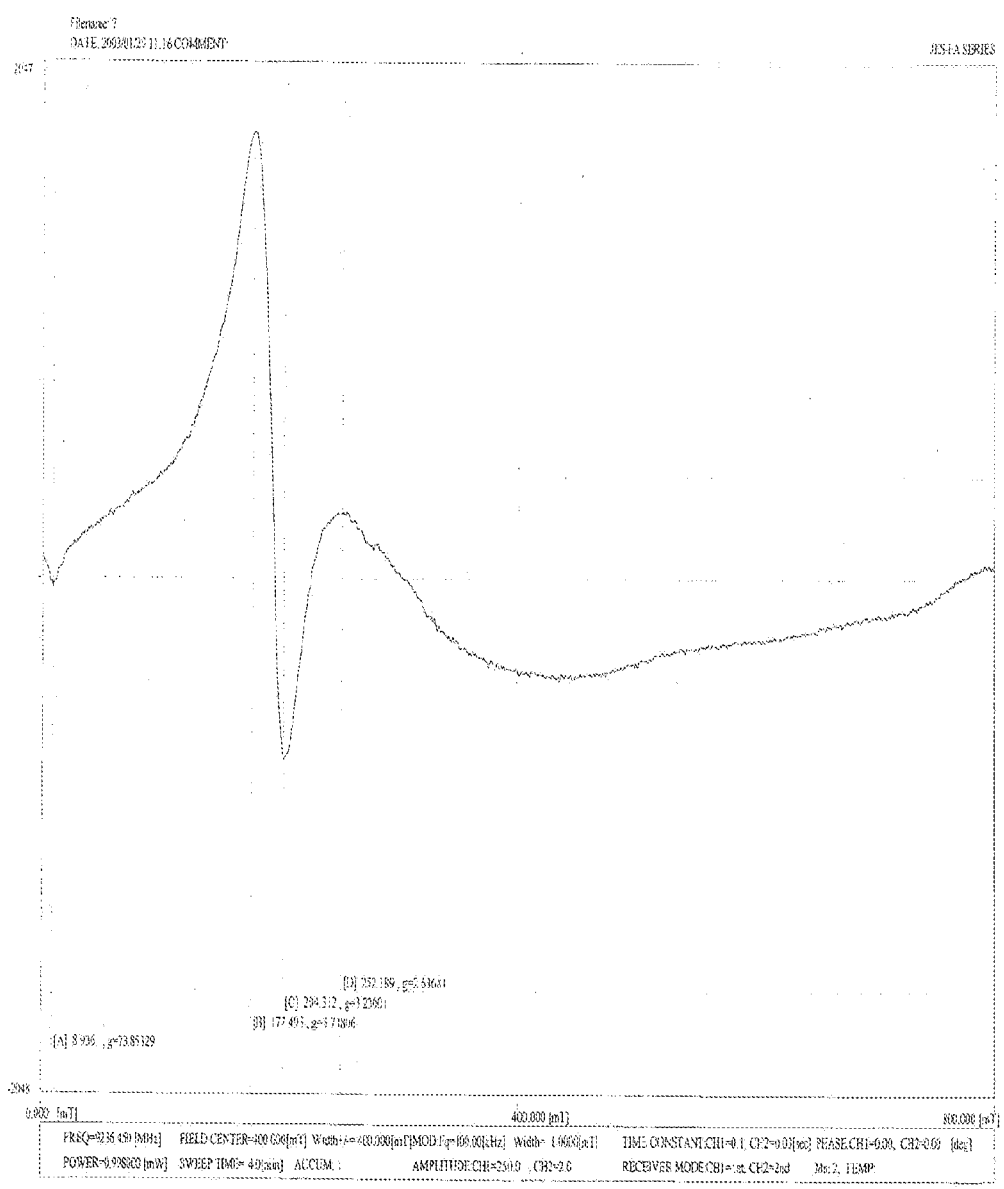

FIG. 4B: ESR (Electron spin resonance) spectrometer analysis of cupric silicate (synthesized at basic (pH 10-11) reaction conditions).

Figure 4C:
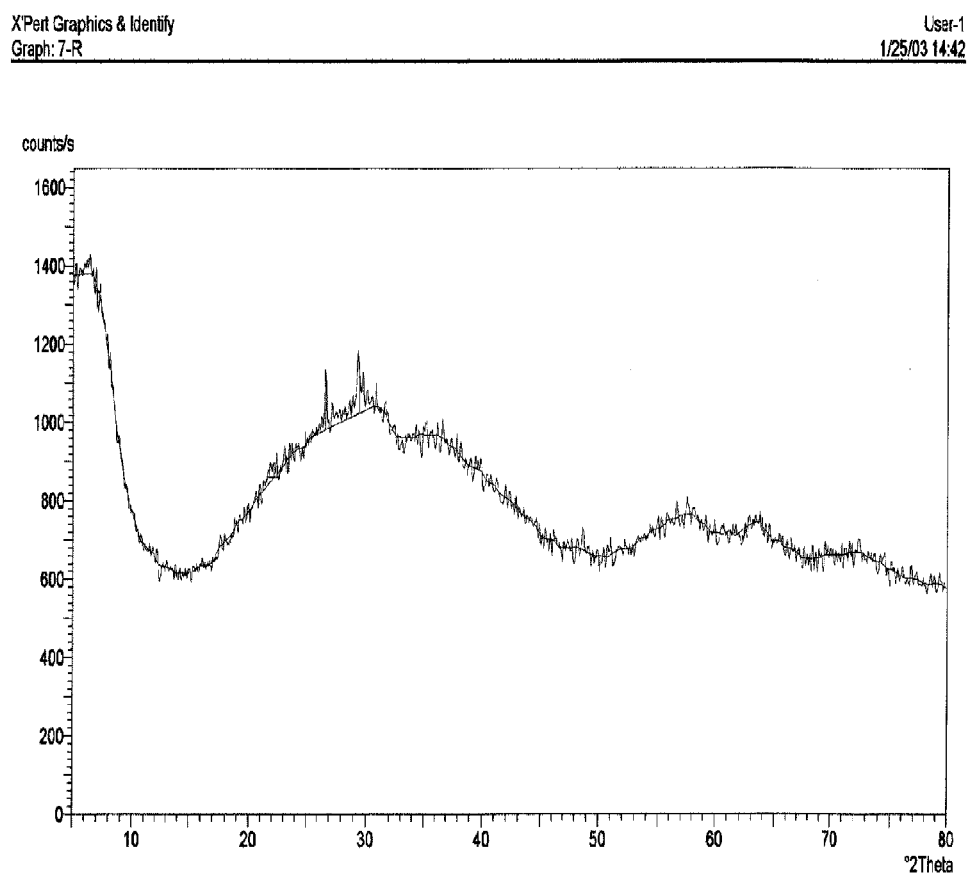

FIG. 4C and FIG. 4D: XRD (X-ray diffraction) pattern of cupric silicate (synthesized at basic (pH 10-11) reaction conditions).

FIG. 5A: Composition analysis of cupric silicate (synthesized at extreme acidic (below pH 2) reaction conditions by addition of 10 ml of 36% HCl and at higher temperature: 70° C. to 90° C.) using EDAX attached to SEM (Scanning Electron Microscope).

Figure 5B:
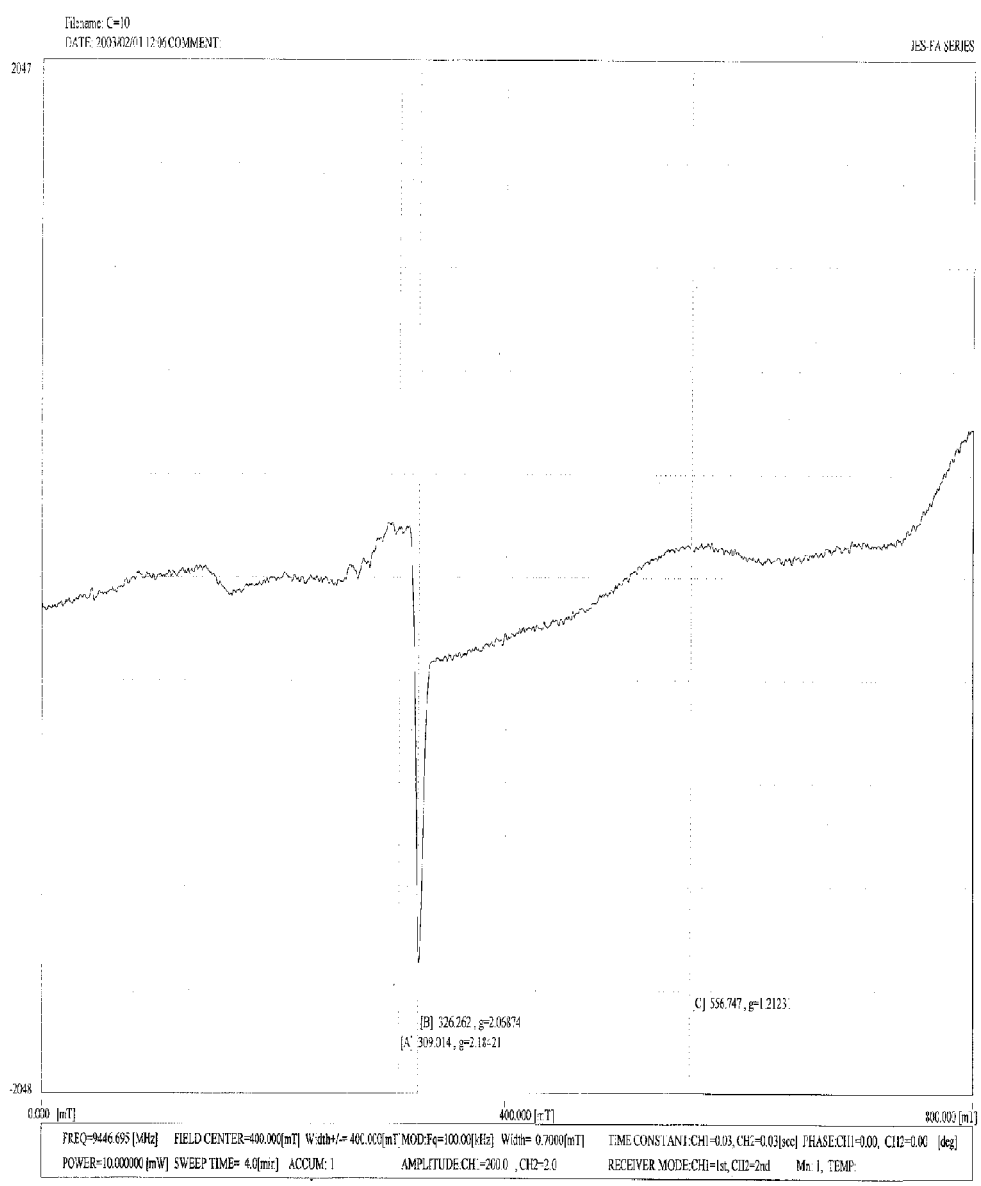

FIG. 5B: ESR (Electron spin resonance) spectrometer analysis of cupric silicate (synthesized at extreme acidic (below pH 2) reaction conditions by addition of 10 ml of 36% HCl and at higher temperature: 70° C. to 90° C.).

Figure 5C:
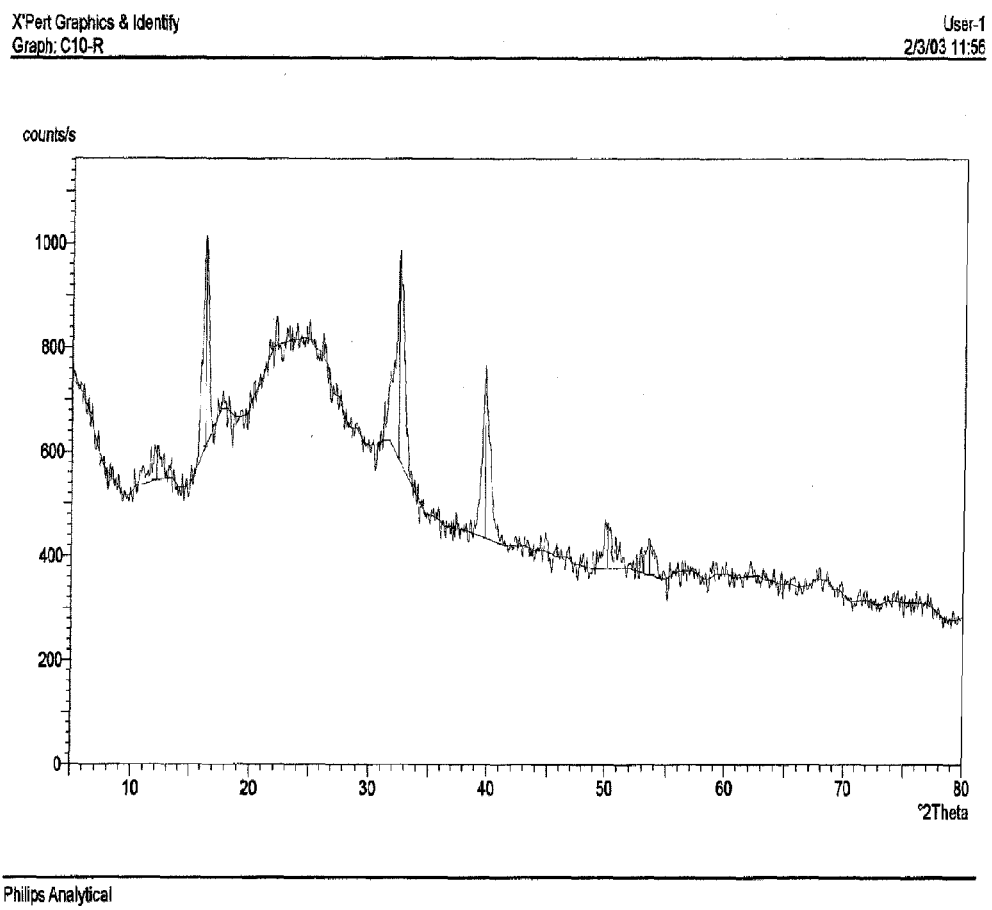

FIG. 5C and FIG. 5D: XRD (X-ray diffraction) pattern of cupric silicate (synthesized at extreme acidic (below pH 2) reaction conditions by addition of 10 ml of 36% HCl and at higher temperature: 70° C. to 90° C.).

FIG. 6A: Composition analysis of cupric silicate (synthesized at extreme acidic (below pH 2) reaction conditions by addition of 20 ml of 36% HCl and at higher temperature: 70° C. to 90° C.) using EDAX attached to SEM (Scanning Electron Microscope).

Figure 6B:
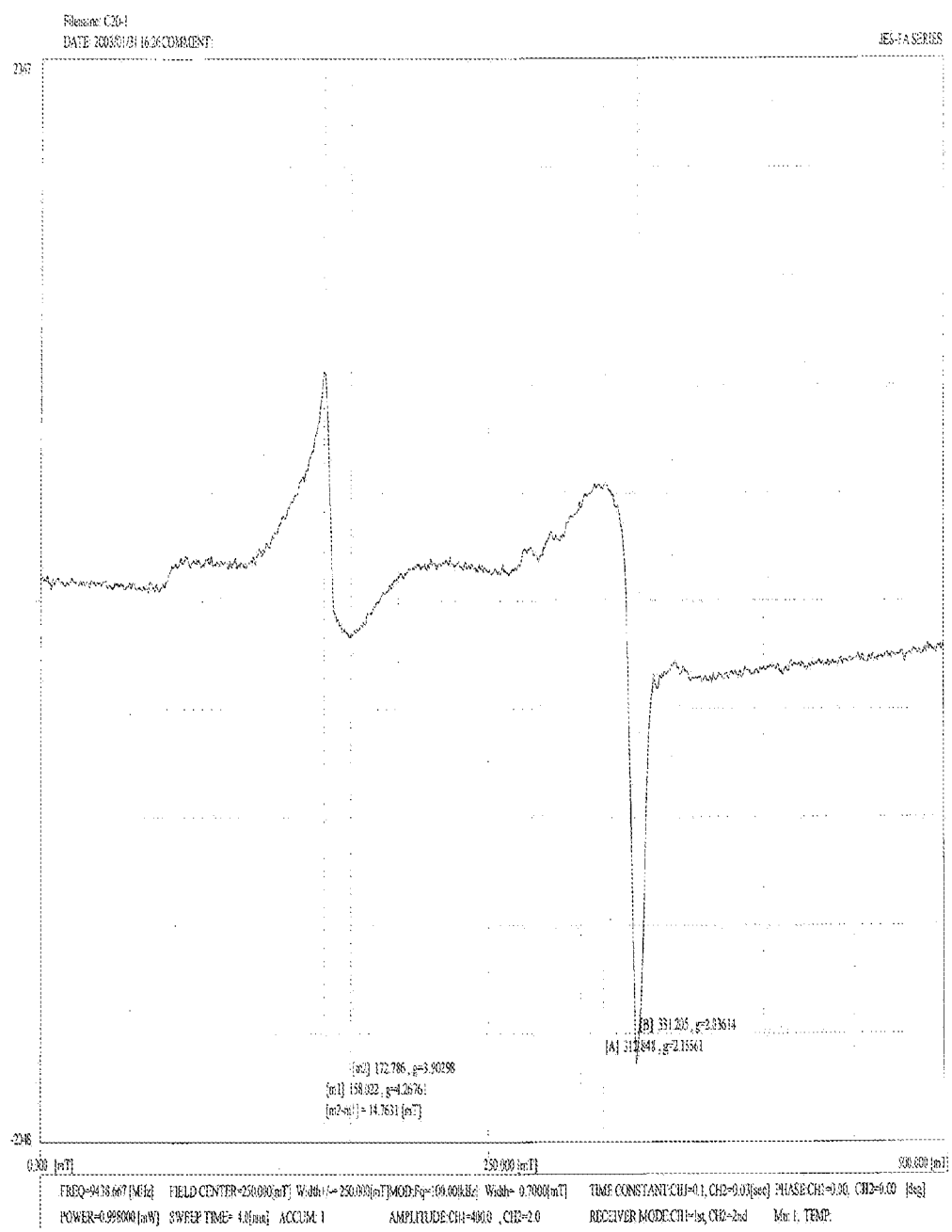

FIG. 6B: ESR (Electron spin resonance) spectrometer analysis of cupric silicate (synthesized at extreme acidic (below pH 2) reaction conditions by addition of 20 ml of 36% HCl and at higher temperature: 70° C. to 90° C.).

Figure 6C:
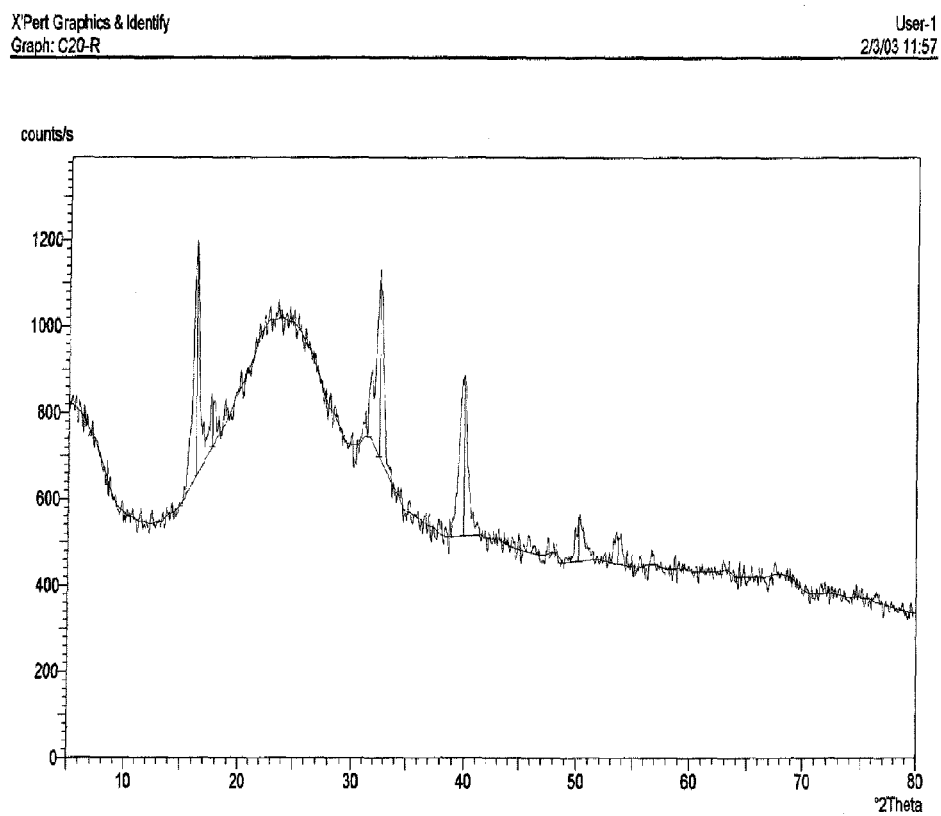

FIG. 6C and FIG. 6D: XRD (X-ray diffraction) pattern of cupric silicate (synthesized at extreme acidic (below pH 2) reaction conditions by addition of 20 ml of 36% HCl and at higher temperature: 70° C. to 90° C.).

FIG. 7A: Composition analysis of zinc silicate (synthesized at neutral (pH 6-7) reaction conditions) using EDAX attached to SEM (Scanning Electron Microscope).

Figure 7B:
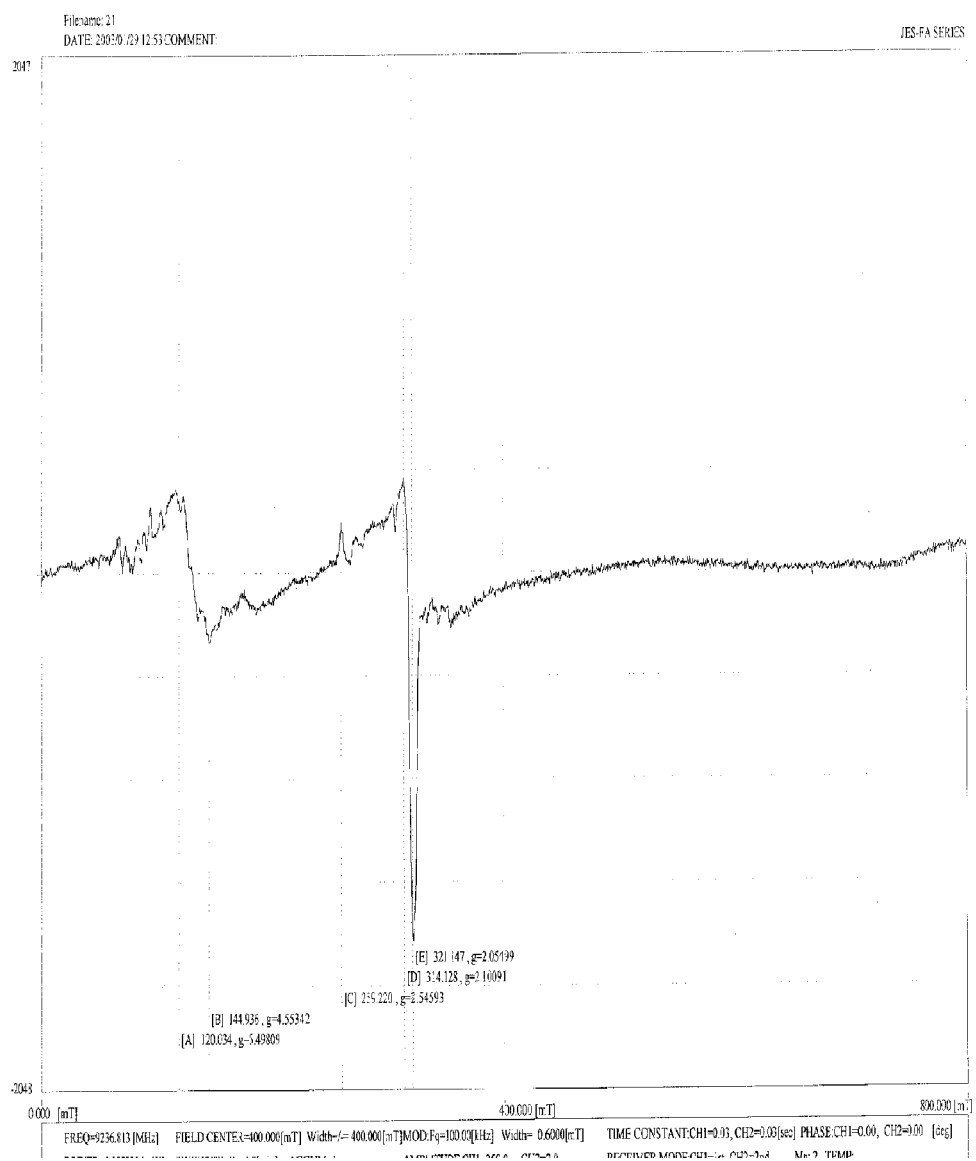

FIG. 7B: ESR (Electron spin resonance) spectrometer analysis of zinc silicate (synthesized at neutral (pH 6-7) reaction conditions).

Figure 7C:
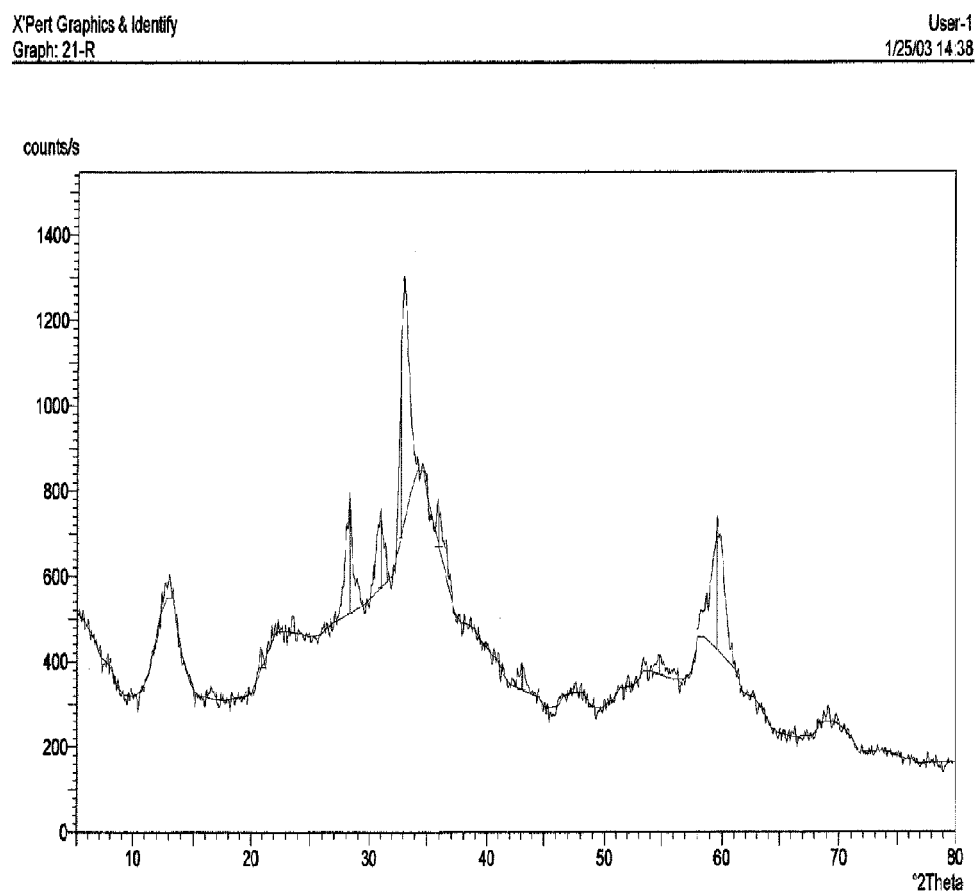

FIG. 7C and FIG. 7D: XRD (X-ray diffraction) pattern of zinc silicate (synthesized at neutral (pH 6-7) reaction conditions).

FIG. 8A: Composition analysis of zinc silicate (synthesized at extreme acidic reaction conditions (below pH 2) and at higher temperature: 70° C. to 90° C.) using EDAX attached to SEM (Scanning Electron Microscope).

Figure 8B:
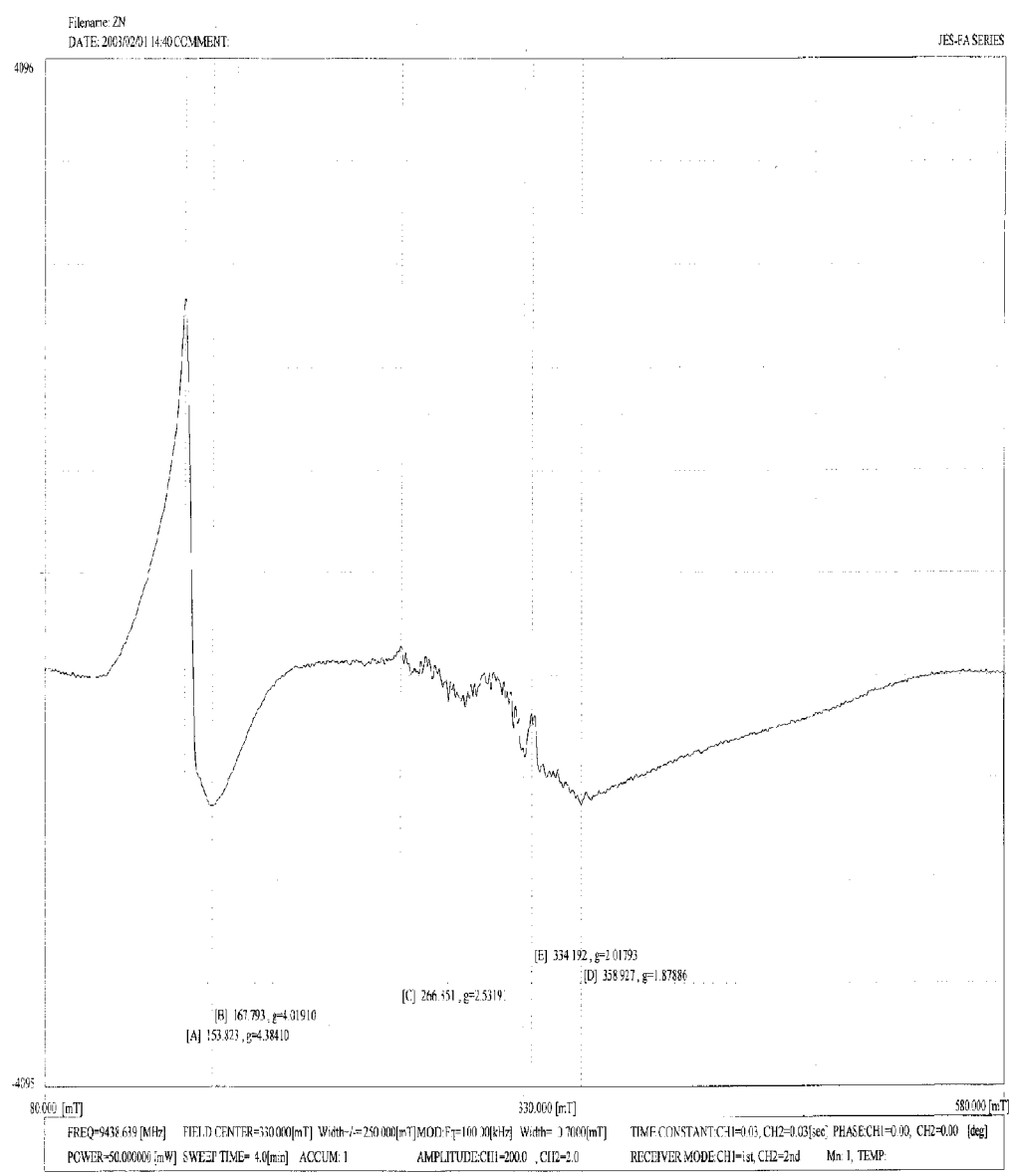
Figure 8C:
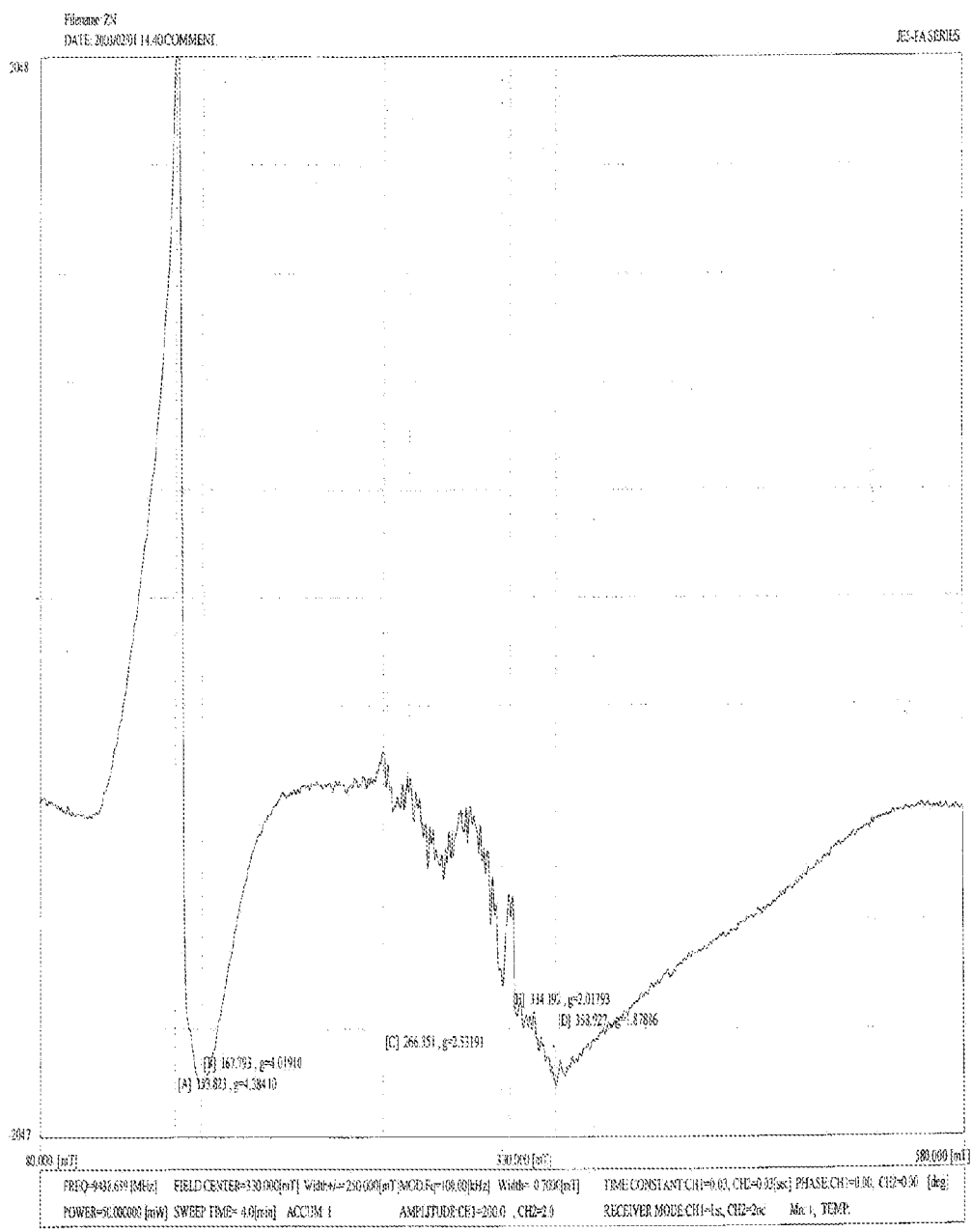

FIG. 8B and FIG. 8C: ESR (Electron spin resonance) spectrometer analysis of zinc silicate (synthesized at extreme acidic reaction conditions (below pH 2) and at higher temperature: 70° C. to 90° C.).

Figure 8D:
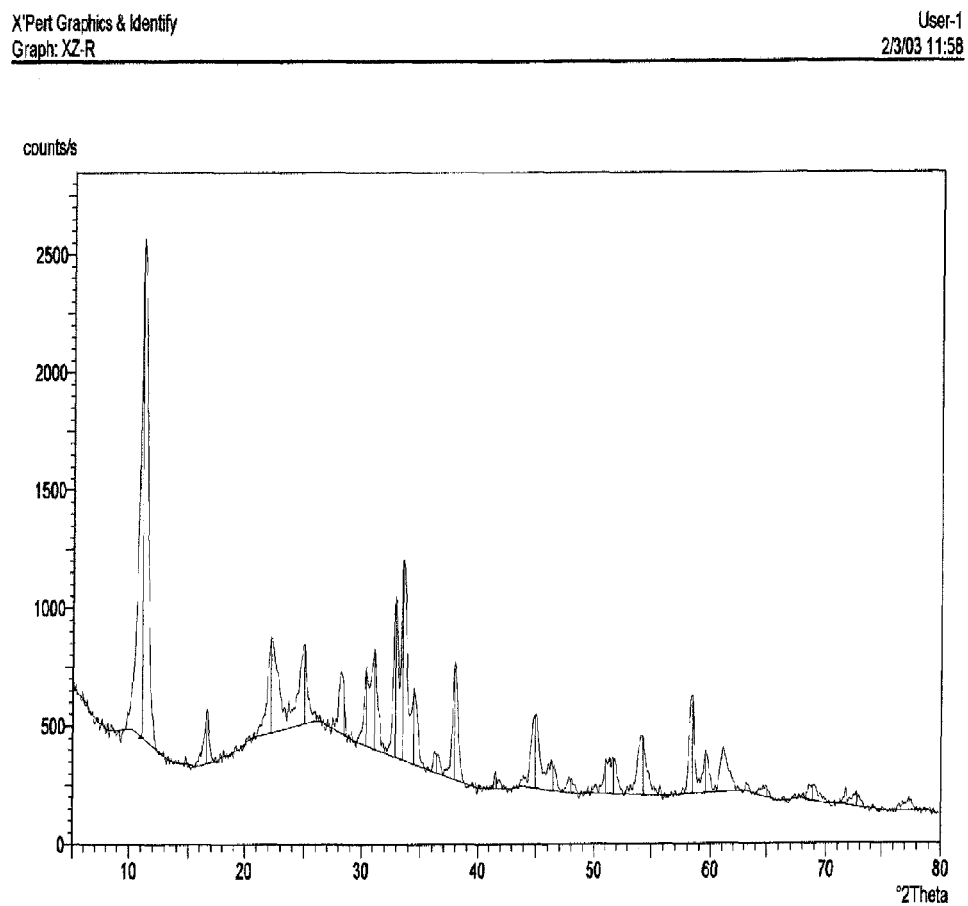

FIG. 8D and FIG. 8E: XRD (X-ray diffraction) pattern of zinc silicate (synthesized at extreme acidic reaction conditions (below pH 2) and at higher temperature: 70° C. to 90° C.).

FIG. 9A: Composition analysis of silver silicate (synthesized at neutral (pH 6-7) reaction conditions) using EDAX attached to SEM (Scanning Electron Microscope).

Figure 9B:
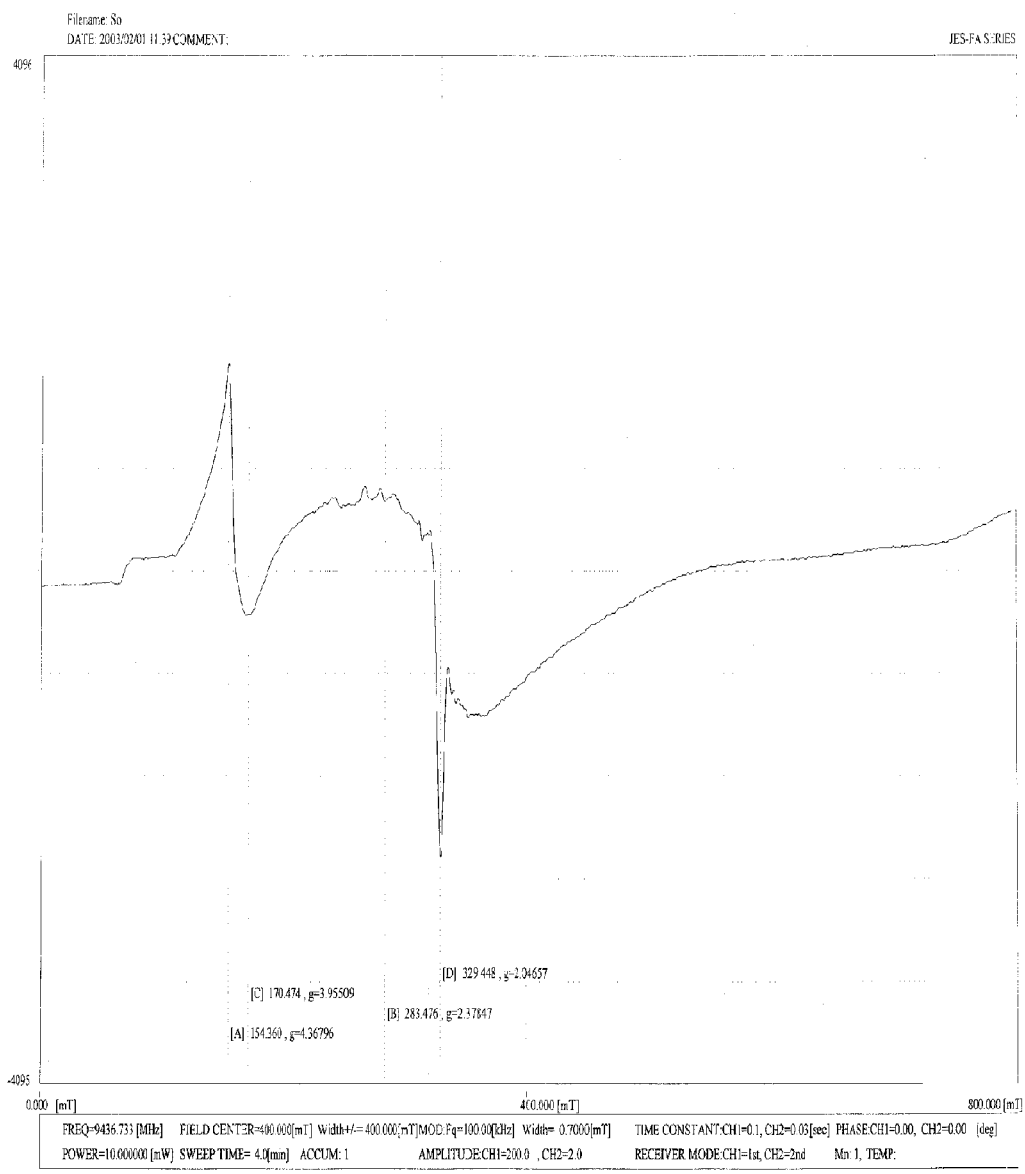

FIG. 9B: ESR (Electron spin resonance) spectrometer analysis of silver silicate (synthesized at neutral (pH 6-7) reaction conditions).

Figure 9C:
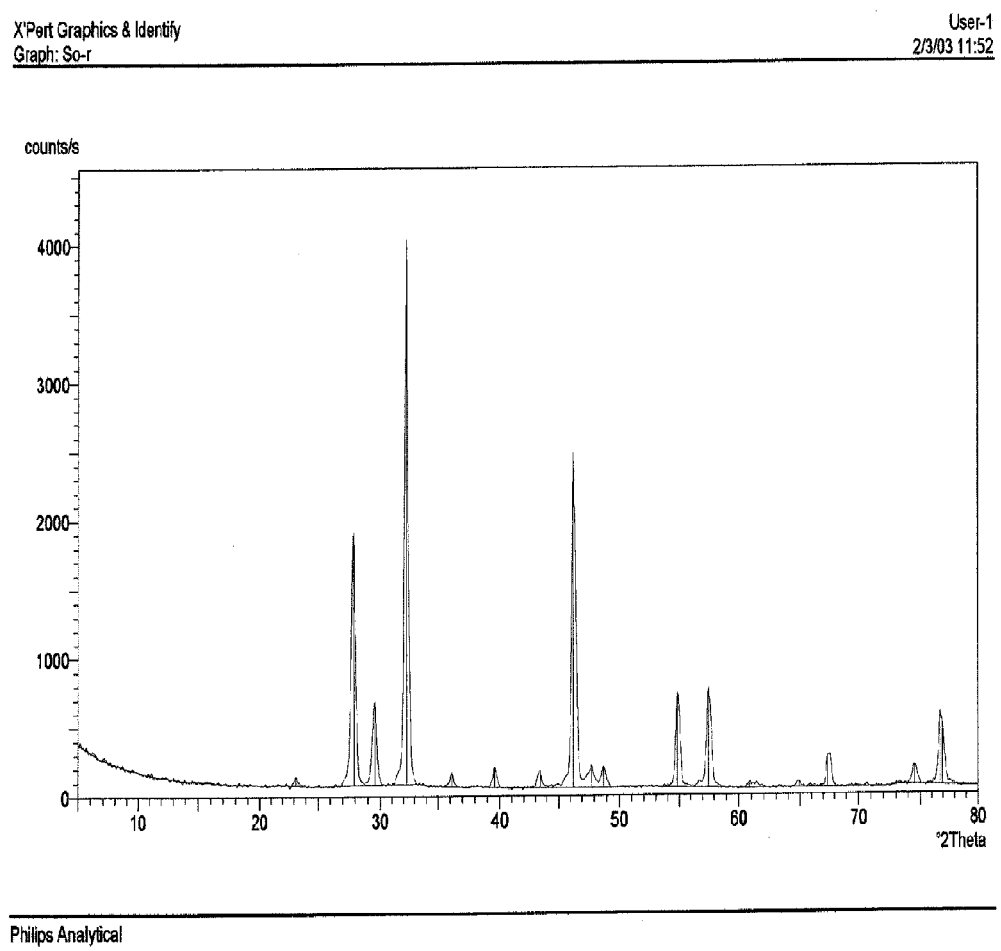

FIG. 9C and FIG. 9D: XRD (X-ray diffraction) pattern of silver silicate (synthesized at neutral (pH 6-7) reaction conditions).

FIG. 10A: Composition analysis of silver silicate (synthesized at acidic (pH 2) reaction condition and at higher temperature: 70° C. to 90° C.) using EDAX attached to SEM (Scanning Electron Microscope).

Figure 10B:
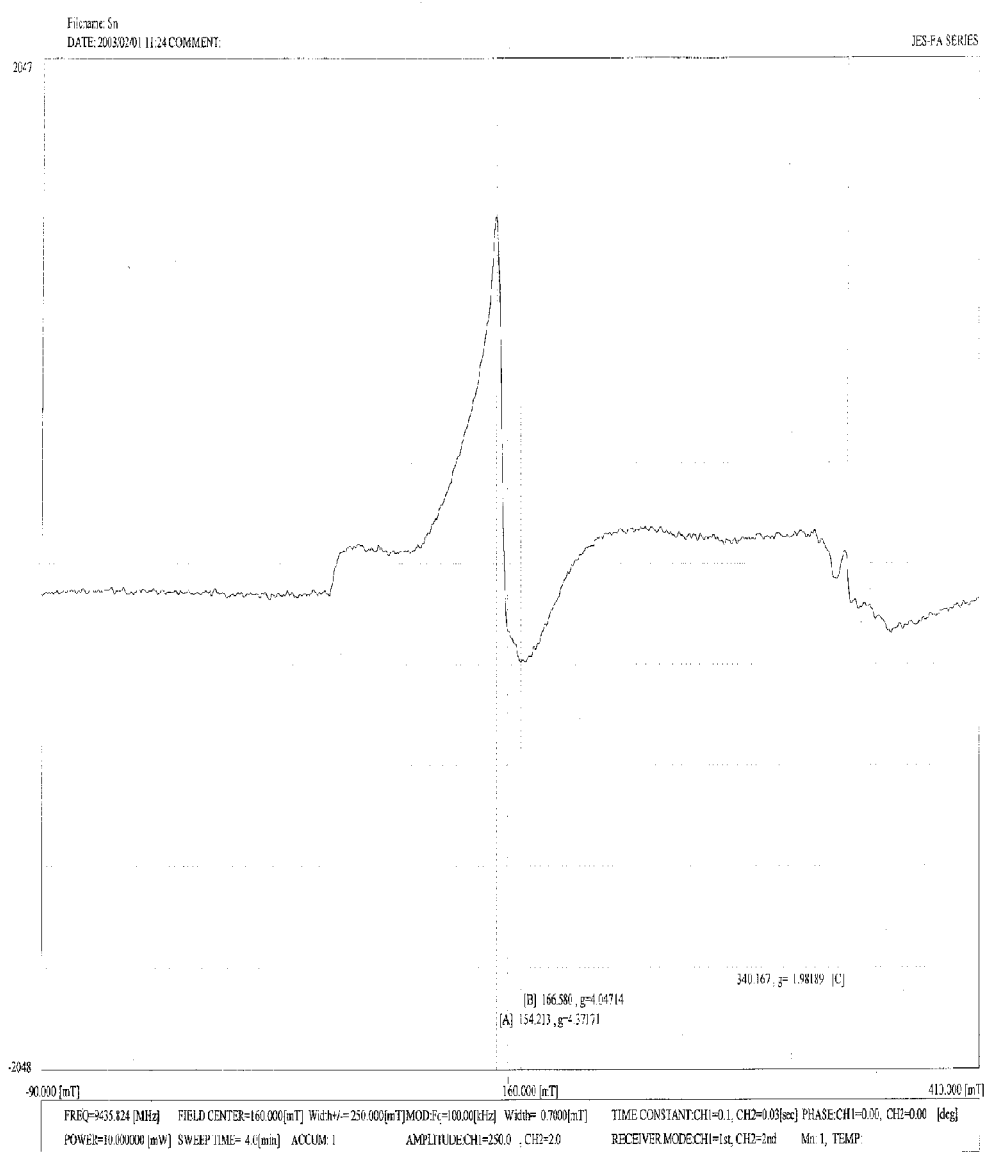

FIG. 10B: ESR (Electron spin resonance) spectrometer analysis of silver silicate (synthesized at acidic reaction conditions (pH 2) and at higher temperature: 70° C. to 90° C.).

Figure 10C:
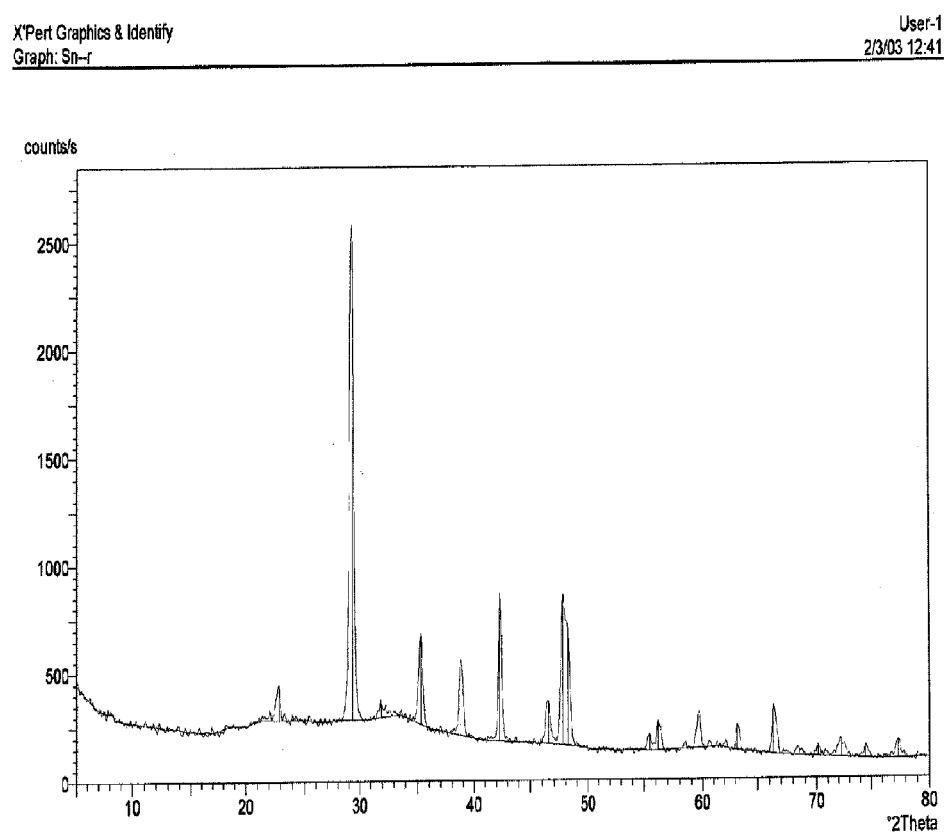

FIG. 10C and FIG. 10D: XRD (X-ray diffraction) pattern of silver silicate (synthesized at acidic reaction conditions (pH 2) and at higher temperature: 70° C. to 90° C.).

FIG. 11A: Composition analysis of manganese silicate (synthesized at neutral (pH 6-7) reaction conditions) using EDAX attached to SEM (Scanning Electron Microscope).

Figure 11B:
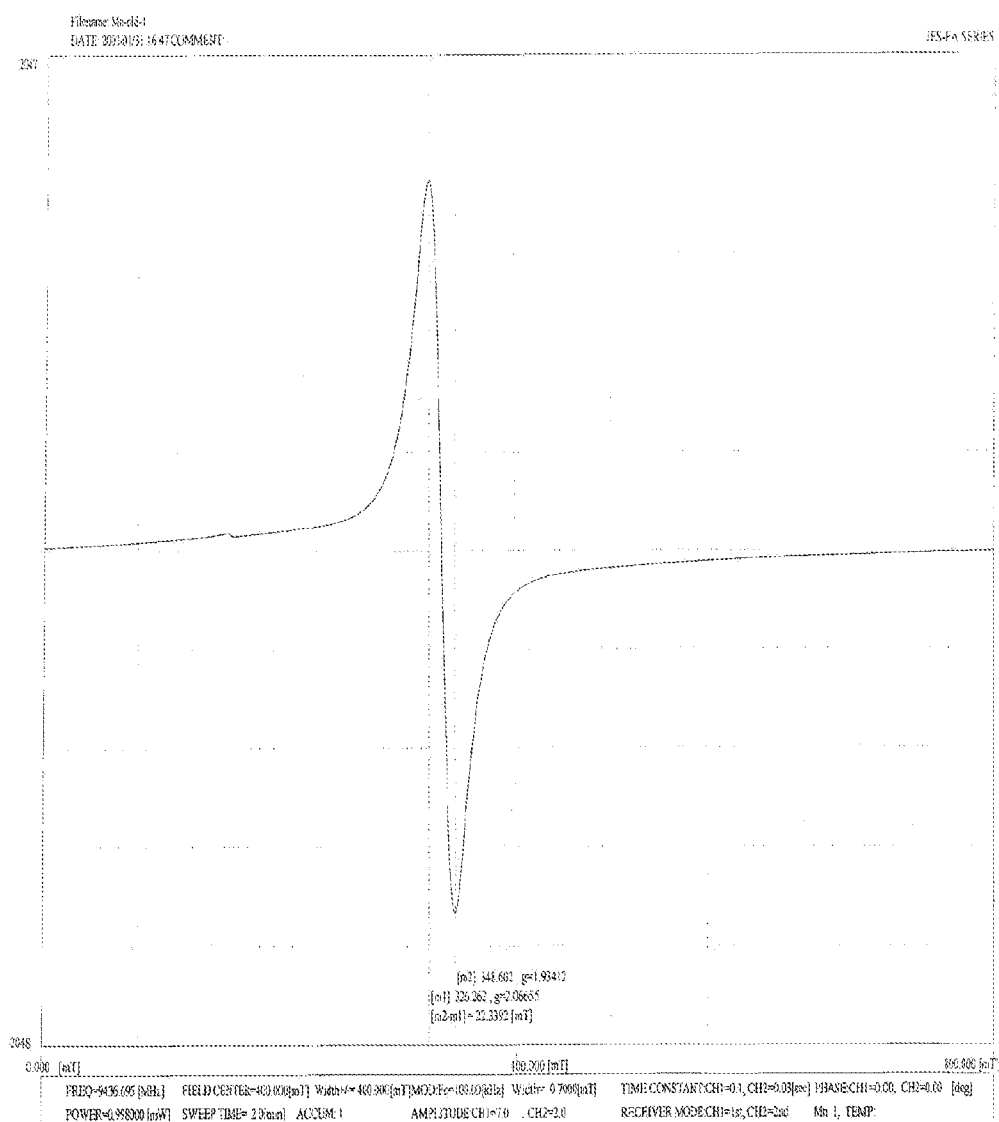

FIG. 11B: ESR (Electron spin resonance) spectrometer analysis of manganese silicate (synthesized at neutral (pH 6-7) reaction conditions).

Figure 11C:
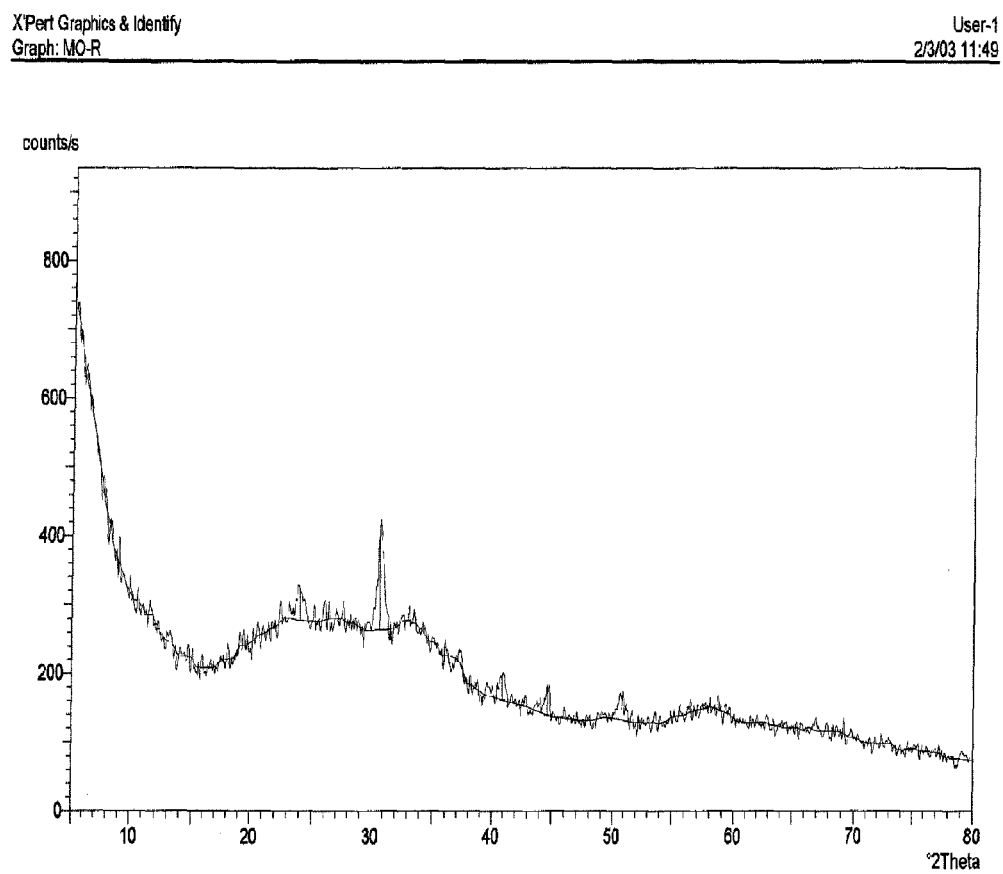

FIG. 11C and FIG. 11D: XRD (X-ray diffraction) pattern of manganese silicate (synthesized at neutral (pH 6-7) reaction conditions).

FIG. 12A: Composition analysis of manganese silicate (synthesized at extreme acidic reaction conditions (below pH 2) and at higher temperature: 70° C. to 90° C.) using EDAX attached to SEM (Scanning Electron Microscope).

Figure 12B:
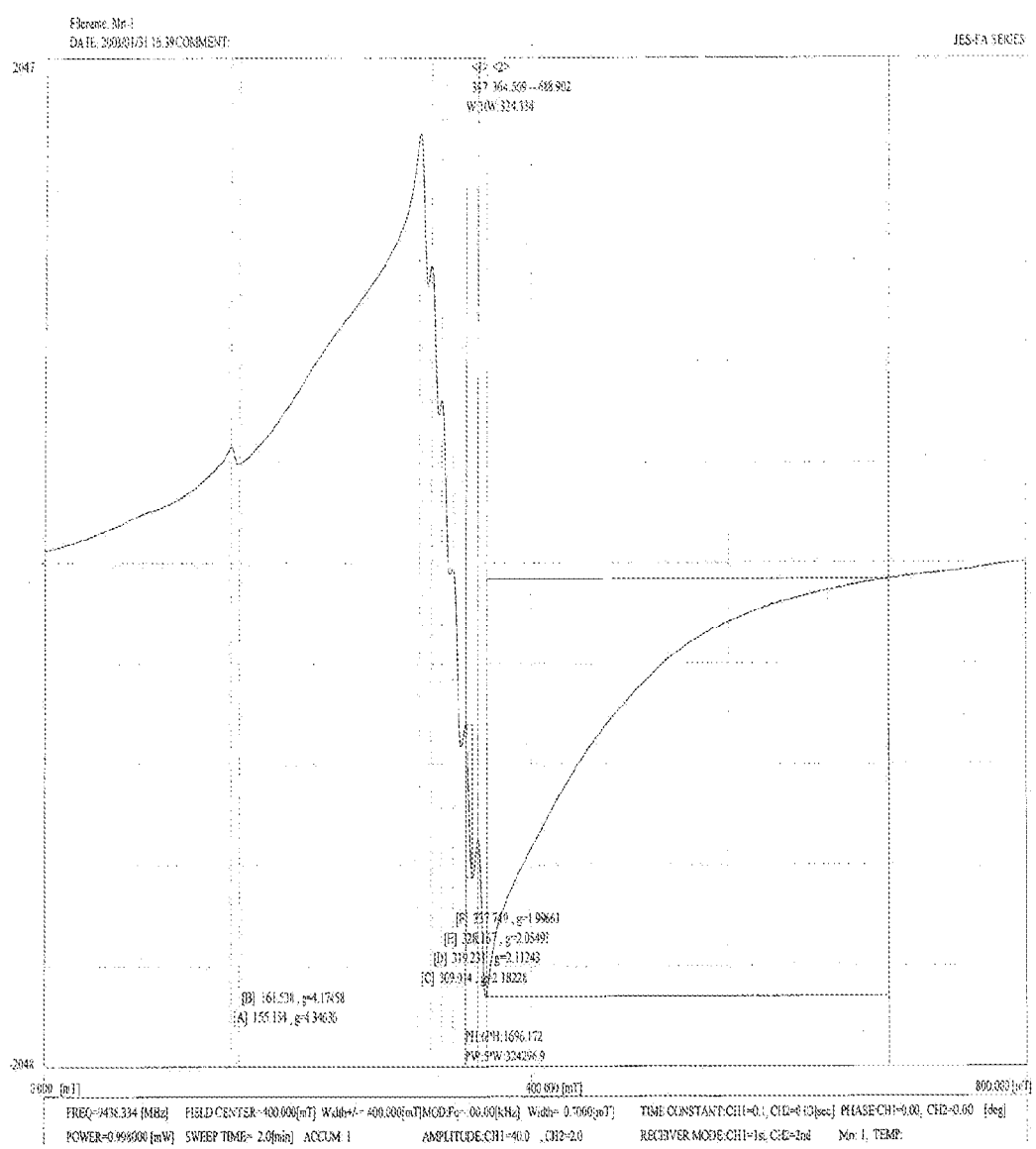

FIG. 12B: ESR (Electron spin resonance) spectrometer analysis of manganese silicate (synthesized at extreme acidic reaction conditions (below pH 2) and at higher temperature: 70° C. to 90° C.).

Figure 12C:
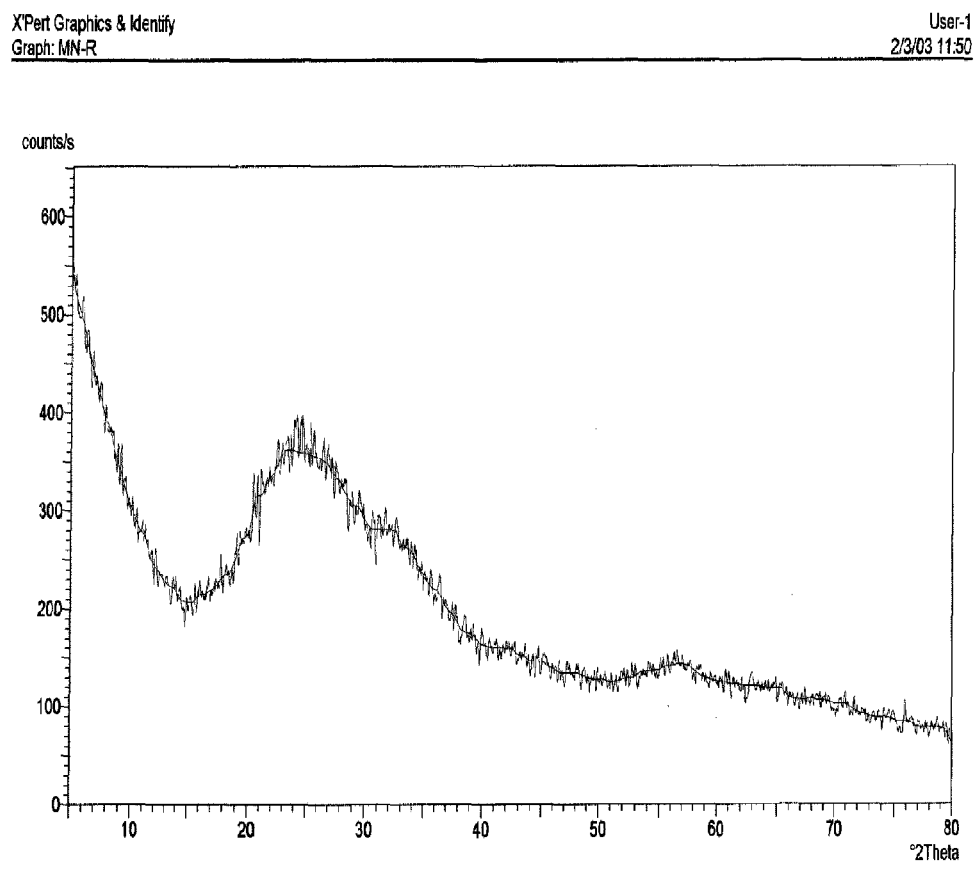

FIG. 12C and FIG. 12D: XRD (X-ray diffraction) pattern of manganese silicate (synthesized at extreme acidic reaction conditions (below pH 2) and at higher temperature: 70° C. to 90° C.).

FIG. 13A: Composition analysis of zirconium silicate (synthesized at neutral (pH 6-7) reaction conditions) using EDAX attached to SEM (Scanning Electron Microscope.

Figure 13B:
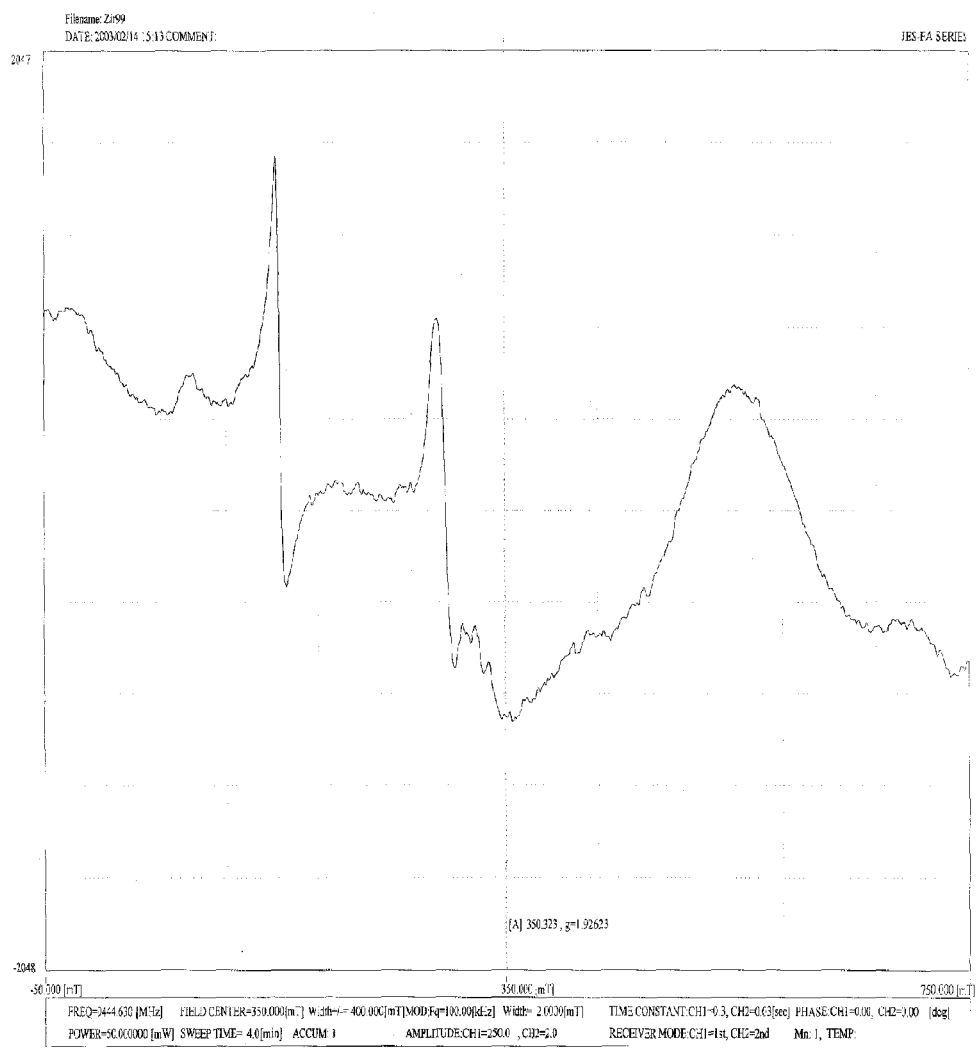

FIG. 13B: ESR (Electron spin resonance) spectrometer analysis of zirconium silicate (synthesized at neutral (pH 6-7) reaction conditions).

Figure 13C:
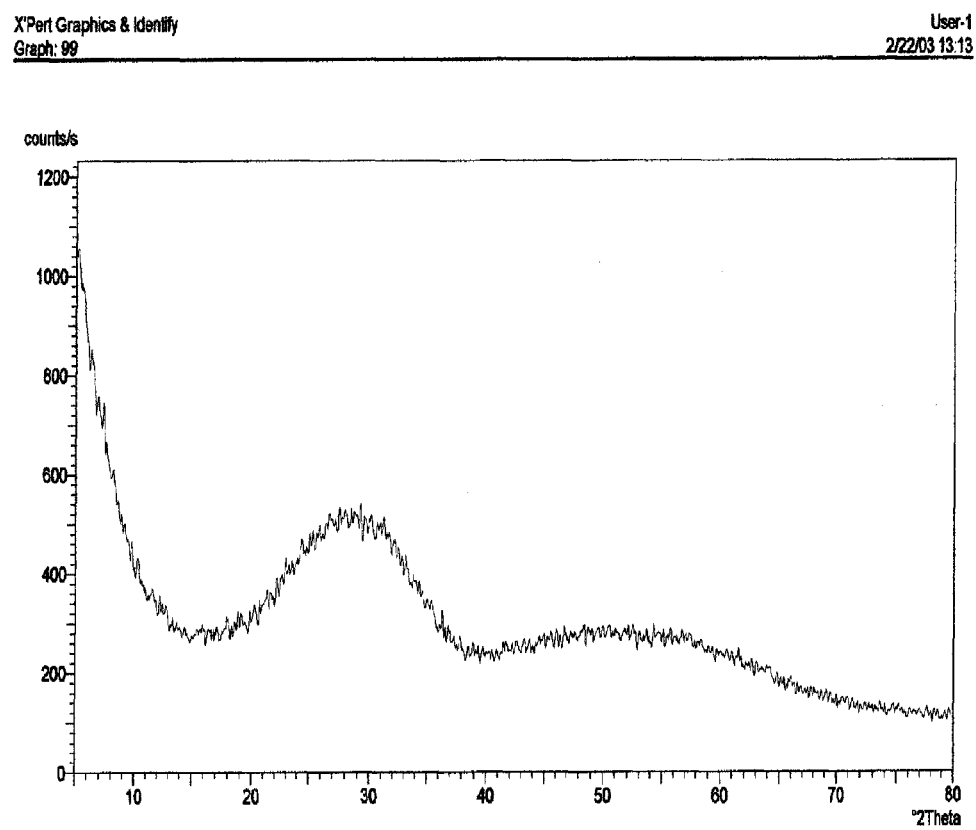

FIG. 13C and FIG. 13D: XRD (X-ray diffraction) pattern of zirconium silicate (synthesized at neutral (pH 6-7) reaction conditions).

FIG. 14A: Composition analysis of zirconium silicate (synthesized at extreme acidic reaction conditions (below pH 2) and at higher temperature: 70° C. to 90° C.) using EDAX attached to SEM (Scanning Electron Microscope).

Figure 14B:
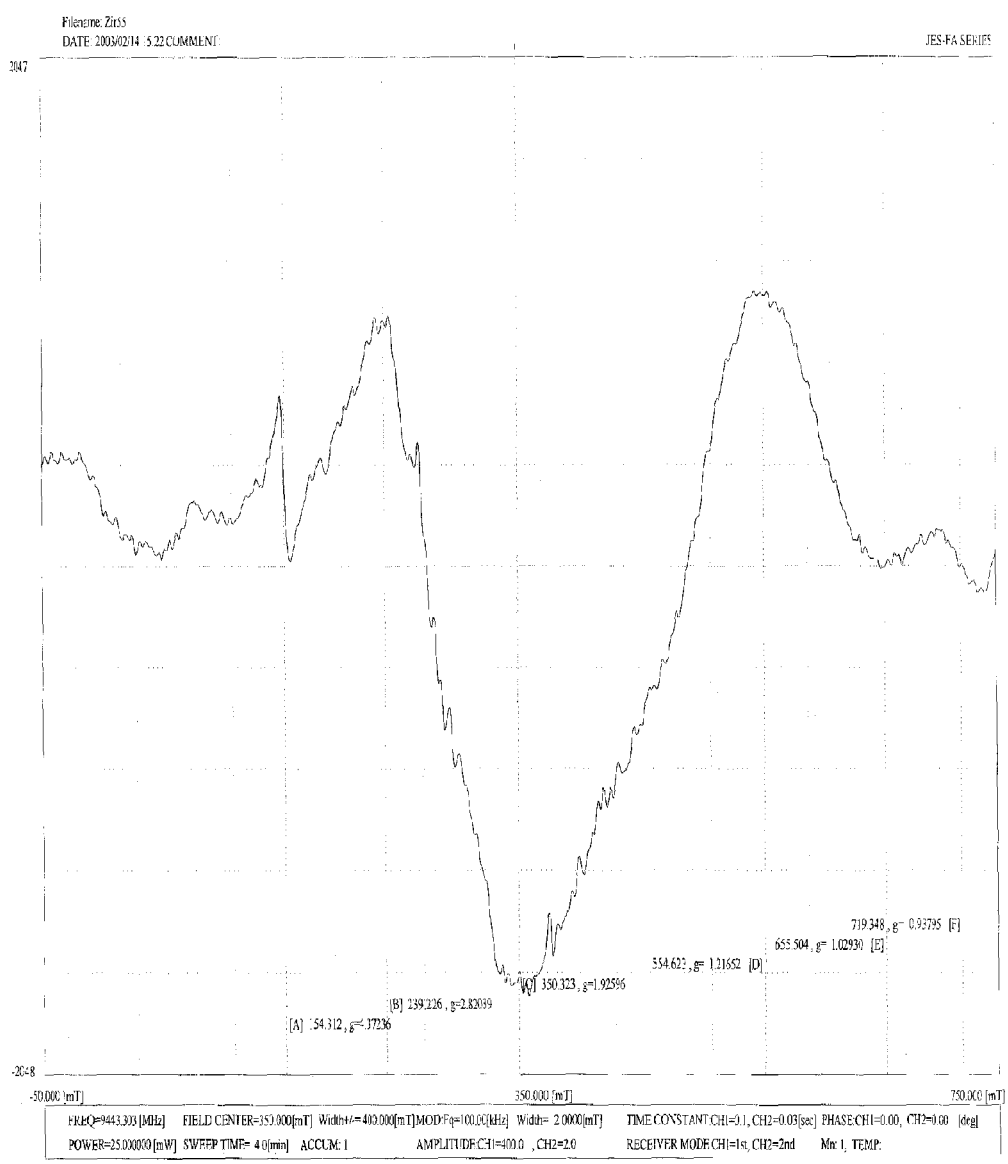

FIG. 14B: ESR (Electron spin resonance) spectrometer analysis of zirconium silicate (synthesized at extreme acidic reaction conditions (below pH 2) and at higher temperature: 70° C. to 90° C.).

Figure 14C:
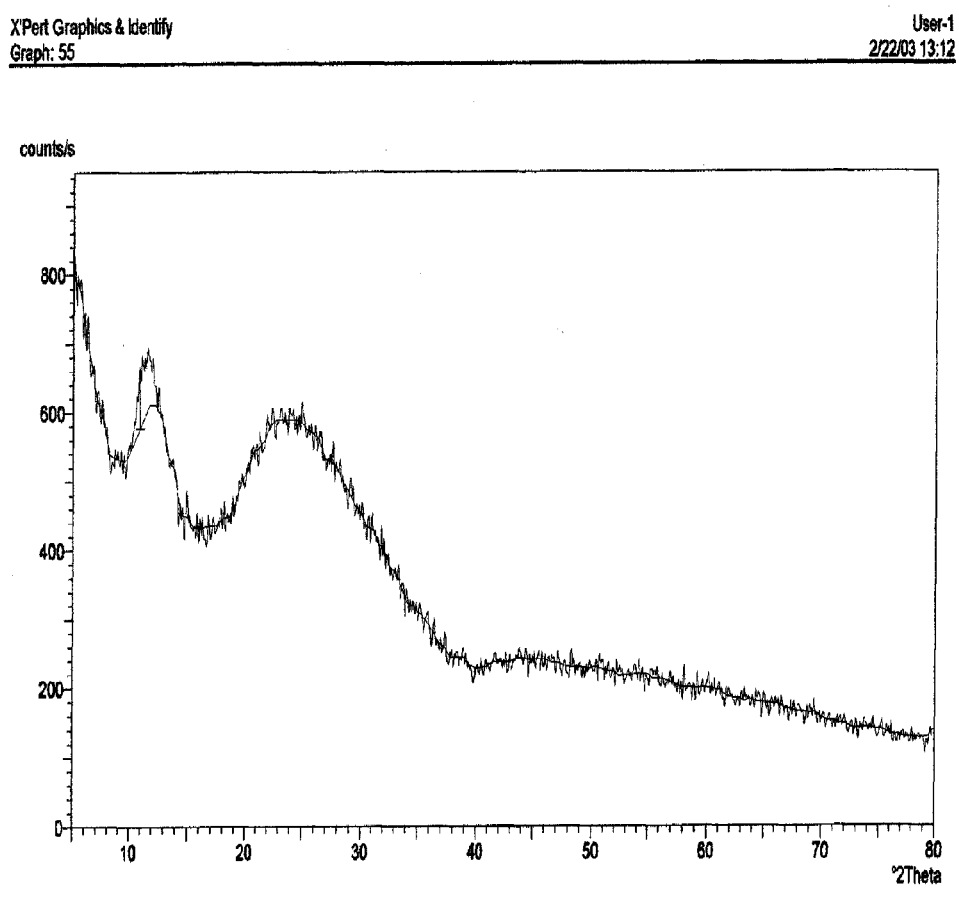

FIG. 14C and FIG. 14D: XRD (X-ray diffraction) pattern of zirconium silicate (synthesized at extreme acidic reaction conditions (below pH 2) and at higher temperature: 70° C. to 90° C.).

*The functional transition metal silicates were analyzed by SEM/EDAX (ESEM, XL-30), ESR (JEOL, JES-FA-200), AND XRD (PHLIPS, PW-1830) to understand the composition, structure, etc., details.

Now applicant provide the following specific description by way of examples and illustrations of the invention and this should not be construed to limit the scope of the invention in any manner.

Synthesis of Cupric Silicates

Synthesis of cupric silicate will be described in detail with the following illustrations 1. Synthesis of Cupric Silicate at Acidic Reaction Conditions:

10 ml of sodium silicate solution (0.5 g/ml) having 2:1 silicate to sodium ratio was added to 100 ml of cupric chloride solution ($CuCl_2$ $2H_2O$, 0.5 g/ml). The reaction condition is acidic. The resultant precipitate obtained after removal of supernatant was dried after thoroughly washing with distilled or deionized water.

The silicate to copper ratio was 1:5.15 as revealed from analysis of this cupric silicate by using EDAX attached to SEM (Scanning Electron Microscope) and further confirmed by analyzing with AAS or ICP-AES (FIG. 1-A).

This Cupric silicate when subjected to analysis by electron spin resonance spectrometer resulted in characteristic g values of the peaks, which were presented below (as shown in FIG. 1-B and Table 1).

A) 4.32481 B) 2.55205 C) 2.31749 D) 2.08807 E) 2.04673

This Cupric silicate when subjected to X-ray Diffraction analysis resulted in 8 peaks as evidenced in FIG. 4, which shows 3 significant peaks, and peak height, (counts/s) and Angle (° 2 theta) of these 3 peaks were presented below (as shown in FIG. 1-C, and Table 1).

1) 2128.25 and 16.28197 2) 1593.74 and 32.29018 3) 1470.73 and 39.79307

This cupric silicate decontaminated arsenic up to 42.5%, when 500 mg of this material was treated by mixing with 1 liter of 2.5 ppm arsenic solution prepared from sodium arsenate (Table 1).

This cupric silicate disinfected $2.72 \times 10^5$ coliform bacteria from drinking water, when 10 mg of cupric silicate was added to 1 liter of coliform contaminated drinking water (Table 1).

This cupric silicate inhibited the growth of gram positive and gram-negative bacteria such as *E. Coli, Staphylococcus aureus, Pseudomonas aeruginosa,* and *Bacillus subtilis* when cupric silicate (0.25%) was mixed with bacterial growth media (Table 3).

Even at a concentration of 0.06% and 0.125% of this cupric silicate in growth media inhibited the growth of *E. coli* (Table 4).

This Cupric silicate inhibited fungal growth of a) *Sclerotium rolfsii* b) *Rhizoctonia solani* c) *Fusarium oxysporium* d) *Pyricularia oryzae* (Table 6), up to 32.93, 73.2, 76.8, and 100% respectively, with 0.25% material concentration mixed in growth media of fungus (Table 6).

Viral disinfection nature of this Cupric silicate was analyzed using Bacteriophages and this cupric silicate disinfected the viruses.

The phages used in this study, their isoelectric points (pI) and their hosts are as follows: MS2 (ATCC 155597-B1), pI 3.9, *Escherichia coli* C-3000 (ATCC 15997); NX-174 (ATCC 13706-B1) pI6.6, *E. Coli* (ATCC 13706); and PRD-1, pI 4.2, *Salmonella typhimurium* (ATCC 19585). Phages were assayed as plaque-forming units (PFU) using their respective hosts and a soft-agar overlay described by Snustad, S. A., and D. S. Dean (Genetic experiments with bacterial viruses, 1971, W. H. Freeman and Co., San Francisco).

Batch Absorption Studies:

Three hundred milligrams of the cupric silicate was aseptically weighed and placed into each of three sterile 50 ml conical bottom centrifuge tube. Aliquots as the bacteriophage stocks were added to 100 ml of sterile deionized water (DI, Ph 7.8-8.4) to achieve final concentration of approximately $10^5$ pfu/ml. Fifteen milliliter of the seeded DI was added to each of the three tubes containing the material. A control tube containing seeded DI and no material was also prepared. The tubes were sealed then placed on a rotary shaker (Red Rotor PR70/75, Hoofer Scientific, CA) for 10 min at medium speed (0.8 rps). The tubes were removed and centrifuged at 3000 g for 5 min. Aliquots of the supernatant and the control seeded DI were removed, serially diluted, and assayed for the respective Bacteriophages as described above.

Cupric silicate decontaminated about 90% Bacteriophage viruses such as MS-2, ØX174 and PRD-1 (as shown in table 7).

This cupric silicate exhibited chemical pollutant decontamination property when this cupric silicate (500 mg) was added to trihalomethanes (such as chloroform, 1,1,1, trichloroethane, tetrachloroethylene, trichloroethylene, bromodichloroethane, dibromochloroethane, tetrachloroethylene, bromoform, 1,2, dichlor-3-bromopropane) dissolved in water. After thorough mixing of cupric silicate with 8.950 ppm trihalomethanes containing water, the supernatant analysis after precipitation of cupric silicate revealed that cupric silicate decontaminated trihalomethanes. Cupric silicate decontaminated 5.4 ppm of trihalomethanes out of 8.95 ppm trihallomethanes as shown in (Table 8).

2. Synthesis of Cupric Silicate at Acidic Reaction Conditions and at Higher Temperature (70° C. to 90° C.):

50 ml of sodium silicate solution (0.5 g/ml) having 1:1 silicate to sodium ratio was added to 100 ml cupric chloride solution (0.5 g/ml). After thorough mixing the reactants were heated up to 70° C. to 90° C. and kept overnight for 12 hours. The precipitate obtained was extensively washed with distilled or deionized water and dried in oven at 100° C.

The silicate to copper ratio was 1:0.78, as revealed from analysis of cupric silicate by using EDAX attached to scanning electron microscope and further confirmed by analyzing with AAS or ICP-AES (FIG. 2-A).

This Cupric silicate when subjected to analysis by electron spin resonance spectrometer resulted in characteristic g values of the peaks, which were presented below (as shown in FIG. 2-B, and Table 1).

A) 2.23480 B) 2.06456

This Cupric silicate when subjected to X-ray Diffraction analysis resulted in 7 peaks as evidenced in FIG. 6, which shows 3 significant peaks, and peak height, (counts/s) and Angle (°2 theta) of these 3 peaks, which were presented below (as shown in FIG. 2-C and Table 1).

1) 835.63 and 16.20057
2) 706.74 and 32.23910
3) 502.52 and 39.57159

This Cupric silicate decontaminated arsenic up to 55.8%, when 500 mg of this material was treated by mixing with 1 liter of 2.5 ppm arsenic solution prepared from sodium arsenate (as shown in Table 1).

This cupric silicate disinfected $2.72 \times 10^5$ coliform bacteria from drinking water, when 10 mg of cupric silicate was added to 1 liter of coliform contaminated drinking water (Table 1).

3. Synthesis of Cupric Silicate at Neutral Reaction Conditions (pH: 6-7):

Appropriate amount of sodium silicate solution (0.5 g/ml) having 1:1 silicate to sodium ratio was added to 100 ml of cupric chloride (0.5 g/ml) solution to obtain neutral pH condition. The resultant precipitate containing cupric silicate was obtained after removal of supernatant and dried after thoroughly washing with distilled or deionized water.

The silicate to copper ratio was 1:1, as revealed from analysis of this cupric silicate by using EDAX attached to scanning electron microscope and by further confirmed by analyzing with AAS or ICP-AES (FIG. 3-A).

This cupric silicate when subjected to analysis by electron spin resonance spectrometer resulted in characteristic g values of the peaks, which were presented below (as shown in FIG. 3-B, and Table 1).

A) 3.10383 B) 2.36522 C) 2.0467 D) 1.21887 E) 0.96688

This cupric silicate when subjected to X-ray diffraction analysis resulted in 6 peaks as evidenced in FIG. 3-C, which shows 3 significant peaks, and peak height, (counts/s) and angle (°2 theta) of these 3 peaks were presented below (as shown in FIG. 3-C and Table 1).
1. 940.90 and 16.19577
2. 764.43 and 32.29276
3. 694.85 and 39.77809

This cupric silicate decontaminated arsenic up to 27.7%, when 500 mg of this material was treated by mixing with 1 liter of 2.5 ppm arsenic solution prepared from sodium arsenate (Table 1).

This cupric silicate disinfected $2.72 \times 10^5$ coliform bacteria from drinking water, when 10 mg of cupric silicate was added to 1 liter of coliform contaminated drinking water (Table 1).

This cupric silicate inhibited fungal growth of a) *Sclerotium rolfsii* b) *Rhizoctonia solani* c) *Fusarium oxysporium* d) *Pyricularia oryzae* (Table 6), up to 24.7, 59.0, 68.3 and 88.5% respectively, with 0.25% material concentration present in growth media of fungus.

4. Synthesis of Cupric Silicate at Basic Reaction Conditions (pH: 10-11):

Required amount of sodium silicate solution (0.5 g/ml) having 1:1 silicate to sodium ratio was added to 100 ml of cupric chloride solution (0.5 g/ml) to obtain basic pH condition (10-11 pH). The resultant precipitate was obtained after removal of supernatant and dried after thoroughly washing with distilled or deionized water.

The silicate to copper ratio was 1:0.83 as revealed from analysis of this cupric silicate by using EDAX attached to scanning electron microscope and further confirmed by analyzing with AAS or ICP-AES (FIG. 4-A).

This cupric silicate when subjected to analysis by electron spin resonance spectrometer resulted in characteristic g values of the peaks, which were presented below (as shown in FIG. 4-B, and Table 1).
A) 3.71806 B) 3.23001 C) 2.61681

This cupric silicate when subjected to X-ray diffraction analysis resulted in 3 peaks as evidenced in FIG. 4-C, which shows 1 significant peak, and peak height, (counts/s) and angle (° 2 theta) of this peak is presented below (as shown in FIG. 4-C and Table 1).
1) 152.74 and 26.64983

This cupric silicate decontaminated arsenic up to 8%, when 500 mg of this material was treated by mixing with 1 liter of 2.5 ppm arsenic solution prepared from sodium arsenate (Table 1).

This cupric silicate disinfected 21.69% only out of $2.72 \times 10^5$ coliform bacteria from drinking water, when 250 mg of cupric silicate was added to 1 liter of coliform contaminated drinking water (Table 1).

5. Synthesis of Cupric Silicate Obtained by Addition of 10 ml of 36% HCl into Reaction Medium at Extreme Acidic Reaction Conditions (below 2 pH):

10 ml of 36% analytical grade HCl was added to 100 ml of cupric chloride (0.5 g/ml) solution. To these acidic cupric chloride solutions, 50 ml of sodium silicate solution (0.5 g/ml) having 1:1 silicate to sodium ratio was added. After thorough mixing, the reactants were heated up to 70° C. to 90° C. and kept overnight for 12 hours. The precipitate obtained was extensively washed with distilled or deionized water and dried in oven at 100° C. The silicate to copper ratio was 1:0.53 as revealed from analysis of this cupric silicate by using EDAX attached to scanning electron microscope and further confirmed by analyzing with AAS or ICP-AES (FIG. 5-A).

This cupric silicate when subjected to analysis by electron spin resonance spectrometer resulted in characteristic g values of the peaks, which were presented below (as shown in FIG. 5-B and Table 1).
A) 2.18421 B) 2.06874 C) 1.21231

This cupric silicate when subjected to X-ray diffraction analysis resulted in 6 peaks as evidenced in FIG. 5-C, which shows 3 significant peaks, and peak height, (counts/s) and angle (° 2 theta) of these 3 peaks were presented below (as shown in FIG. 5-C, and Table 1).
1) 400.70 and 16.19872
2) 394.77 and 32.27956
3) 330.02 and 39.71761

This cupric silicate decontaminated arsenic up to 42%, when 500 mg of this material was treated by mixing with 1 liter of 2.5 ppm arsenic solution prepared from sodium arsenate (Table 1).

This cupric silicate disinfected $2.72 \times 10^5$ coliform bacteria from drinking water, when 10 mg of cupric silicate was added to 1 liter of coliform contaminated drinking water (Table 1).

6. Synthesis of Cupric Silicate Obtained by Addition of 20 ml of 36% HCl into Reaction Medium at Extreme Acidic Reaction Conditions (below pH 2):

20 ml of 36% analytical grade HCl was added to 100 ml of cupric chloride (0.5 g/ml) solution. To these acidic cupric chloride solutions, 50 ml of sodium silicate solution (0.5 g/ml) having 1:1 silicate to sodium ratio was added. After thorough mixing the reactants were heated up to 70° C. to 90° C. and kept overnight for 12 hours. The precipitate obtained was extensively washed with distilled or deionized water and dried in oven at 100° C.

The silicate to copper ratio was 1:0.34 as revealed from analysis of this cupric silicate by using EDAX attached to scanning electron microscope and further confirmed by analyzing with AAS or ICP-AES (FIG. 6-A).

This cupric silicate when subjected to analysis by electron spin resonance spectrometer resulted in characteristic g values of the peaks were presented below (as shown in FIG. 6-B, and Table 1).
A) 2.15561 B) 2.03614

This cupric silicate when subjected to X-ray diffraction analysis resulted in 7 peaks as evidenced in FIG. 6-C, which shows 3 significant peaks, and peak height, (counts/s) and angle (° 2 theta) of these 3 peaks were presented below (as shown in FIG. 6-C and Table 1).
1) 541.23 and 16.26305
2) 414.21 and 32.36589
3) 365.45 and 39.85131

This cupric silicate decontaminated arsenic up to 27.7%, when 500 mg of this material was treated by mixing with 1 Liter of 2.5 ppm arsenic solution prepared from sodium arsenate (Table 1).

This cupric silicate disinfected $2.72 \times 10^5$ coliform bacteria from drinking water, when 10 mg of cupric silicate was added to 1 liter of coliform contaminated drinking water (Table 1).

Synthesis of Zinc Silicates:

7) Synthesis of Zinc Silicates at Neutral Reaction Conditions (pH: 6-7):

Appropriate amount of sodium silicate solution (0.5 g/ml) having 2:1 silicate to sodium ratio was added to 100 ml of zinc chloride ($ZnCl_2$, 0.5 g/ml) solution to obtain neutral pH condition. The resultant precipitate containing zinc silicate was obtained after removal of supernatant and dried after thoroughly washing with distilled or deionized water.

The silicate to zinc ratio was 1:12.13 as revealed from analysis of this zinc silicate by using EDAX attached to scanning electron microscope and further confirmed by analyzing with AAS or ICP-AES (FIG. 7-A).

This zinc silicate when subjected to analysis by electron spin resonance spectrometer resulted in characteristic g values of the peaks, which were presented below (as shown in FIG. 7-B, and Table 2).
A) 5.49809 B) 4.55342 C) 2.54593 D) 2.10091 E) 2.05499

This zinc silicate when subjected to X-ray diffraction analysis resulted in 8 peaks as evidenced in FIG. 7-C, which shows 3 significant peaks and peak height, (counts/s) and Angle (° 2 theta) of these 3 peaks were presented below (as shown in FIG. 9 and Table 2).
1) 444.15 and 32.75904
2) 307.02 and 59.58455
3) 263.36 and 28.27636

This zinc silicate decontaminated arsenic up to 98.7%, when 1.0 gram of this material was treated by mixing with 1 Liter of 2.5 ppm arsenic solution prepared from sodium arsenate (Table 2).

This zinc silicate disinfected 96% out of $2.72\times10^5$ coliform bacteria from drinking water, when 250 mg of zinc silicate was added to 1 liter of coliform contaminated drinking water (Table 2).

Zinc silicate at a concentration of 0.25% in the growth media exhibited bactericidal property by inhibiting the growth of *Staphylococcus aureus* (as shown in table 5).

8) Synthesis of Zinc Silicates at Extreme Acidic Reaction Conditions (Below 2 pH):

10 ml of 36% analytical grade HCl was added to 100 ml of zinc chloride solution (0.5 g/ml). 50 ml of sodium silicate solution (0.5 g/ml) having 2:1 silicate to sodium ratio was added to the HCl containing zinc chloride solution. After thorough mixing, the reactants were heated up to 70° C. to 90° C. and kept overnight for 12 hours. The resultant precipitate containing zinc silicate was obtained after removal of supernatant and dried after thoroughly washing with distilled or deionized water.

The silicate to zinc ratio was 1:2.46 as revealed from analysis of this zinc silicate by using EDAX attached to scanning electron microscope and further confirmed by analyzing with AAS or ICP-AES (FIG. 8-A), This Zinc silicate when subjected to analysis by electron spin resonance spectrometer resulted in characteristic g values of the peaks, which were presented below (as shown in FIG. 8-B, and Table 2).
A) 4.38410 B) 4.01910 C) 2.53191 D) 1.87886 E) 2.01793

This zinc silicate when subjected to X-ray Diffraction analysis resulted in 26 peaks as evidenced in FIG. 8-C, which shows 3 significant peaks and peak height, (counts/s) and angle (° 2 theta) of these 3 peaks were presented below (as shown in FIG. 8-C and Table 2).
1) 2079.88 and 11.07467
2) 835.44 and 33.52527
3) 664.98 and 32.88120

This zinc silicate decontaminated arsenic up to 72.3%, when 1.0 gram of this material was treated by mixing with 1 liter of 2.5 ppm arsenic solution prepared from sodium arsenate (Table 2).

This zinc silicate disinfected 99% out of $2.72\times10^5$ coliform bacteria from drinking water, when 250 mg of zinc silicate was added to 1 liter of coliform contaminated drinking water (Table 2).

Synthesis of Silver Silicates:

9) Synthesis of Silver Silicates at Neutral Reaction Conditions (6-7 pH):

100 ml of silver nitrate ($AgNO_3$, 0.5 g/ml) solution was mixed with required amount of sodium silicate solution (1:1=sodium:silica, 0.5 g/ml) having 2:1 silica, transition metal ratio to attain neutral pH in the reaction. After addition, of reactants they were thoroughly mixed and the resultant precipitate was obtained by decanting the supernatant. The precipitate was washed extensively with distilled or deionized water and dried in oven at 100° C.

The silicate to silver ratio was 1:19.5 as revealed from analysis of this silver silicate by using EDAX attached to scanning electron microscope and further confirmed by analyzing with AAS or ICP-AES (FIG. 9-A).

This silver silicate when subjected to analysis by electron spin resonance spectrometer resulted in characteristic g values of the peaks, which were presented below (as shown in FIG. 9-B, and Table 2).
A) 4.36796 B) 2.37847 C) 3.95509 D) 2.04657

This silver silicate when subjected to X-ray diffraction analysis resulted in 19 peaks as evidenced in FIG. 9-C, which shows 3 significant peaks and peak height, (counts/s) and Angle (° 2 theta) of these 3 peaks were presented below (as shown in FIG. 9-C and Table 2).
1) 3945.11 and 32.29885
2) 2421.27 and 46.27446
3) 1835.66 and 27.89129

This silver silicate decontaminated arsenic up to only 4.5%, when 1.0 gram of this material was treated by mixing with 1 liter of 2.5 ppm arsenic solution prepared from sodium arsenate (Table 2).

This silver silicate disinfected $2.72\times10^5$ coliform bacteria from drinking water, when 5 mg of silver silicate was added to 1 liter of coliform contaminated drinking water (shown in Table 2).

10) Synthesis of Silver Silicates at Acidic Reaction Conditions (pH: 2):

8 ml of nitric acid solution (69-70%) was added to 50 ml of silver nitrate (0.5 g/ml) solution. Required amount of sodium silicate (1:1=sodium:silica, 0.5 g/ml) solution, 2:1 silica, transition metal ratio was added to this acidified silver nitrate solution to obtain 2 pH. After thorough mixing, the reactants were heated up to 70° C. to 90° C. and kept overnight for 12 hours. The resultant precipitate was washed extensively with distilled or deionized water and dried in oven at 100° C.

The silicate to silver ratio was 1:1.04 as revealed from analysis of this silver silicate by using EDAX attached to scanning electron microscope and further confirmed by analyzing with AAS or ICP-AES (FIG. 10-A).

This silver silicate when subjected to analysis by electron spin resonance spectrometer resulted in characteristic g values of the peaks, which were presented below (as shown in FIG. 10-B, and Table 2).
A) 4.37171 B) 4.04714 C) 1.98189

This silver silicate when subjected to X-ray diffraction analysis resulted in 19 peaks as evidenced in FIG. 10-C, which shows 3 significant peaks and peak height, (counts/s) and angle (° 2 theta) of these 3 peaks were presented below (as shown in FIG. 10-C and Table 2).
1) 2217.87 and 29.33483
2) 684.55 and 47.68093
3) 674.27 and 42.31091

This silver silicate decontaminated arsenic up to 99.0%, when 1.0 gram of this material was treated by mixing with 1 Liter of 2.5 ppm arsenic solution prepared from sodium arsenate (Table 2).

This silver silicate disinfected $2.72\times10^5$ coliform bacteria from drinking water, when 5 mg of silver silicate was added to 1 liter of coliform contaminated drinking water (Table 2).

Synthesis of Manganese Silicates:

11) Synthesis of Manganese Silicates at Neutral Reaction Conditions (pH: 6-7):

100 ml of Manganese chloride ($MnCl_2$ $4H_2O$, 0.5 g/ml) solution was mixed with required amount of sodium silicate solution (1:1=sodium:silica, 0.5 g/ml) to obtain neutral pH (6-7) in the reaction medium. After addition, they were thoroughly mixed and the resultant precipitate was obtained by decanting the supernatant. The precipitate was washed extensively with distilled or deionized water and dried in oven at 100° C.

The silicate to manganese ratio was 1:1.94 as revealed from analysis of this manganese silicate by using EDAX attached to scanning electron microscope and further confirmed by analyzing with AAS or ICP-AES (FIG. 11-A).

This manganese silicate when subjected to analysis by electron spin resonance spectrometer resulted in characteristic g values of the peaks, which were presented below (as shown in FIG. 11-B, and Table 2).

A) 1.93412 B) 2.06655

This manganese silicate when subjected to X-ray diffraction analysis resulted in 5 peaks as evidenced in FIG. 11-C, which shows one significant peak and peak height, (counts/s), Angle (° 2 theta) of this single peak were presented below (as shown in FIG. 11-C and Table 2).

a) 148.04 and 30.65087

This manganese silicate decontaminated arsenic up to 12.4%, when 1.0 gram of this material was treated by mixing with 1 liter of 2.5 ppm arsenic solution prepared from sodium arsenate (Table 2).

This manganese silicate disinfected 51% out of $2.72 \times 10^5$ coliform bacteria from drinking water, when 500 mg of manganese silicate was added to 1 liter of coliform contaminated drinking water (Table 2).

12) Synthesis of Manganese Silicates at Extreme Acidic Reaction Conditions (Below 2 pH):

10 ml of 36% HCl was added to 100 ml of manganese chloride solution (0.5 g/ml). Sodium silicate solution (1:1=sodium:silica, 0.5 g/ml,), 50 ml was added to acidified manganese chloride solution. After thorough mixing, the reactants were heated up to 70° C. to 90° C. and kept overnight for 12 hours. The resultant precipitate was washed extensively with distiller water or deionized water and dried in oven at 100° C.

The silicate to manganese ratio was 1:1:09 as revealed from analysis of this manganese silicate by using EDAX attached to scanning electron microscope and further confirmed by analyzing with AAS or ICP-AES (FIG. 12-A).

This manganese silicate when subjected to analysis by electron spin resonance spectrometer resulted in characteristic g values of the peaks, which were presented below (as shown in FIG. 12-B, and Table 2).

A) 4.34636 B) 4.17458 C) 2.18228 D) 2.11243 E) 2.05491 F) 1.999661

This manganese silicate when subjected to X-ray diffraction analysis resulted in one peak as evidenced in FIG. 12-C, which shows one significant peak and peak height (counts/s) and angle (° 2 theta) of this peak were presented below (as shown in FIG. 12-C and Table 2).

a) 32.88 and 24.65599

This manganese silicate decontaminated arsenic up to 10.3%, when 1.0 gram of this material was treated with 1 liter of 2.5 ppm arsenic solution prepared from sodium arsenate (Table 2).

This manganese silicate disinfected 58% out of $2.72 \times 10^5$ coliform bacteria from drinking water, when 500 mg of manganese silicate was added to 1 liter of coliform contaminated drinking water (Table 2).

Synthesis of Zirconium Silicates:

13) Synthesis of Zirconium Silicates at Neutral Reaction Conditions (pH: 6-7)

To 100 ml of zirconium oxychloride solution ($ZrOCl_2$ $8H_2O$, 0.5 g/ml), required amount of sodium silicate solution (1:1=sodium:silica, 0.5 g/ml) was added to obtain neutral pH. After addition, they were thoroughly mixed and the resultant precipitate was obtained by decanting the supernatant. The precipitate was washed extensively with distilled or deionized water and dried in oven at 100° C.

The silicate to zirconium ratio was 1:2.90 as revealed from analysis of this zirconium silicate by using EDAX attached to scanning electron microscope and further confirmed by analyzing with AAS or ICP-AES (FIG. 13-A).

This zirconium silicate when subjected to analysis by electron spin resonance spectrometer resulted in characteristic g values of the peaks, which were presented below (as shown in FIG. 13-B, and Table 2).

A) 4.42797 B) 4.18272 C) 2.24547 D) 2.30425 E) 2.18961 F) 1.23086

This zirconium silicate when subjected to X-ray diffraction analysis resulted no peak as evidenced in FIG. 13-C.

This zirconium silicate decontaminated arsenic up to 28.9%, when 1.0 gram of this material was treated by mixing with 1 liter of 2.5 ppm arsenic solution prepared from sodium arsenate (Table 2).

This zirconium silicate disinfected 2% out of $2.72 \times 10^5$ coliform bacteria from drinking water, when 250 mg of zirconium silicate was added to 1 liter of coliform contaminated drinking water (Table 2).

14) Synthesis of Zirconium Silicates at Extreme Acidic Reaction Conditions (Below 2 pH):

To 100 ml of zirconium oxychloride solution, 10 ml of 36% HCl and sodium silicate solution (1:1=sodium:silica, 0.5 g/ml) 50 ml were added and mixed well. After thorough mixing, the reactants were heated up to 70° C. to 90° C. and kept overnight for 12 hours. The resultant precipitate was washed extensively with distilled or deionized water and dried in oven at 100° C.

The silicate to zirconium ratio was 1:0.77 as revealed from analysis of this zirconium silicate by using EDAX attached to scanning electron microscope and further confirmed by analyzing with AAS or ICP-AES (FIG. 14-A).

This zirconium silicate when subjected to analysis by electron spin resonance spectrometer resulted in characteristic g values of the peaks, which were presented below (as shown in FIG. 14-B, and Table 2).

A) 4.37236 B) 2.82039 C) 1.92596 D) 1.21652 E) 1.02930 F) 0.93795

This zirconium silicate when subjected to X-ray diffraction analysis resulted in 1 peak as evidenced in FIG. 14-C, which shows one significant peak, and peak height (counts/s) and angle (° 2 theta) of this peak were presented below (as shown in FIG. 14-C and Table 2).

A) 84.80 and 10.89433

This zirconium silicate decontaminated arsenic up to 54.5%, when 1.0 gram of this material was treated by mixing with 1 liter of 2.5 ppm arsenic solution prepared from Sodium arsenate (Table 2).

This zirconium silicate disinfected 98% out of $2.72 \times 10^5$ coliform bacteria from drinking water, when 250 mg of zirconium silicate was added to 1 liter of coliform contaminated drinking water (Table 2).

Now the present invention will be described in detail based on the experiments conducted with immobilized functional transition metal silicates.

15) Arsenic Decontamination of Immobilized Functional Transition Metal Silicates on Activated Alumina (Size: Above 1000 microns):

250 ml of Sodium arsenate solution (containing 2.12 ppm of arsenic) was passed through 10×1 cm column at a flow rate of 10 ml/min. The arsenic content present in treated solution was measured by using ICP-AES and or AAS.

As evidenced from Table 8 the immobilized functional transition metal silicates absorbed arsenic significantly.

Cupric silicate immobilized on activated alumina, decontaminated arsenic content 90.10%. Zinc silicate immobilized on activated alumina decontaminated arsenic content 91.98%. Manganese silicate immobilized on activated alumina decontaminated arsenic content 58.96%. Zirconium silicate immobilized on activated alumina decontaminated arsenic content 13.08%.

16) Arsenic Decontamination of Immobilized Functional Transition Metal Silicates on Different Sizes on Activated Alumina:

1000 ml of Sodium arsenate solution (containing 2.4 ppm of arsenic) was passed through 10×1 cm column at a flow rate of 10 ml/min. Different sizes of immobilized functional transition metal silicates on activated alumina granules (500 microns and 1000 microns size,) were tested. The arsenic content present in treated solution was measured by using ICP-AES and or AAS.

Cupric silicate, immobilized on activated alumina (500 microns) decontaminated arsenic up to 95.58% compared to 86.05% decontamination resulted in treatment with cupric silicate, immobilized on activated alumina of 1000 microns size (Table-10).

17) Arsenic Decontamination Property of Immobilized Functional Transition Metal Silicates on Agropolymers:

250 ml of sodium arsenate solution (containing 500 ppb of arsenic) was passed through 250 mg of cupric silicate immobilized on agropolymer containing column at a flow rate of 1 ml/min. The arsenic content present in treated solution was measured by using ICP-AES and or AAS.

As evidenced from Table 11 the immobilized functional transition metal silicates on agropolymers absorbed arsenic significantly.

Cupric silicate immobilized on agropolymer decontaminated 56.48% of arsenic content.

18) Decontamination Property of Functional Transition Metal Silicates by Physical Immobilization on Quartz Sand (250-500 microns Size):

Immobilized functional transition metal silicates were prepared by adding transition metal salt containing solution to quartz sand (250-500 microns size), later reacting with sodium silicate to obtain immobilized functional transition metal silicate on quartz sand. Excess unbound non-immobilized substances were removed after through washing with distilled or deionized water. 250 ml of sodium arsenate solution (containing 2.12 ppm of arsenic) was passed through 10×1 cm containing column at a flow rate of 10 ml/min. The arsenic content present in treated solution was measured by using ICP-AES and or AAS.

As evidenced from Table 12 the immobilized functional transition metal silicates coated on quartz sand absorbed arsenic significantly.

Cupric silicate, zinc silicate, manganese silicate, and zirconium silicate decontaminated arsenic 35%, 48.58%, 18.87%, and 8.1% respectively, compared to 1.88% arsenic decontamination by quartz sand (control).

19) Mercury Decontamination Property of Immobilized Functional Transition Metal Silicates on Activated Alumina and Agropolymer:

Immobilized functional transition metal silicates on activated alumina and agropolymer were reacted separately with mercury containing solutions (224.21 ppb mercuric content) in a batch mode of a liter solution at a dose of 1 mg/ml. These materials were mixed well for 1 hour in mercury containing solutions and mercuric content (ppb) after treatment was measured by using AAS (hydria attached to graphite furnace).

Immobilized functional transition metal silicates sequestered mercury from the solution to below detection limits (as shown in Table 13).

20) Protein Decontamination Property of Immobilized Functional Transition Metal Silicates:

100 ml of BSA solution (1 mg/ml BSA content), was passed through 2×1 cm column of immobilized functional transition metal silicates on agropolymer and the protein bound to the immobilized functional transition metal silicate was assayed by estimating protein content in treated solutions by Lowry method.

As indicated in Table 14 the immobilized functional transition metal silicates decontaminated proteins.

Silver silicate immobilized on agropolymer-absorbed 10 mg of BSA protein compared to 15.4 mg and 3 mg absorption by cupric silicate immobilized on agropolymer and zinc silicate immobilized on agropolymer respectively. Total reaction volume is 100 ml containing 100 mg BSA protein.

21) Pesticides Decontamination Nature of Functional Transition Metal Silicates Immobilized on Agropolymers:

A solution containing 10 ppm each of *Endosulphan*, *Cypermethrin* and *Chlorpyriphos* was passed through a column containing 1 gm of immobilized cupric silicate (on activated alumina and agropolymer) at a rate of 0.5 ml/min. Pesticide content in treated solution was estimated by G.C.-ECD/p FPD.

As shown in Table 15 cupric silicates immobilized on activated alumina and agropolymer decontaminated of pesticides such as *Endosulphan*, *Cypermethrin*, and *Chlorpyriphos*.

Cupric silicate immobilized on activated alumina decontaminated 59.7% *Endosulphan*, 62.4% *Cypermethrin* and 46.6% *Chlorpyriphos* respectively.

Cupric silicate immobilized on agropolymer decontaminated 61.7% *Endosulphan*, 83.4% *Cypermethrin* and 49.1% *Chlorpyriphos* respectively.

22) Bacterial (Coliform) Decontamination of Immobilized Functional Transition Metal Silicates on Activated Alumina:

Bacterial coliform ($5 \times 10^5$) containing 500 ml of water was passed through 10 cm length immobilized functional transition metal silicate on activated alumina column at a flow rate of 10 ml/min.

The decontamination was assayed by measuring bacterial colonies in a petriplate containing bacterial growth medium.

As evidenced from Table 16 the immobilized functional transition metal silicates decontaminated coliform significantly. Silver silicate, cupric silicate decontaminated coliform content up to 98%, and 83% respectively. Zinc silicate immobilized on activated alumina decontaminated coliform content up to 43%.

23) Bacterial Decontamination of Immobilized Functional Transition Metal Silicates on Agropolymers:

Bacterial coliform containing water was passed through 250 mg containing (functional transition metal silicates immobilized on agropolymer) column at a flow rate of 10 ml/min, and bacterial colonies in treated solution was assayed in a petriplate containing bacterial growth medium.

The results as shown in Table 17 indicates that immobilized functional transition metal silicates decontaminated coliform bacteria from water.

Cupric silicate immobilized on agropolymer decontaminated coliform bacteria (coliform concentration of treated water=$4 \times 10^4$/liter) 99%, 97.45% and 94.87% from 2000 ml, 2500 ml and 3000 ml of coliform containing water respectively. Whereas silver silicate immobilized on agropolymer decontaminated coliform up to 99% from 3000 ml coliform containing water. Zinc silicate immobilized on agropolymer decontaminated 61.90%, 14.28% and 4.76% coliform content from 1000 ml, 1500 ml and 2000 ml coliform contaminated water.

24) Bacterial Decontamination Property of Immobilized Functional Transition Metal Silicates on Aluminium Oxides, Cellulose:

Bacterial coliform containing water was passed through immobilized functional transition metal silicates on column mode. The immobilized functional transition metal silicates on aluminium oxide, cellulose were tested for their bacterial decontamination property. The coliform containing water (460 colonies/ml) was passed through their immobilized functional transition metal silicates columns at a flow rate of 5 ml/min.

The decontamination was assayed by measuring bacterial colonies in a petriplate containing bacterial growth medium.

The results as shown in Table 18 indicates that immobilized functional transition metal silicates decontaminated coliform bacteria from water.

Cupric silicate immobilized on aluminium oxide (1 gm filled in a column) decontaminated coliform up to 93.47% from 250 ml of coliform ($1.15 \times 10^5$) containing water cupric silicate immobilized on cellulose (0.97 gm filled in a column) decontaminated coliform up to 93.71% from 250 ml of coliform ($1.38 \times 10^5$) containing water.

25) Bacterial Decontamination Property of Immobilized Functional Transition Metal Silicates Coated on Quartz Sand:

Coliform containing 500 ml water was passed through 10×1 cm column of functional transition metal silicates coated on quartz sand at a flow rate of 10 ml/min.

The decontamination was assayed by measuring bacterial colonies in a petriplate containing bacterial growth medium.

Functional transition metal silicates immobilized on quartz sand decontaminated coliform bacteria. Cupric silicate immobilized on quartz sand decontaminated 83% compared to 34% decontamination by zinc silicate immobilized on quartz sand. Manganese silicate immobilized on quartz sand and zirconium silicate immobilized on quartz sand decontaminated coliform up to 5% and 6% respectively (Table 19).

26) Decontamination of Fungus (*Aspergillus* Species) from a Long Time (6 Months) Stored Water by Using Immobilized Functional Transition Metal Silicates:

Commercial available packaged drinking water was stored for 6 months, by allowing for development of microbial contaminants like fungus. After observing the contamination of fungus in the stored water present study was conducted to determine the fungal decontamination property of immobilized functional transition metal silicates. One liter of fungal contaminated water was passed through 2×1 cms. column of cupric silicate immobilized on agropolymer at a flow rate of 10 ml/min. Fungal presence was screened by placing the treated and untreated solutions on petriplates containing fungal growth medium.

Cupric silicate immobilized on agropolymer decontaminated fungus (*Aspergillus* species) from stored drinking water (Table 20).

27) Protozoan (*Cryptosporidium parvum*) Decontamination Property of Immobilized Functional Transition Metal Silicates:

One gram of the cupric silicate immobilized on agropolymers was aseptically weighed and placed into 10×1-cm glass columns. The bottom of the column contained glass wool to prevent the material from flowing through the column. The columns were gently tapped before and after wetting to assure uniform packing of the material. Three liters of deionized water was passed through the columns using a master flex L/S computerized drive pump (Cole-Palrer Instrument Co., Barrington, Ill., USA) at a flow rate of 15 ml/min to assure rinsing of the material. One milliliter of the *cryptosporidium parvum* stock ($2 \times 10^7$) was added to 200 ml of sterile deionized water (DI, pH 0.8-8.4). The seeded deionized water was then passed through the column using the above pump at a flow rate of 5 ml/min fractions of the column influent and effluent were collected after the passage of 20, 50 and 80 ml of seeded deionized water. The oocysts in the samples were enumerated by Immuno Florescent Assay (IFA). Briefly, the samples were filtered through a Sartorius cellulose acetate membrane filter and stained with FITC-labeled anti-*Cryptosporidium* monoclonal antibody (Crypt-o-Glow, waterborne, Inc New Orleans, La.). Filters were then dehydrated with and ethanol series (20, 40, 80, 90%) and viewed by epifluorescence microscopy. The oocysts were counted and the titer for each sample was calculated (Table 21).

Cupric silicate immobilized on agropolymer decontaminated *Cryptosporidium parvum* significantly (Table 21).
    a. Viral decontamination property of immobilized functional transition metal silicates.
    b. *E. coli* o157:h7 (atcc 110195-b1) decontamination property of immobilized functional transition metal silicates.

The following procedure was followed to assay the viral decontamination and bacterial decontamination property.

Viral Stock Preparation:

Polio Lsc 1 viral stock preparation was performed according to the methods of Berg Et al., (1984). Tissue culture flasks (T-182) were seeded with trypsiniazed Buffalo Green Monkey (BGM) cells and Minimum Essential Media (MEM, Cellgro®, Mediatech Inc., Cat#10010179) containing earl's salts, L-glutamine, 100 u Penicillin G, 100 u Streptomycin, 0.25 µg/ml Amphotericin B, 100 mm HEPES, and 10% Fetal Bovine Serum (FBS). The flasks were incubated in a 36° C. incubator for 48 hours to allow the development of the continuous monolayer of cells. The flasks were then prepared for viral inoculation by rinsing the monolayer twice with Phosphate Buffered Saline (PBS) Aliquots of the Poliovirus Lsc 1 (ATCC VR-59) viral stocks were inoculated into the T-182 flasks containing continuous monolayer. The viral aliquots were allowed to incubate into the cell monolayer for 40 min. Following incubation; 35 ml of MEM containing earl's salts L-glutamine, 100 u penicillin G, 100 u Sterptomysin, 0.25 µg/ml Amphotericin B, and 100 mm HEPES was added to each of the flasks. The flasks were incubated at 36° C. for 36 hours. At this time >90+ of the monolayer exhibited significant Cyptopathic Effects (CPE). The flasks were then freeze-thawed (2×), and centrifuge at 10,000 g for 20 min. The supernatant was then collected; aliquoted, titrated, and stored at 70° C. till use.

Rotavirus preparation was conducted according to the procedure described by Smith and Gerba, (1982). Briefly, tissue culture flasks (T-182) were seeded with trypsiniazed MA-104 (ATCC Crl-2378) cells and Minimum Essential Media (MEM, Cellgro, Mediatech Inc., Cat #10010179) containing earl's salts, L-glutamine, 100 u Penicillin G, 100 u Streptomycin, 0.25 µg/ml Amphotericin B, 100 mm, HEPES, and 10% Fetal Bovine Serum (FBS). The flasks were incubated in a 36° C. incubator for 48 hours to allow the development of the continuous monolayer of cells. The flasks were then prepared for viral inoculation by rinsing the monolayer twice with Phosphate Buffered Saline (PBS). Aliquots of the Rotavirus SA 11 (ATCC VR-899) viral stocks were inoculated into the T-182 flasks containing continuous monolayer. The viral aliquots were allowed to incubate onto the cell monolayer for 40 min. Following incubation, 35 ml of MEM containing earl's salts, L-glutamine, 100 u Penicillin G, 100 u Streptomycin, 0.25 µg/ml. Amphotericin B, 5 mg/l Trypsin, and 100 mm HEPES was added to each of the flasks. The flasks were incubated at 36° C. for 6-8 days. At this time >90+ of the monolayer exhibited significant Cytopathic Effects (CPE). The flasks were then freeze-thawed (2×), and centrifuged at 10,000 g for 20 min. The supernatant was then collected, aliquoted, titrated, and stored at 70° C. till use.

Viral Enumeration:

Poliovirus 1 (Lsc1) was grown and assayed as pfu on Buffalo Green Monkey Kidney (BGM) cells by an agar overlay methos (Berg et al., 1984). Briefly, the samples were received frozen and thawed slowly to 4° C. Aliquots were inoculated onto recently passed (2-3 days) continuous monolayers of BGM cells. Monolayers in T-25 flasks received 1.0 ml inoculum, T-75 received 3.0 ml and T-182 received 6.0 ml. The influent samples were diluted ten fold in sterile PBS and 1.0 ml aliquots of the dilutions were inoculated onto monolayers in T-25 flasks. The samples were allowed to incubate for 40 min on the monolayers. 2× eMEM containing 8% FBS and 0.1% Neutral Red was mixed with equal volume of sterile molten 2.2% Bacto Agar (Becton Dickinson, Sparks Md.). The media was then added to each of the inoculated flasks, and the agar was allowed to solidify onto the monolayers. The flasks were then incubated at 36° C. for 2-5 days to allow plaque development and enumeration. The results of this assay are reported in Table-20.

Rotavirus SA 11 was assayed as most probable number on MA-104 cells. Briefly, aliquots of the received samples were inoculated onto recently passed (2-3 days) continuous monolayers of MA-104 cells. Prior to inoculation the monolayers in the flasks were rinsed twice with sterilse PBS. Monolayers in T-25 flasks received 1.0 ml inoculum, T-75 received 3.0 ml, and T-182 received 6.0 ml. The influent samples were monolayers diluted ten fold in sterile PBS and 1.0 ml aliquots of the dilutions were inoculated onto monolayers in T-25 flasks. All inoculums were adjusted to 5 mg/ltr trypsin and they were allowed to incubate onto the monolayer for 40 min. Following incubation, eMEM, L-glutamine, 100 u Penicillin G, 100 u Streptomycin, 0.25 μg/ml. Amphotercin B, 5 mg/ltr Trypsin, and 100 mm HEPES was added to each of the inoculated flasks. The flasks were then incubated at 36° C. for 7-10, 2-5 days to allow CPE development. The results of the assay are reported in Table-20.

Bacterial Cultures and Enumeration:

*E. Coli* O157: H7 (ATCC 110195-B1) was sub-cultured on tryptic soy agfar (Dicco Laboratories, Detroit, Mich.). For all experiments, inocula were prepared from cultures grown at 37° C. in tryptic soy both (TSB; Difco) for 18 to 24 hrs. Bacteria were enumerated by spread plating on tryptic soy agar (TSA) and incubating for 18-24 hours at 37° C.

Column Adsorption Studies:

Immobilized cupric silicate on agropolymer and immobilized cupric silicate on activated alumina (500 micron size) were aspectically weighed and placed into 10×1 cm glass columns. The bottom of the column contained glass wool to prevent the material from flowing through the column. The columns were gently tapped before and after wetting to assure uniform packing of the material. Three liters of DI was passed through the columns using Mate flex L/S computerized drive pump (Cole-Palrer Instrument Co., Barrington. Ill. USA) at a flow rate of 15 ml/min to assure rinsing of the material. Aliquots of the Rotavirus viral stock were added to 250 ml of sterile deionized water (DI, pH 7.8-8.4) to achieve final concentration of approximately $10^6$-pfu/ml. The seeded deionized water was then passed through the column using the above pump at a flow rate of 5 ml/min. Fractions of the column influent and effluent were collected after the passage of 50, 100, and 200 ml of seeded DI Following, aliquots of the Polio 1 viral stock and *E. Coli* O157:H7 overnight culture were added to another 250 ml of sterile deionized water (DI, pH7.8-8.4) to achieve final concentration of approximately $10^6$-pfu/ml. The seeded DI was then passed through the column using the above pump at a flow rate of 5 ml/min. Fractions of the column influent and effluent were also collected after the passage of 50, 100, 200 ml of seeded DI. The sample were serially diluted and assayed for the respective virus and bacteria as described above. The results are indicated in Table-20.

REFERENCES

Smith, E. M. and C. P. Gerba, 1982. Laboratory methods for the growth and detection of animal viruses. In C. P. Gerba and S. M. Goyal, ed. Methods in Environmental Virology. Marcel Dekker, Inc. New York, N.Y. P. 76-88.

Berg, G., R. S. Safferman, D. R. Dahling, D. Berman, and C. J. Hurst, 1984 USEPA Manual of Methods for Virology, U.S. EPA, Cincinnati, Ohio.

Cuprous silicate immobilized on agropolymer and cupric silicate immobilized on activated alumina decontaminated Polio Lsc 1 and Rotavirus SA11 (as shown in Table 22).

Cupric silicate immobilized on agropolymer decontaminated polio Lsc1 viruses up to 55.9% when 1 gram of material was used in a column compared to 99.9% of decontamination resulted by using of 2 grams of material in a column.

Cupric silicate immobilized on agropolymer decontaminated rota viruses SA11 viruses up to 48.8% when 1 gram of material was used in a column compared to 99.9% of decontamination resulted by using of 2 grams of material in a column.

Cupric silicate immobilized on activated alumina decontaminated polio Lsc1 viruses up to 70.3% when 10 gram of material was used in a column compared to 99.3% of decontamination resulted by using of 20 grams of material in a column.

Cupric silicate immobilized on activated alumina decontaminated rota viruses SA11 up to 86.2% when 10 gram of material was used in a column compared to 99.8% of decontamination resulted by using of 20 grams of material in a column.

The cupric silicate immobilized on agropolymer and also cupric silicate activated alumina decontaminated *E. coli* O157:H7 bacteria.

28) Chemical Decontamination Property of Immobilized Functional Transition Metal Silicates on Silica Gel:

Functional transition metal silicates were immobilized on silica gel. Chemical contaminants such as trihalomethanes, polychlorinated biphenyls, semi volatile organic compounds, volatile organic compounds, and phenols were dissolved separately in water and passed through a column of functional transition metal silicate immobilized on silica gel (6×1 cm column at 0.5-1 ml/minute flow rate). The chemical pollutant content in treated solution was assayed by using GC-FID or GC-ECD or GC/MS/MS.

Cupric silicate immobilized on silica gel decontaminated 7.5 ppm of trihalomethanes (such as chloroform, 1,1,1, trichloroethane, tetrachloroethylene, trichloroethylene, bromodichloroethane, dibromochloroethane, tetrachloroethylene, bromoform, 1,2, dichloro-3-bromopropane) out of 8.950 ppm of trihalomethanes as shown in Table-23.

Cupric silicate immobilized on silica gel decontaminated 2.4 ppm of Polychlorinatedbiphenyls (such as 2,3-dichlorobiphenyl, trichlorobiphenyl, tetrachlorobiphenyl, pentachlorobiphenyl, hexachlorobiphenyl, heptachlorobiphenyl, octachlorobiphenyl) out of 3.5729 ppm of Polychlorinated-biphenyls as shown in Table-27.

Cupric silicate immobilized on silica gel decontaminated 9.1 ppm of semi volatile organic compounds (such as Benzene, 1,4-dichloro; ethane hexachloro; benzene 1,2,3, trichloro; 1,3 butadiene, 1,1,2,3,4; naphthalene, 2-chloro; acenephthylene; acenapthene; phenol, 2,4-bis(1,1-imet); diethyl phthalate; fluorene; benzene1-chloro-3-phenol; diphenylamine; 4-bromophenyl-phenylether; benzene, hexachloro; phenantherene; anthracene; dibutyl phthalate; fluoranthene; pyrene; benzyl butyl phthalate; chrysene; bis (2-ethylhexy)phthalate; phenol, 2,3,4,5-tetrabrom; di-n-octyl phthalate; benzo(b)fluoranthene; benzo(k)fluoranthene; benzo(a)pyrene; indeno(1,2,3-cd)pyrene, dibenzo(a,h)anthracene; benzo(g,h,l)perylene) out of 20.8196 ppm of semi volatile organic compounds as shown in Table 24.

Cupric silicate immobilized on silica gel decontaminated 10.8 ppm, of volatile organic compounds (such as 1,1,1, trichloroethane; 1,1,2-trichloroethane; 1,3-dichloropropane; dibromochloromethane; ethane 1,2 dibromo; chlorobenzene; benzene 1,2-dimethyl; benzene 1,3-dimethyl; orthoxylene; benzene 1-methylethyl; ethane 1,1,2,2-tetrachloro; bromobenzene; 2-chloro toluene; benzene, propyl; benzene, 1 chloro 4-methyl; benzene 1,2,3-trimethyl; 4-iso propyl toluene; benzene 1,2-diethyl; benzene 1,2-dichloro; 1,3-dichlorobenzene; 1,4-dichlorobenzene; toluene; n-butylbenzene; 1,2-dibromo 3-chloropropane; 1,2,4-trichlorobenzene; naphthalene; benzene 1,2,3-trichloro; benzene 1,3,5-trichloro; benzene 1,3,4-trichloro; 1,3-butadiene1,1,2,3,4; benzene 2-bromo 1,3,5; nitrobenzene; styrene; benzylbenzoate; 1,2,3, 4-tetramethylbenzene; benzene 1-chloro 2-propyl; 4-bromo 3-chloroanilene) out of 18.5 ppm of volatile organic compounds as shown in Table 25.

Cupric silicate immobilized on silica gel decontaminated 2.8 ppm of phenols (such as benzoic acid; 2,4,5-trichlorophenol; 3-nitroaniline; 3-nitrophenol; 4-nitrophenol; 2,4-dinitrophenol; 4-nitroaniline; pentachlorophenol) out of 7.5234 ppm of phenols as shown in Table 26.

Zinc silicate immobilized on silica gel decontaminated 6.8 ppm of trihalomethanes (such as chloroform, 1,1,1, trichloroethane, tetrachloroethylene, trichloroethylene, bromodichloroethane, dibromochloroethane, tetrachloroethylene, bromoform, 1,2, dichlor-3-bromopropane) out of 9.1725 ppm of trihalomethanes as shown in Table 28.

Silver silicate immobilized on silica gel decontaminated 7.2 ppm of trihalomethanes (such as chloroform, 1,1,1, trichloroethane, tetrachloroethylene, trichloroethylene, bromodichloroethane, dibromochloroethane, tetrachloroethylene, bromoform, 1,2, dichlor-3-bromopropane) out of 9.1725 ppm of trihalomethanes as shown in Table 29.

Manganese silicate immobilized on silica gel decontaminated 7.5 ppm of trihalomethanes (such as chloroform, 1,1,1, trichloroethane, tetrachloroethylene, trichloroethylene, bromodichloroethane, dibromochloroethane, tetrachloroethylene, bromoform, 1,2, dichlor-3-bromopropane) out of 9.1725 ppm of trihalomethanes as shown in Table 30.

Zirconium silicate immobilized on silica gel decontaminated 5.1 ppm of trihalomethanes (such as chloroform, 1,1,1, trichloroethane, tetrachloroethylene, trichloroethylene, bromodichloroethane, dibromochloroethane, tetrachloroethylene, bromoform, 1,2, dichlor-3-bromopropane) out of 9.1725 ppm of trihalomethanes as shown in Table 31.

29) Bacterial Decontamination Property of Immobilized Functional Transition Metal Silicates Obtained by Incorporation of Functional Transition Metal Silicates into Resins (Such as Vinyl Ester, Bisphenol and Isopthalic Resins):

Bacterial coliform containing water was passed through immobilized functional transition metal silicates on column mode. The immobilized functional transition metal silicates containing resins were tested for their bacterial decontamination property. The coliform containing water (460 col/ml) was passed through 3.6 grams of immobilized functional transition metal silicates filled in a column, at a flow rate of 5 ml/min.

The decontamination was assayed by measuring bacterial colonies in a petriplate containing bacterial growth medium.

The results as shown in Table 32 indicates that immobilized functional transition metal silicates decontaminated coliform bacteria from water.

Cupric silicate immobilized on bisphenol resins (3.6 gms) decontaminated coliform up to 70% from 200 ml of ($1.38 \times 10^5$) coliform containing water.

30) Bacterial Decontamination Property of Functional Transition Metal Silicate Resin Coatings on Sand:

1 gm of cupric silicate mixed with 10 ml of isopthalic resin was coated on 100 ml volume of quartz sand (500 microns) and the coliform bacteria $3.23 \times 10^5$/liter containing water passed through the 5×1 cm size materials in column.

Functional transition metal silicate containing resin coated quartz sand decontaminated coliform bacteria up to 28.79 and 20.12% from 500 ml and 1000 ml from $3.23 \times 10^5$/liter coliform containing bacteria (Table 33).

31. Toxic Gases Detoxification Nature of Immobilized Functional Transition Metal Silicates:

To determine the toxic gases detoxification nature of immobilized functional transition metal silicates, the smoke emissions from combustion of kerosene engine, was passed through the immobilized functional transition metal silicates packed in 20×3 cm column.

Uniform combustion of kerosene was maintained along with controls. The toxic gases such as carbon monoxide, sulphur dioxide, and $NO_X$ (oxides of nitrogen) were assayed using flew gas analyzer (testo-350) equipment. The immobilized functional transition metal silicates detoxified toxic gases from kerosene combustion (shown in Table 34).

Immobilized functional transition metal silicates also reduced the hydrocarbons released from the combustion.

32. Nicotine and Tar Detoxification Nature of Immobilized Functional Transition Metal Silicates A mini smoking machine was fabricated to pass the cigarette smoke through immobilized functional transition metal silicate (500 mg) containing filter (a mini column packed in a 1 ml pipette plastic tip). The uniform burning of the cigarette with uniform sucking of the smoke was done by controlling suction by a vacuum pump attached to a glass chamber connected to smoking outlet of cigarette.

After passing cigarette smoke the functional transition metal silicate-containing filter was extracted with acetone.

Total content of nicotine absorbed in these filters was estimated at UV 254 nm using standard nicotine solutions (95%, standard nicotine solution, BDH, England). Total tar content was estimated by evaporating the acetone extraction of filter in a crucible. Toxic gases were estimated from the glass chamber and for comparison cigarette smoke obtained without any filter was taken as control. As shown in Table (35) immobilized functional transition metal silicates reduced tar and nicotine significantly.

The toxic gases such as carbon monoxide, sulphur dioxide, $NO_X$ (oxides of nitrogen) and hydrocarbons were assayed using flew gas analyzer (testo-350) equipment and the immobilized functional transition metal silicates containing filters detoxified toxic gases from cigarette smoke (Table 36).

This invention now will describe the salient features of functional transition metal silicates. Functional transition metal silicates having varied silicate metal ratio were synthesized and silicate or metal content enhancement or decrease in a functional transition metal silicates was done at suitable reaction conditions (at acidic or neutral or basic or extreme acidic pH conditions) and using varied reactants such as soluble silica having different alkali silica ratios.

Functional transition metal silicates synthesized at acidic pH conditions possess effective functions (decontamination of metals, chemicals, disinfection of microbes, fungicidal and bactericidal activities) than functional transition metal silicates synthesized at neutral or basic conditions.

Functional transition metal silicates synthesized at extreme acidic pH conditions by addition of acid (such as HCl or $HNO_3$) containing very low transition metal content also possesses functional activities such as decontamination and disinfection etc. Contrary functional transition metal silicates prepared in basic conditions with low transition metal content failed to exert effective disinfection or decontamination properties. This may be due to many reasons and one important reason is that the formation of more amount transition metal hydroxides along with silicates structure at alkaline conditions. As evidence in Tables 1 & 5, cupric silicate prepared at basic conditions even at higher doses failed to decontaminate arsenic or disinfect bacteria effectively. The transition metal silicate ratios although similar, some are functional and the others are non-functional. This variability of functionality of transition metal silicates is the topic of this invention.

Each functional transition metal silicate has its own uniqueness. Cupric silicates exhibited very strong decontamination and disinfection properties. Zinc has more freedom or capacity to interact with silica and functional zinc silicates structuring were done based on decontamination and disinfection nature. Similarly manganese silicates, silver silicates, and zirconium silicates functionality was enhanced by optimizing conditions of synthesis.

Regarding silver silicates when they were synthesized at basic or neutral pH conditions failed to absorb arsenic like toxic metals and silver silicates synthesized at extreme acidic pH conditions (by addition of nitric acid) absorbed arsenic effectively. Zirconium silicates synthesized at neutral or basic pH conditions, do not possess bacterial decontamination nature and synthesizing at acidic pH conditions zirconium silicates attained the desired bacterial decontamination property. The particle size was uniformly maintained (below 1 µm and above 0.5 µm) for testing these functional transition metal silicates.

These immobilizations in present invention can be classified as physical or chemical or incorporating directly into the resins. The selected materials for chemical immobilization (such as agropolymers, activated alumina, silica gel) has the property to bind with transition metals. Activated alumina, as it is amphoteric, passes the electron to charged copper.

Physical immobilization of functional transition metal silicates was done on cellulose, quartz sand, and by incorporating into resins. Transition metal silicate containing resins were coated on quartz sand.

The wide application of the said functional transition metal silicates is an important aspect of the invention. Accordingly the invention pertains to a method of producing immobilized transition metal silicates using activated alumina, aluminum oxide, cellulose, resins, quartz sand, and functional transition metal silicate containing resin coated quartz sand.

Now it is essential to summarize the findings of the investigations carried by the applicant in the following Tables 1 to 36.

Table 1 denotes the comparative functional and structural variability of functional transition metal silicate (cupric silicate) based on variable parameters of synthesis.

Table 2 denotes the comparative functional and structural variability of functional transition metal silicates (silver silicate, manganese silicate, zinc silicate and zirconium silicate) based on variable parameters of synthesis.

Table 3 denotes the bactericidal property of cupric silicates against *Staphylococcus aureus, Bacillus subtilis, Pseudomonas aeruginosa*, and *E. coli*.

Table 4 denotes the comparative bactericidal property of cupric silicates. Cupric silicate (silicate:transition metal ratio=1:5.15) and cupric silicate (silicate:transition metal ratio=1:1) at a concentration of 0.06 and 0.0125 were tested for comparative bactericidal property against *E. coli*.

Table 5 denotes the bactericidal property of zinc silicate at a concentration of 0.25% mixed in bacterial growth media, which was tested against Staphylococcus aureus.

Table 6 denotes the comparative fungicidal property of cupric silicates against *Scelerotium rolfsii, Rhizoctonia solani, Fusarium oxysporium*, and *Pyricularia oryzae*.

Table 7 denotes the viral disinfection property functional transition metal silicate (Cupric silicate).

Table 8 denotes the trihalomethanes decontamination property of cupric silicate.

Table 9 denotes the arsenic decontamination of immobilized functional transition metal silicates on activated alumina (size: above 1000 microns).

Table 10 denotes the arsenic decontamination of immobilized functional transition metal silicates on different sizes on activated alumina.

Table 11 denotes the arsenic decontamination of immobilized functional transition metal silicates on agropolymers.

Table 12 denotes the decontamination property of transition metal substances by physical immobilization on quartz sand (250-500 microns size).

Table 13 denotes the mercury decontamination property of immobilized functional transition metal silicates on activated alumina and agropolymer.

Table 14 denotes the protein decontamination property of functional transition metal silicate immobilized on agropolymers.

Table 15 denotes the pesticidal decontamination nature of functional transition metal silicate immobilized on agropolymers.

Table 16 denotes the bacterial (coliform) decontamination of immobilized functional transition metal silicates on activated alumina.

Table 17 denotes the bacterial decontamination of immobilized functional transition metal silicates on agropolymers.

Table 18 denotes the bacterial decontamination property of immobilized functional transition metal silicates on aluminium oxides, and cellulose.

Table 19 denotes the bacterial decontamination property of immobilized functional transition metal silicates on quartz sand.

Table 20 denotes the decontamination of fungus (*Aspergillus* species) from a long time (6 months) stored water by using immobilized functional transition metal silicates.

Table 21 denotes the protozoan (*Cryptosporidium parvum*) decontamination property of immobilized functional transition metal silicates on agropolymer.

Table 22 denotes the viral decontamination property of immobilized functional transition metal silicates and *E. coli* decontamination nature of immobilized functional transition metal silicates.

Table 23 denotes the trihalomethanes decontamination property of cupric silicate immobilized on silica gel.

Table 24 denotes the semi volatile organic compounds decontamination property of cupric silicate immobilized on silica gel.

Table 25 denotes the volatile organic compounds decontamination property of cupric silicate immobilized on silica gel.

Table 26 denotes the phenols decontamination property of cupric silicate immobilized on silica gel.

Table 27 denotes the polychlorinated biphenyls decontamination property of cupric silicate immobilized on silica gel.

Table 28 denotes the trihalomethanes decontamination property of zinc silicate immobilized on silica gel.

Table 29 denotes the trihalomethanes decontamination property of silver silicate immobilized on silica gel.

Table 30 denotes the trihalomethanes decontamination property of manganese silicate immobilized on silica gel.

Table 31 denotes the trihalomethanes decontamination property of zirconium silicate immobilized on silica gel.

Table 32 denotes the bacterial decontamination property of immobilized functional transition metal silicates (5%) incorporated in to resins.

Table 33 denotes the bacterial decontamination property of functional transition metal silicate resin coatings on sand.

Table 34 denotes the toxic gas (engine combustion) detoxification (%) nature of immobilized functional transition metal silicates.

Table 35 denotes the tar and nicotine absorption property of immobilized functional transition metal silicates.

Table 36 denotes the cigarette smoke detoxification nature (%) of immobilized functional transition metal silicates.

The results derived from the present invention gives a scope of synthesizing functional transition metal silicates (such as cupric silicate, silver silicate, manganese silicate, zinc silicate) and functional transition metal silicates immobilized on materials such as activated alumina, aluminium oxide, agropolymers, cellulose, quartz sand, silica gel, resins (vinyl ester, bisphenol and isopthalic food grain resins), and functional transition metal silicates incorporated resins and functional transition metal silicate containing resin coated sand having varied metal silicate ratio exhibiting varied functions which are useful in various other applications such as manufacturing of catalysts, and hybridizing or doping with zeolites.

TABLE 1

COMPARISION OF FUNCTIONAL TRANSITION METAL SILICATES

| S. No | Name of the material | Parameters of synthesis | Silica:transition metal ratio | ESR G values |
|---|---|---|---|---|
| 1 | Cupric silicate | Acidic conditions with 10 ml of sodium silicate [1:2] + 100 ml of 0.5 gm/ml transition metal salt solution | 1:5.15 | A) 4.32481 B) 2.66205 C) 2.31749 D) 2.08807 E) 2.04673 |
| 2 | Cupric silicate | Acidic conditions at 70° C. to 90° C. with 50 ml sodium silicate [1:1] + 100 ml of 0.5 gm/ml transition metal salt solution | 1:0.78 | A) 2.23480 B) 2.06456. |
| 3 | Cupric silicate | Neutral conditions with sodium silicate [1:1] + 100 ml of 0.5 gm/ml transition metal salt solution | 1:1 | A) 3.10383 B) 2.36522 C) 2.0467 D) 1.21887 E) 0.96686 |
| 4 | Cupric silicate | Basic conditions with sodium silicate [1:1] + 100 ml 0.5 gm/ml transition metal salt solution | 1:0.8 | A) 3.71806 B) 3.23001 C) 2.61681. |
| 5 | Cupric silicate | Extreme Acidic conditons at 70° C. to 90° C. with addition of 10 ml of 36% HCl and sodium silicate [1:1] + 100 ml of 0.5 gm/ml transition metal salt solution. | 1:0.63 | A) 2.18421 B) 2.06874 C) 1.21231. |
| 6 | Cupric silicate | Extreme Acidic conditions at 60° C. to 70° C. with addition of 20 ml 36% HCl and sodium silicate [1:1] + 100 ml of 0.5 gm/ml transition metal salt solution. | 1:0.34 | A) 2.15561 B) 2.03614 |

| S. No | XRD Peak height, (counts/s) and Angle(° 2 theta) | Weight of the material for bacterial decontamination (mg/Lt) | % Bacterial decontamination from $2.72 \times 10^5$ | Weight of the material for arsenic decontamination (mg/100 ml) | % Arsenic decontamination from 2.5 ppm |
|---|---|---|---|---|---|
| 1 | 1) 2128.25 and 18.28197 2) 1583.74 and 32.29018 3) 1470.73 and 39.79307 | 10 | 99 | 50 | 69 |
| 2 | 1) 835.63 and 16.20057 2) 706.74 and 32.23910 3) 602.62 and 39.57159 | 10 | 99 | 50 | 55.8 |

TABLE 1-continued

COMPARISION OF FUNCTIONAL TRANSITION METAL SILICATES

| | | | | | |
|---|---|---|---|---|---|
| 3 | 1) 940.91 and 16.19577<br>2) 764.43 and 32.29278<br>3) 694.85 and 39.77809 | 10 | 99 | 50 | 277 |
| 4 | 1) 152.74 and 26.64983 | 250 | 21.69 | 60 | 6 |
| 5 | 1) 400.70 and 16.19872<br>2) 394.77 and 32.27956<br>3) 330.02 and 39.71761 | 10 | 99 | 50 | 42 |
| 6 | 1) 541.23 and 16.28305<br>2) 414.21 and 32.36589<br>3) 365.45 and 39.85131 | 10 | 99 | 50 | 27.7 |

TABLE 2

COMPARISION OF FUNCTIONAL TRANSITION METAL SILICATES

| S. No | Name of the material | Parameters of synthesis | Silica:transition metal ratio | ESR G values |
|---|---|---|---|---|
| 7 | Zinc silicate | Neutral conditions with sodium silicate [1:1] + 100 ml of 0.5 gm/ml transition metal salt solution | 1:12.13 | A) 5.49809<br>B) 4.55342<br>C) 2.54593<br>D) 2.10091<br>E) 2.05499 |
| 8 | Zinc silicate | Extreme acidic conditions at 70° C. to 90° C. with addition of 10 ml of 38% HCl and sodium silicate [1:1] + 100 ml of 0.5 gm/ml transition metal salt solution. | 1:2.46 | A) 4.38410<br>B) 4.01910<br>C) 2.53191<br>D) 1.87888<br>E) 2.01793 |
| 9 | Silver silicate | Neutral conditions with sodium silicate [1:2] + 100 ml of 0.5 gm/ml transition metal salt solution. | 1:19.57 | A) 4.36796<br>B) 2.37847<br>C) 3.95509<br>D) 2.04657 |
| 10 | Silver silicate | Extreme acidic reaction at 70° C. to 90° C. conditions with addition of 8 ml of 69-70% $HNO_3$ and sodium silicate [1:1] + 100 ml of 0.5 gm/ml metal salt solution | 1:1.04 | A) 4.37171<br>B) 4.04714<br>C) 1.98189 |
| 11 | Manganese silicate | Neutral conditions with sodium silicate [1:1] + 100 ml of 0.5 gm/ml transition metal salt solution. | 1:1.94 | A) 1.93412<br>B) 2.08855 |
| 12 | Manganese silicate | Extreme acidic conditions at 70° C. to 90° C. with addition of 10 ml of 38% HCl and sodium silicate[1:1] + 100 ml of 0.5 gm/ml transition metal salt solution. | 1:1.09 | A) 4.34836<br>B) 4.17458<br>C) 2.18228<br>D) 2.11243<br>E) 2.05491<br>F) 1.999661 |
| 13 | Zirconium silicate | Neutral conditions with sodium silicate [1:1] + 100 ml of 0.5 gm/ml transition metal salt solution | 1:2.90 | A) 4.42797<br>B) 4.18272<br>C) 2.24547<br>D) 2.30425<br>E) 2.1896<br>F) 1.23088 |
| 14 | Zirconium silicate | Extreme acidic conditions at 70° C. to 90° C. with addition of 10 ml of 35% HCl and sodium silicate [1:1] + 100 ml of 0.5 gm/ml transition metal salt solution. | 1:0.77 | A) 4.37236<br>B) 2.82039<br>C) 1.92596<br>D) 1.21852<br>E) 1.02930<br>F) 0.93795 |

TABLE 2-continued

COMPARISION OF FUNCTIONAL TRANSITION METAL SILICATES

| S. No | XRD Peak height, (counts/s) and Angle(° 2 theta) | Weight of the material for bacterial decontamination (mg/Lt) | % Bacterial decontamination from $2.72 \times 10^5$ | Weight of the material for arsenic decontamination (mg/100 ml) | % Arsenic decontamination from 2.5 ppm |
|---|---|---|---|---|---|
| 7 | 1) 444.15 and 32.75904<br>2) 307.02 and 59.58455<br>3) 283.38 and 28.27638 | 250 | 96.58 | 100 | 98.7 |
| 8 | 1) 2078.88 and 11.07467<br>2) 835.44 and 33.52527<br>3) 664.98 and 32.88120 | 250 | 99.76 | 100 | 72.3 |
| 9 | 1) 3945.11 and 32.29885<br>2) 2421.27 and 48.27448<br>3) 1835.68 and 27.89129 | 5 | 99.5 | 100 | 4.5 |
| 10 | 1) 2217.87 and 29.33483<br>2) 684.55 and 47.68093<br>3) 674.27 and 42.31091 | 5 | 99.5 | 100 | 99 |
| 11 | 1) 148.04 and 30.65087 | 500 | 51.68 | 100 | 12.4 |
| 12 | 1) 32.88 and 24.65599 | 500 | 58.8 | 100 | 10.3 |
| 13 | — | 250 | 2.0 | 100 | 28.9 |
| 14 | 1) 84.80 and 10.89433 | 250 | 98.8 | 100 | 54.5 |

TABLE 3

Bactericidal property of cupric silicates:

| Material embedded in LB agar media | Material concentration | Silica:transition metal ratio | Test bacteria | Result |
|---|---|---|---|---|
| Cupric silicate | 0.25% | 1:5.15 | Staphylococus aureus | No growth was observed |
| Cupric silicate | 0.25% | 1:5.15 | Pseudomonas aeruginosa | No growth was observed |
| Cupric silicate | 0.25% | 1:5.15 | Bacillus subtilis | No growth was observed |
| Cupric silicate | 0.25% | 1:5.15 | Eschericia coli | No growth was observed |
| Control | | | | Significant growth was observed |

TABLE 4

Comparative bactericidal property of cupric silicates:

| Name of the sample | Silica:transition metal ratio | Name of the pathogen | Material Concentration 0.06% | 0.125% |
|---|---|---|---|---|
| Cupric silicate Synthesized at acidic reaction conditions | 1:5.15 | Escherichia coli | Significant growth was observed | No growth was observed |
| Cupric silicate synthesized at neutral reaction conditions | 1:1 | Escherichia coli | Significant growth was observed | Significant growth was observed |
| Control | | Escherichia Coli | Significant growth was Observed | |

TABLE 5

Bactericidal property of Zinc silicate

| Material embedded in LB agar media | Material concentration | Silica:transition metal ratio | Test Bacteria | Results |
|---|---|---|---|---|
| Zinc silicate | 0.25% | 1:12 | Staphylococus aureus | No growth was observed |
| Control | | | | Significant growth was observed |

TABLE 6

Comparative fungicidal property of cupric silicates:

| Name of the sample | Silica:transition metal ratios | Name of the pathogen | Percent reduction in colony diameter over control | | |
|---|---|---|---|---|---|
| | | | 0.0625% | 0.125% | 0.25% |
| Cupric silicate synthesized at acidic pH reaction conditions | 1:5.15 | a) *Sclerotium rolfsii.* | 0 | 0 | 32.93 |
| | | b) *Rhizoctonia solani* | 47.7 | 61.9 | 73.2 |
| | | c) *Fusarium oxysporium* | 57.8 | 70.0 | 76.8 |
| | | d) *Pyricularia oryzae* | 74.2 | 86.2 | 100 |
| Cupric silicate synthesized at neutral pH reaction conditions | 1:0.78 | a) *Sclerotium rolfsii.* | 0.0 | 0.0 | 24.7 |
| | | b) *Rhizoctonia solani* | 22.9 | 44.0 | 59.0 |
| | | c) *Fusarium oxysporium* | 0.0 | 0.0 | 68.3 |
| | | d) *Pyricularia oryzae* | 72.7 | 85.5 | 88.5 |

TABLE 7

Viral disinfection property of functional transition metal silicate (cupric silicate)

| Name of the Material | | Percentage reduction (%) of bacteriophages | | |
|---|---|---|---|---|
| | | MS-2 | ØX174 | PRD-1 |
| Cupric silicate | Batch a | 91 | 88 | 96 |
| | Batch b | 89 | 95 | 94 |
| | Batch c | 94 | 92 | 98 |

TABLE 8

Trihalomethanes decontamination property of cupric silicate

| S. No. | Name of the compound | Concentration of (control) contaminant solution (ppm) | Retained (ppm) | Decontamination ability of the absorbant (ppm) |
|---|---|---|---|---|
| 1 | Chloroform | 0.9975 | 0.4146 | 5.4 ppm of THM mix |
| 2 | 1,1,1 Trichloroethane | 1.0016 | 0.4476 | |
| 3 | Tetrachloroethylene | 1.0005 | 0.6573 | |
| 4 | Trichloroethylene | 1.0006 | 0.4064 | |
| 5 | Bromodichloroethane | 1.0008 | 0.8012 | |
| 6 | Dibromochloroethane | 1.0003 | 0.7861 | |
| 7 | Tetrachloroethylene | 0.9987 | 0.6795 | |
| 8 | Bromoform | 0.9907 | 0.5455 | |
| 9 | 1,2,Dichloro-3-Bromopropane | 0.9423 | 0.6557 | |
| | Total Concentration of THM mix | 8.950 | 5.3939 | |

TABLE 9

Arsenic decontamination of immobilized functional transition metal silicates on activated alumina (size: above 1000 microns)

| S. No | Name of the material | Percentage of arsenic decontamination after treatment of 2.12 ppm arsenic containing water by passing through 10 cms size column at flow rate 10 ml/min |
|---|---|---|
| 1 | Cupric Silicate | 90.10 |
| 2 | Zinc Silicate | 91.98 |
| 3 | Manganese Silicate | 58.96 |
| 4 | Zirconium Silicate | 13.68 |

TABLE 10

Arsenic decontamination property of immobilized transition metal silicate (cupric silicate) on different sizes of activated alumina

| S. No | Name of the material | Amount of arsenic content in ppm after treatment of 1 liter sodium arsenate (2.4 ppm solution) in a 10 cm column at 10 ml/min flow rate | % decontamination |
|---|---|---|---|
| 1 | Cupric silicate (500 nm) | 0.114 | 95.58 |
| 2 | Cupric silicate (1000 nm) | 0.36 | 86.05 |
| 3 | Control (1000 nm) (activated alumina) | 0.68 | 73.64 |
| 4 | Control solution (without treatment) | 2.4 | 0 |

TABLE 11

Arsenic decontamination property of transition metal silicate (cupric silicate) immobilized on agropolymers

| S. No. | Name of the material | % decontamination of arsenic from 500 ppb of arsenic treated solution |
|---|---|---|
| 1 | Cupric silicate immobilized on agropolymer (250 mg) | 56.48 |

TABLE 12

Decontamination property of functional transition metal silicates by physical immobilization on quartz sand (250-500 microns size)

| S. No | Name of the material | Percentage of arsenic decontamination after treatment of 2.12 ppm arsenic containing water by passing through 10 cm size of the column at flow rate 10 ml/min. |
|---|---|---|
| 1 | Cupric silicate | 35 |
| 2 | Zinc silicate | 48.58 |
| 3 | Manganese silicate | 18.87 |
| 4 | Zirconium silicate | 8.49 |
| 5 | Sand as control | 1.88 |

TABLE 13

Mercury decontamination property of immobilized functional transition metal silicates on activated alumina and agropolymer

| S. No. | Name of material | Initial Mercury content (ppb) in a liter water | Mercury content (ppb) after 60 min of treatment with immobilized functional transition metal silicates (1 mg/ml). |
|---|---|---|---|
| 1 | Cupric silicate immobilized on agropolymer | 224.21 | Below detectable limits |
| 2 | Cupric silicate immobilized on activated alumina | 224.21 | Below detectable limits |
| 3 | Control | 224.21 | 224.21 |

TABLE 14

Protein decontamination property of functional transition metal silicates immobilized on agropolymers

| S. No | Name of the material | Protein binding (mg) after treatment with 100 ml of BSA solution (1 mg/ml concentration), 2 cm column at 8 ml/min flow rate. |
|---|---|---|
| 1 | Silver silicate | 10.0 |
| 2 | Cupric silicate | 15.4 |
| 3 | Zinc silicate | 3.0 |

TABLE 15

Pesticidal decontamination nature of functional transition metal silicate immobilized on agropolymers

| | | % decontamination from 10 ppm pesticide solution by 1 gm of sample in a column | | |
|---|---|---|---|---|
| S. No | Name of the material | Endosulphan | Cypermethrin | Chlorpyriphos |
| 1 | Cupric silicate immobilized on activated alumina | 59.7 | 62.4 | 46.6 |
| 2 | Cupric silicate immobilized on agropolymer | 61.7 | 83.4 | 49.1 |

TABLE 16

Bacterial (coliform) decontamination property of immobilized functional transition metal silicates on activated alumina

| S. No. | Name of the material | Percentage of coliform decontamination after treating 500 ml of coliform ($5 \times 10^5$) containing water at a flow rate of 10 ml/min from 10 cms length column of functional transition metal silicates immobilized on activated alumina |
|---|---|---|
| 1. | Silver silicate | 98 |
| 2. | Zinc silicate | 43 |
| 3. | Cupric silicate | 83 |
| 4. | Alumina as control | Below 0.1 |

TABLE 17

Bacterial decontamination property of immobilized transition metal silicates on agropolymers

| S. No | Type of material | Volume (ml) of the coliform bacteria $4 \times 10^4$/liter containing water passed through the column containing 250 mg of immobilized transition metal silicate on agropolymer | % decontamination |
|---|---|---|---|
| 1 | Cupric silicate immobilized on Agropolymer | 2000 | 99 |
| | | 2500 | 97.45 |
| | | 3000 | 94.87 |
| 2 | Silver silicate immobilized on Agropolymer | 3000 | 99 |
| 3 | Zinc silicate immobilized on Agropolymer | 1000 | 61.90 |
| | | 1500 | 14.28 |
| | | 2000 | 4.76 |

TABLE 18

Bacterial decontamination property of immobilized transition metal silicates on aluminium oxide and cellulose.

| S. No | Type of material selected for immobilization | Weight of material in the column | Volume(ml) of coliform containing water (460 col/ml) passed through column | % decontamination |
|---|---|---|---|---|
| 1 | Aluminium oxide ($Al_2O_3$) | 1.0 gm | 250 | 93.47 |
| 2 | Cellulose | 0.97 gm | 300 | 93.71 |
| 3 | Control (untreated water) | | 460 coliform col/ml | 100 |

TABLE 19

Bacterial decontamination property of immobilized transition metal silicates on quartz sand

| S. No | Name of the material immobilized on quartz sand | Bacterial coliform amount (per 500 ml) present before treating with functional transition metal silicates in column | Percentage of coliform decontamination after treating 500 ml coliform containing water at a flow rate of 10 ml/min from 10 cms length column of functional transition metal silicates coated on quartz sand |
|---|---|---|---|
| 1 | Cupric silicate | $3.88 \times 10^5$ | 83 |
| 2 | Zinc silicate | $3.62 \times 10^5$ | 34 |
| 3 | Manganese silicate | $3.78 \times 10^5$ | 5 |
| 4 | Zirconium silicate | $2.90 \times 10^5$ | 6 |
| 5 | Sand as control | $1.1 \times 10^6$ | Below 0.001 |

TABLE 20

Decontamination property of fungus (*Aspergillus* species) from a long time (6 months) stored water by using immobilized cupric silicate on agropolymer.

| S. No. | Type of material | Column size | Volume of water (ml) passed through column | Result |
|---|---|---|---|---|
| 1 | Cupric silicate immobilized on Agropolymers | 2 cm | 1 liter | No growth of fungus was observed when the treated water was placed on fungal growth media |
| 2 | Control | | | Growth of fungus was observed when the untreated water was placed on fungal growth media |

TABLE 21

Protozoan (*Cryptosporidium parvum*) decontamination property of immobilized functional transition metal silicates on agropolymer

| Name of the sample | Volume of the fraction passed through column | % Reduction of seeded *Cryptosporidium parvum* oocysts |
|---|---|---|
| Cupric Silicate immobilized on agropolymer | Fraction-A (20 ml) | >99.99 |
| | Fraction-B (50 ml) | >99.99 |
| | Fraction-C (80 ml) | >99.99 |

TABLE 22

A. Viral decontamination property of immobilized functional transition metal silicates
B. *E. Coli* decontamination nature of immobilized functional transition metal silicates

| | | Percent reduction (%) | | |
|---|---|---|---|---|
| | | A | | B |
| Sample | Weight of the sample used in column | Polio Lsc 1 | Rotavirus SA11 | *E. coli* O157:H7 |
| Cupric silicate immobilized on agropolymer | 1 gram | 55.9 | 48.8 | 99.4 |
| | 2 grams | 99.998 | 99.991 | 99.99 |
| Cupric silicate immobilized on activated alumina | 10 grams | 70.3 | 86.2 | 91.9 |
| | 20 grams | 99.3 | 99.8 | 99.5 |

TABLE 23

Trihalomethanes decontamination property of cupric silicate immobilized on silica gel

| S. No. | Name of the compound | Concentration of control contaminant solution (ppm) | Retained (ppm) | Decontamination ability of the absorbent (ppm) |
|---|---|---|---|---|
| 1 | Chloroform | 0.9975 | 0.9501 | 7.5 ppm of THM mix |
| 2 | 1,1,1 Trichloroethane | 1.0016 | 0.9689 | |
| 3 | Tetrachloroethylene | 1.0005 | 0.9362 | |
| 4 | Trichloroethylene | 1.0006 | 0.9650 | |
| 5 | Bromodichloroethane | 1.0008 | 0.8897 | |
| 6 | Dibromochloroethane | 1.0003 | 0.7885 | |
| 7 | Tetrachloroethylene | 0.9987 | 0.9041 | |
| 8 | Bromoform | 0.9907 | 0.7308 | |
| 9 | 1,2Dichloro-3-Bromopropane | 0.9423 | 0.4059 | |
| | Total Concentration of THM mix | 8.950 | 7.5392 | |

Chromatographic Conditions for estimation of Trihalomethanes

| | |
|---|---|
| GC | VARIAN CP 3800 with Head Space |
| Column | ZB-5 30 m × 0.25 u × 0.25 |
| Oven temperature | 35° C./5 min @ 10° C./min 250° C./1 min |
| Detector | Electron Capture Detector |
| Detector Temperature | 300° C. |
| Injection Temperature | 200° C. with split less mode |
| Carrier gas | Nitrogen |
| Flow | 0.5 ml/min |
| Makeup gas flow | 29 ml/min |
| Range | 1.0 |
| Run time | 27.473 min |

TABLE 24

Semi volatile organic compounds decontamination property of cupric silicate (immobilized on silica gel)

| S. No. | Name of compound | Concentration of control contaminant solution (ppm) | Retained (ppm) | Decontamination ability of the absorbent (ppm) |
|---|---|---|---|---|
| 1 | Benzene, 1,4,-dichloro | 0.696 | 0.17 | 9.1 ppm of the SVOCs mix. |
| 2 | Ethane Hexachloro | 0.860 | 0.546 | |
| 3 | Benzene 1,2,3, trichloro | 0.8806 | 0.184 | |
| 4 | 1,3 Butadiene, 1,1,2,3,4 | 0.775 | 0.437 | |
| 5 | Naphthalene, 2-chloro | 0.876 | 0.644 | |
| 6 | Acenaphthylene | 0.812 | 0.526 | |
| 7 | Acenapthene | 0.775 | 0.488 | |
| 8 | Phenol, 2,4-bis(1,1-imet | 0.351 | 0.000 | |
| 9 | Diethyl Phthalate | 0.768 | 0.467 | |
| 10 | Fluorene | 0.793 | 0.518 | |
| 11 | Benzene 1-chloro-3pheno | 0.574 | 0.386 | |
| 12 | Diphenylamine | 0.634 | 0.568 | |
| 13 | 4-Bromophenyl-phenylether | 0.861 | 0.632 | |
| 14 | Bezene, hexachloro | 0.542 | 0.310 | |
| 15 | Phenantherene | 0.772 | 0.465 | |
| 16 | Anthracene | 0.812 | 0.528 | |
| 17 | Dibutyl phthalate | 0.693 | 0.275 | |
| 18 | Fluoranthene | 0.706 | 0.276 | |
| 19 | Pyrene | 0.700 | 0.252 | |
| 20 | Benzyl butyl phthalate | 0.691 | 0.187 | |
| 21 | Chrysene | 0.644 | 0.206 | |
| 22 | Bis(2-ethylhexyl)phthalate | 0.676 | 0.134 | |
| 23 | Phenol, 2,3,4,5-tetrabrom | 0.671 | 0.124 | |
| 24 | Di-n-octyl phthalate | 0.729 | 0.105 | |
| 25 | Benzo(b) Fluoranthene | 0.698 | 0.061 | |
| 26 | Benzo(k) fluoranthene | 0.670 | 0.066 | |

TABLE 24-continued

Semi volatile organic compounds decontamination property of cupric silicate (immobilized on silica gel)

| S. No. | Name of compound | Concentration of control contaminant solution (ppm) | Retained (ppm) | Decontamination ability of the absorbent (ppm) |
|---|---|---|---|---|
| 27 | Benzo (a) pyrene | 0.680 | 0.035 | |
| 28 | Indeno(1,2,3-cd) pyrene | 0.533 | 0.000 | |
| 29 | Dibenzo(a,h) anthracene | 0.430 | 0.43 | |
| 30 | Benzo(g,h,l) perylene | 0.517 | 0.039 | |
| | Total Concentration of SVOCS Mix | 20.8196 | 9.059 | |

Chromatographic conditions for estimation of semi volatile organic compounds

| | |
|---|---|
| GC MS | VARIAN CP 3800 WITH GC-MS SATURN 2000 GC/MS/MS. |
| Column | WCOT Fused silica 30M × 0.25 mm Id, Coating CP-SIL 8 CB |
| Low Bleed/MS DF | 0.25. |
| Cat. No | CP 5860 |
| Oven temperature | 60° C. @ 7.0° C./min, 130° C. @ 5.0° C./min, 200° C. @ 6.0° C./min, 260° C. @ 20.0° C./min, 280° C. @ 15 min. |
| Injection Temperature | 280° C. with split less mode. |
| Carrier Gas | Helium |
| Flow Rate | 1.0 ml/min. |
| Run time | 50.0 min. |
| MS Conditions | |
| Emission Current | 10 micro amps. |
| Mass Defect | 0 mmu/100 u |
| Count Threshold | 2 counts. |
| Multiplier offset | 0 volts |
| Cal Gas | OFF |
| Scan Time | 0.810 seconds |
| Segment start time | 3.00 minutes. |
| Segment end time | 50.00 minutes. |
| Segment low mass | 45 m/z |
| Segment high Mass | 450 m/z |
| Ionization Mode | EI AGC |
| Ion preparation Technique | NONE |

TABLE 25

Volatile organic compounds decontamination property of cupric silicate (immobilized on silica gel)

| S. No. | Name of compound | Concentration of control contaminant solution (ppm) | Retained (ppm) | Decontamination of the absorbent (ppm) |
|---|---|---|---|---|
| 1 | 1,1,1-Trichloroethane | 0.500 | 0.500 | 10.8 ppm of VOC mix |
| 2 | 1,1,2-Trichloroethane | 0.500 | 0.500 | |
| 3 | 1,3-Dichloropropane | 0.500 | 0.500 | |
| 4 | Dibromochloromethane | 0.500 | 0.500 | |
| 5 | Ethane 1,2-Dibromo | 0.500 | 0.500 | |
| 6 | Chlorobenzene | 0.500 | 0.469 | |
| 7 | Benzene 1,3-dimethyl | 0.500 | 0.500 | |
| 8 | Orthoxylene | 0.500 | 0.500 | |
| 9 | Benzene 1-methylethyl | 0.500 | 0.500 | |
| 10 | Ethane 1,1,2,2-Tetrachloro | 0.500 | 0.488 | |
| 11 | Bromobenzene | 0.500 | 0.347 | |
| 12 | 2-chloro Toluene | 0.500 | 0.182 | |
| 13 | Benzene, propyl | 0.500 | 0.168 | |
| 14 | Benzene, 1Chloro 4-methyl | 0.500 | 0.246 | |
| 15 | Benzene 1,2,3-Trimethyl | 0.500 | 0.229 | |
| 16 | 4-Iso propyl Toluene | 0.500 | 0.281 | |
| 17 | Benzene 1,2-Diethyl | 0.500 | 0.281 | |
| 18 | Benzene 1,2-Dichloro | 0.500 | 0.328 | |
| 19 | 1,3-Dichlorobenzene | 0.500 | 0.346 | |
| 20 | 1,4-Dichlorobenzene | 0.500 | 0.477 | |
| 21 | Benzene 1,3,4-trichloro | 0.500 | 0.500 | |
| 22 | 1,3-Butadiene1,1,2,3,4 | 0.500 | 0.007 | |
| 23 | Benzene 2-Bromo 1,3,5 | 0.500 | 0.281 | |
| 24 | Nitrobenzene | 0.500 | 0.500 | |
| 25 | Styrene | 0.500 | 0.051 | |
| 26 | Benzylbenzoate | 0.500 | 0.100 | |
| 27 | 1,2,3,4-Tetramethylbenzene | 0.500 | 0.122 | |
| 28 | Benzene 1-Chloro 2-propyl | 0.500 | 0.325 | |
| 29 | 4-Bromo 3-chloroanilene | 0.500 | 0.097 | |
| | Total Concentration of VOCs mix | 18.500 | 10.825 | |

Chromatographic conditions for estimation of volatile organic compounds

| | |
|---|---|
| GC MS | VARIAN CP 3800 WITH GC-MS SATURN 2000 GC/MS/MS. |
| Column | WCOT Fused silica 30M × 0.25 mm Id, Coating CP-SIL 8 CB |
| Low Bleed/MS DF | 0.25 |
| Cat. No | CP 5860 |
| Oven temperature | 40° C./10 min @ 3.0° C./min, 200° C./10 min. |
| Injection Temperature | 200° C. with split less mode. |
| Carrier Gas | Helium |
| Flow Rate | 1.0 ml/min. |
| Run time | 50.0 min. |
| MS Conditions | |
| Emission Current | 10 micro amps. |
| Mass Defect | 0 mmu/100 u |
| Count Threshold | 2 counts. |
| Multiplier offset | 0 volts |
| Cal Gas | OFF |
| Scan Time | 0.810 seconds |
| Segment start time | 3.00 minutes. |
| Segment end time | 50.00 minutes. |
| Segment low mass | 45 m/z |
| Segment high Mass | 450 m/z |
| Ionization Mode | EI AGC |
| Ion preparation Technique | NONE |

TABLE 26

Phenols decontamination property of cupric silicate (immobilized on silica gel)

| S. No. | Name of compound | Concentration of control contaminant solution (ppm) | Retained (ppm) | Decontamination ability of the absorbant (ppm) |
|---|---|---|---|---|
| 1 | Benzoic Acid | 1.086 | 0.3475 | 2.8 ppm of Phenols mix |
| 2 | 2,4,5-Trichlorophenol | 0.7083 | 0.1077 | |

TABLE 26-continued

Phenols decontamination property of cupric silicate (immobilized on silica gel)

| S. No. | Name of compound | Concentration of control contaminant solution (ppm) | Retained (ppm) | Decontamination ability of the absorbant (ppm) |
|---|---|---|---|---|
| 3 | 3-Nitroaniline | 1.3042 | 0.3402 | |
| 4 | 4-Nitrophenol | 1.1396 | 0.5004 | |
| 5 | 2,4-Dinitrophenol | 1.0523 | 0.5258 | |
| 6 | 4-Nitroaniline | 1.0898 | 0.5351 | |
| 7 | Pentachlorophenol | 1.1432 | 0.4607 | |
| | Total Concentration of Phenols mix | 7.5234 | 2.8175 | |

Chromatographic Conditions for estimation of Phenols

| | |
|---|---|
| GC | VARIAN CP 3800 with Head Space |
| Column | ZB-WAX 30 m × 0.25 u × 0.25 |
| Oven temperature | 110° C./2 min @ 10° C./min 250° C./1 min |
| Detector | Flame Ionization Detector |
| Detector Temperature | 275° C. |
| Injection Temperature | 250° C. with split less mode |
| Carrier gas | Nitrogen |
| Flow | 1.0 ml/min |
| Range | 12 |

TABLE 27

Polychlorinated biphenyls decontamination property of cupric silicate immobilized on silica gel

| S. No. | Name of compound | Concentration of control contaminant solution (ppm) | Retained (ppm) | Decontamination ability of the absorbant (ppm) |
|---|---|---|---|---|
| 1 | 2,3-Dichlorobiphenyl | 0.4677 | 0.2723 | 2.4 ppm of PCB mix |
| 2 | Trichlorobiphenyl | 0.5312 | 0.2958 | |
| 3 | Tetrachlorobiphenyl | 0.5279 | 0.3426 | |
| 4 | Pentachlorobiphenyl | 0.5174 | 0.3501 | |
| 5 | Hexachlorobiphenyl | 0.5094 | 0.3687 | |
| 6 | Heptachlorobiphenyl | 0.5015 | 0.4161 | |
| 7 | Octachlorobiphenyl | 0.5178 | 0.3845 | |
| | Total Concentration of PCB mix | 3.5729 | 2.43 | |

Chromatographic Conditions for estimation of Polychlorinated Biphenyls.

| | |
|---|---|
| GC | VARIAN CP 3800 with Head Space |
| Column | ZB-5 30 m × 0.25 u × 0.25 |
| Oven temperature | 110° C./1 min @ 20° C./min 280° C./10 min |
| Detector | Electron Capture Detector |
| Detector Temperature | 300° C. |
| Injection Temperature | 250° C. with Split less mode |
| Carrier gas | Nitrogen |
| Flow | 1.0 ml/min |
| Makeup gas Flow | 29 ml/min |
| Range | 1.0 |
| Run Time | 19.50 min |

TABLE 28

Trihalomethanes decontamination property of zinc silicate immobilized on silica gel

| S. No. | Name of the compound | Concentration of control contaminant solution (ppm) | Retained (ppm) | Decontamination ability of the absorbant (ppm) |
|---|---|---|---|---|
| 1 | Chloroform | 1.0380 | 0.2471 | 6.8 ppm of THM mix |
| 2 | 1,1,1 Trichloroethane | 0.9857 | 0.9857 | |
| 3 | Tetrachloroethylene | 1.0083 | 0.6021 | |
| 4 | Trichloroethylene | 1.0110 | 0.7881 | |
| 5 | Bromodichloroethane | 1.0243 | 0.9311 | |
| 6 | Dibromochloroethane | 1.0302 | 0.8841 | |
| 7 | Tetrachloroethylene | 1.0117 | 0.7733 | |
| 8 | Bromoform | 1.0314 | 0.7056 | |
| 9 | 1,2 Dichloro-3-Bromopropane | 1.0319 | 0.8541 | |
| | Total Concentration of THM mix | 9.1725 | 6.7712 | |

TABLE 29

Trihalomethanes decontamination property of silver silicate immobilized on silica gel

| S. No. | Name of compound | Concentration of control contaminant solution (ppm) | Retained (ppm) | Decontamination ability of the absorbant (ppm) |
|---|---|---|---|---|
| 1 | Chloroform | 1.038 | 0.5317 | 7.2 ppm of THM mix |
| 2 | 1,1,1 Trichloroethane | 0.9857 | 0.9857 | |
| 3 | Tetrachloroethylene | 1.0083 | 0.6784 | |
| 4 | Trichloroethylene | 1.011 | 0.7789 | |
| 5 | Bromodichloroethane | 1.0243 | 0.8685 | |
| 6 | Dibromochloroethane | 1.0302 | 0.8543 | |
| 7 | Tetrachloroethylene | 1.0117 | 0.8872 | |
| 8 | Bromoform | 1.0314 | 0.8542 | |
| 9 | 1,2 Dichloro-3-Bromopropane | 1.0319 | 0.7367 | |
| | Total Concentration of THM mix | 9.1725 | 7.1756 | |

TABLE 30

Trihalomethanes decontamination property of manganese silicate immobilized on silica gel

| S. No. | Name of the compound | Concentration of control contaminant solution (ppm) | Retained (ppm) | Decontamination ability of the absorbant (ppm) |
|---|---|---|---|---|
| 1 | Chloroform | 1.038 | 0.6732 | 7.5 ppm of THM mix |
| 2 | 1,1,1 Trichloroethane | 0.9857 | 0.9857 | |
| 3 | Tetrachloroethylene | 1.0083 | 0.0000 | |
| 4 | Trichloroethylene | 1.011 | 0.9011 | |
| 5 | Bromodichloroethane | 1.0243 | 0.9928 | |
| 6 | Dibromochloroethane | 1.0302 | 0.9975 | |
| 7 | Tetrachloroethylene | 1.0117 | 0.9916 | |
| 8 | Bromoform | 1.0314 | 0.9921 | |
| 9 | 1,2Dichloro-3-Bromopropane | 1.0319 | 0.9604 | |
| | Total Concentration of THM mix | 9.1725 | 7.4944 | |

TABLE 31

Trihalomethanes decontamination property of zirconium silicate immobilized on silica gel

| S. No. | Name of the compound | Concentration of control contaminant solution (ppm) | Retained (ppm) | Decontamination ability of the absorbant (ppm) |
|---|---|---|---|---|
| 1 | Chloroform | 1.038 | 0.2227 | 5.1 ppm of THM mix |
| 2 | 1,1,1 Trichloroethane | 0.9857 | 0.7011 | |
| 3 | Tetrachloroethylene | 1.0083 | 0.4120 | |
| 4 | Trichloroethylene | 1.011 | 0.6268 | |
| 5 | Bromodichloroethane | 1.0243 | 0.7130 | |
| 6 | Dibromochloroethane | 1.0302 | 0.6321 | |
| 7 | Tetramochloroethylene | 1.0117 | 0.8006 | |
| 8 | Bromoform | 1.0314 | 0.4384 | |
| 9 | 1,2 Dichloro-3-Bromopropane | 1.0319 | 0.5112 | |
| | Total Concentration of THM mix | 9.1725 | 5.0579 | |

TABLE 32

Bacterial decontamination property of immobilized functional transition metal silicates (5%) incorporated in to bisphenol resins

| Type of material selected for incorporation | Weight of material | Volume (ml) of coliform containing water ($4.6 \times 10^5$/liter) passed | % decontamination |
|---|---|---|---|
| Cupric silicate (5%) incorporated into Bisphenol resins | 3.6 gm | 200 | 70 |

TABLE 33

Bacterial decontamination property of functional transition metal silicate resin coatings on quartz sand

| S. No | Type of material | Volume (ml) of the coliform bacteria $3.23 \times 10^5$/liter containing water passed through the 5 cm size materials in column | % decontamination |
|---|---|---|---|
| 1 | 1 gm of cupric silicate mixed with 10 ml of isopthalic resin was coated on 100 ml volume of quartz | 500 | 28.79 |
| | | 1000 | 20.12 |

TABLE 33-continued

Bacterial decontamination property of functional transition metal silicate resin coatings on quartz sand

| S. No | Type of material | Volume (ml) of the coliform bacteria $3.23 \times 10^5$/liter containing water passed through the 5 cm size materials in column | % decontamination |
|---|---|---|---|
| | sand (500 microns) | | |

TABLE 34

Toxic gas (engine combustion) detoxification (%) nature of immobilized functional transition metal silicates

| S. No | Material | Column size | $No_x$ (oxides of nitrogen) % | $So_2$ % |
|---|---|---|---|---|
| 1 | Cupric silicate immobilized on silica gel | 20 cm | 46.8 | 88.1 |
| 2 | Zinc silicate immobilized on silica gel | 20 cm | 16.57 | 93.76 |
| 3 | Silver silicate immobilized on silica gel | 20 cm | 36.0 | 92.5 |
| 4 | Manganese silicate immobilized on silica gel | 20 cm | 22.45 | 91.13 |
| 5 | Cupric silicate containing resin coated on quartz sand | 20 cm | 43.67 | 96.05 |
| 6 | Silica as control | 20 cm | 17.2 | 94.0 |

TABLE 35

Tar and nicotine absorption property of immobilized functional transition metal silicates

| S. No | Name of the sample | Tar amount (mg) absorbed by Immobilized functional transition metal silicate | Nicotine amount (mg) absorbed by immobilized functional transition metal silicate |
|---|---|---|---|
| 1 | Zinc silicate on Silica gel | 17.0 | 0.60 |
| 2 | Manganese silicate on silica gel | 22.75 | 0.59 |
| 3 | Cupric silicate on silica gel | 26.25 | 0.73 |
| 4 | Silver silicate on silica gel | 14.5 | 0.30 |
| 5 | Zirconium silicate on Alumina | 2.5 | 0.29 |

Brand name of Cigarette: Charms (normal)
Cigarette length: 6 cm, average weight: 0.775 grams.

TABLE 36

Cigarette smoke detoxification nature (%) of immobilized functional transition metal silicates

| S. No. | Name of the materials | Immobilized on | Weight of the materials | CO % detoxification | $No_x$ % detoxification | $SO_2$ % detoxification | Hydrocarbons % detoxification |
|---|---|---|---|---|---|---|---|
| 1 | Cupric silicate | Silica gel | 500 mg | 68.2 | 64.86 | 63.96 | 44.85 |
| 2 | Manganese silicate | Silica gel | 500 mg | 54.2 | 32.43 | 40.5 | 29.0 |
| 3 | Zinc Silicate | Silica gel | 500 mg | 38.5 | 23.4 | 12.6 | 34.2 |
| 4 | Zirconium silicate | Alumina | 500 mg | 73.34 | 68.46 | 71.17 | 44.11 |

TABLE 36-continued

Cigarette smoke detoxification nature (%) of immobilized functional transition metal silicates

| S. No. | Name of the materials | Immobilized on | Weight of the materials | CO % detoxification | $No_x$ % detoxification | $SO_2$ % detoxification | Hydrocarbons % detoxification |
|---|---|---|---|---|---|---|---|
| 5 | Cupric silicate | Agropolymer | 300 mg | 66.29 | 63.96 | 67.56 | 34.55 |

Cigarette weight: 0.775 grams.
Brand name of Cigarette: Charminar (normal)
Cigarette length: 6 cm, average weight: 0.775 grams.

The invention claimed is:

1. A method for controlling microbes selected from the group consisting of protozoa, bacteria, fungi, viruses, and combinations thereof, said method comprising contacting the microbe with a composition comprising crystalline cupric silicate wherein the cupric silicate is:
   i) a cupric silicate having a silica to copper ratio of 1:5.15;
   ii) a cupric silicate having a silica to copper ratio of 1:0.78;
   iii) a cupric silicate having a silica to copper ratio of 1:0.53;
   iv) a cupric silicate having a silica to copper ratio of 1:0.34;
or a mixture of two or more of them.

2. The method of claim 1, wherein the cupric silicate is immobilized.

3. The method of claim 1 wherein
   the cupric silicate i) exhibits the following characteristics: characteristic g values of electron spin resonance peaks being (a) 4.3; (b) 2.5; (c) 2.3; (d) 2.0 and (e) 2.0; and an X-ray diffraction pattern having 3 significant peaks at 16.2, 32.2 and 39.7 having peak heights of 2128, 1593 and 1470, respectively;
   the cupric silicate ii) exhibits the following characteristics: characteristic g values of electron spin resonance peaks being (a) 2.2 and (b) 2.0; and an X-ray diffraction pattern having 3 significant peaks at 16, 32 and 39 having peak heights of 835, 706 and 502, respectively;
   the cupric silicate iii) exhibits the following characteristics: characteristic g values of electron spin resonance peaks being (a) 2.1, (b) 2.0 and (c) 2.1; and an X-ray diffraction pattern having 3 significant peaks at 16.1, 32.2 and 39.71 having peak heights of 400, 394 and 330, respectively; and
   the cupric silicate iv) exhibits the following characteristics: characteristic g values of electron spin resonance peaks being (a) 2.1, and (b) 2.0; and an X-ray diffraction pattern having 3 significant peaks at 16.2, 32.3 and 39.8 having peak heights of 541, 414 and 365 respectively.

4. The method of claim 2 wherein
   the cupric silicate i) exhibits the following characteristics: characteristic g values of electron spin resonance peaks being (a) 4.3; (b) 2.5; (c) 2.3; (d) 2.0 and (e) 2.0; and an X-ray diffraction pattern having 3 significant peaks at 16.2, 32.2 and 39.7 having peak heights of 2128, 1593 and 1470, respectively;
   the cupric silicate ii) exhibits the following characteristics: characteristic g values of electron spin resonance peaks being (a) 2.2 and (b) 2.0; and an X-ray diffraction pattern having 3 significant peaks at 16, 32 and 39 having peak heights of 835, 706 and 502, respectively;
   the cupric silicate iii) exhibits the following characteristics: characteristic g values of electron spin resonance peaks being (a) 2.1, (b) 2.0 and (c) 2.1; and an X-ray diffraction pattern having 3 significant peaks at 16.1, 32.2 and 39.71 having of 400, 394 and 330, respectively; and
   the cupric silicate (iv) exhibits the following characteristics: characteristic g values of electron spin resonance being (a) 2.1, and (b) 2.0; and an X-ray diffraction pattern having 3 significant peaks at 16.2, 32.3 and 39.8 having peak heights of 541, 414 and 365, respectively.

5. The method of claim 1, wherein the bacteria is selected from the group consisting of coliform bacteria, Gram Positive bacteria, Gram Negative bacteria, or a combination thereof.

6. The method of claim 1, wherein the protozoa is *Crytosporidium parvum*.

7. The method of claim 1, wherein the fungus is a pathogenic fungus selected from the group consisting of *Sclerotium rolfsil, Rhizoctonia solani, Fusarium oxysporium, Pyricularia oryzae, Aspergillus* sps, or a combination thereof.

8. The method of claim 2, wherein the at least one cupric silicate is immobilized on an agropolymer, activated alumina, silica gel, cellulose, or resin-coated quartz sand.

9. The method of claim 1, wherein the at least one cupric silicate is immobilized on an agropolymer, activated alumina, silica gel, cellulose, or resin-coated quartz sand.

10. The method of claim 1, wherein the cupric silicate is produced by a method comprising:
   i) adding a solution of a soluble copper salt to a solution of a soluble alkali silicate to form a mixture, and optionally adding a mineral acid, to obtain a mixture having a pH below 6;
   ii) collecting the precipitate that forms; and
   iii) washing the precipitate to obtain a cupric silicate composition comprising crystalline cupric silicate.

* * * * *